(12) United States Patent
Gambhir et al.

(10) Patent No.: US 7,939,649 B2
(45) Date of Patent: May 10, 2011

(54) POLYNUCLEOTIDE ENCODING LUCIFERASE

(75) Inventors: Sanjiv S. Gambhir, Portolla Valley, CA (US); Andreas M. Loening, Stanford, CA (US); Anna M. Wu, Sherman Oaks, CA (US)

(73) Assignees: Stanford University, Palo Alto, CA (US); Regents of University of California, Oakland, CA (US)

( * ) Notice: Subject to any disclaimer, the term of this patent is extended or adjusted under 35 U.S.C. 154(b) by 329 days.

(21) Appl. No.: 11/995,586

(22) PCT Filed: Sep. 6, 2006

(86) PCT No.: PCT/US2006/034601
§ 371 (c)(1),
(2), (4) Date: Jan. 14, 2008

(87) PCT Pub. No.: WO2007/030473
PCT Pub. Date: Mar. 15, 2007

(65) Prior Publication Data
US 2009/0136998 A1   May 28, 2009

Related U.S. Application Data

(60) Provisional application No. 60/714,640, filed on Sep. 6, 2005, provisional application No. 60/714,969, filed on Sep. 7, 2005, provisional application No. 60/834,752, filed on Aug. 1, 2006.

(51) Int. Cl.
*C07H 21/04* (2006.01)
*C12N 5/00* (2006.01)

(52) U.S. Cl. ..................... 536/23.2; 435/325

(58) Field of Classification Search ............... 536/23.2; 435/325
See application file for complete search history.

(56) References Cited

U.S. PATENT DOCUMENTS
6,143,502 A   11/2000  Grentzmann et al.
2001/0039016 A1 *  11/2001  Waldman et al. ............... 435/6

FOREIGN PATENT DOCUMENTS
WO   WO 02/16944   *   2/2002

OTHER PUBLICATIONS

GenBank (AF214570.1 submitted in 1999. See printout from http://www.ncbi.nlm.nih.gov/nuccore/AD214570.1. Printed Mar. 23, 2010, p. 1-2).*
Bermont (Bermont et al. In J Cancer 85:117-123, 2000).*
Optical Imaging of Renilla Luciferase Reporter Gene Expression in Living Mice, Bhaumik, S., and Gambhir, S.S., PNAS, Jan. 8, 2002, vol. 99, No. 1, pp. 377-382.

* cited by examiner

*Primary Examiner* — Thaian N Ton
*Assistant Examiner* — Marcia S Noble
(74) *Attorney, Agent, or Firm* — Thomas, Kayden, Horstemeyer & Risley, LLP

(57) ABSTRACT

Briefly described, embodiments of this disclosure include polynucleotides that encode mutant Cnidarian luciferases that exhibit modulated properties as compared to the corresponding wild-type luciferases, and the modulated properties include at least one of: modulated stability; enhanced light output; and modulated emission maximum. Embodiments of the present disclosure also include polypeptides or fragments thereof encoded by the polynucleotides, constructs including the polynucleotide, expression cassettes, cells, methods of producing the polynucleotides and polypeptides, antibodies, transgenic cells and/or animals, kits, and the like.

14 Claims, 10 Drawing Sheets

A

B a) Coomassie Blue       b) Western Blots c)

US 7,939,649 B2

POLYNUCLEOTIDE ENCODING LUCIFERASE

CROSS-REFERENCE TO RELATED APPLICATION

This application claims priority to "LUCIFERASES AND METHODS FOR MAKING AND USING THE SAME," having Ser. No. PCT/US2006/034601, filed on Sep. 6, 2006. This application claims priority to each of the following U.S. provisional applications: "LUCIFERASES AND METHODS FOR MAKING AND USING THE SAME," having Ser. No. 60/714,640, filed on Sep. 6, 2005; "IMPROVED LUCIFERASES AND METHODS FOR MAKING AND USING THE SAME," having Ser. No. 60/714,969, filed on Sep. 7, 2005; and "RED-SHIFTED RENILLA LUCIFERASE PROTEINS AND METHODS OF USE THEREOF," having Ser. No. 60/834,752, filed on Aug. 1, 2006, each of which are entirely incorporated herein by reference.

FEDERALLY-SPONSORED RESEARCH OR DEVELOPMENT

This invention: was made with Government support under contract CA082214 awarded by the National Institutes of Health. The Government has certain rights in this invention.

BACKGROUND

Luminescence is a phenomenon in which energy is specifically channeled to a molecule to produce an excited state. Return to a lower energy state is accompanied by release of a photon. Luminescence includes fluorescence, phosphorescence, chemiluminescence and bioluminescence. Bioluminescence is the process by which living organisms emit light that is visible to other organisms. Where the luminescence is bioluminescence, creation of the excited state derives from an enzyme catalyzed reaction.

During the past twenty years, high-sensitivity biochemical assays used in research and in medicine have increasingly employed luminescence and fluorescence rather than radioisotopes. This change has been driven partly by the increasing expense of radioisotope disposal and partly by the need to find more rapid and convenient assay methods. More recently, the need to perform biochemical assays in situ in living cells and whole animals has driven researchers toward protein-based luminescence and fluorescence.

Since the cloning of a luciferase from the firefly, luciferase genes have become essential components of biological research. They are used ubiquitously as reporter genes in cell culture experiments, and their use as reporters has been extended into the context of small animal imaging. Recently, it has been proposed that the luciferase protein itself could be conjugated to other proteins such as antibodies or growth factors, and these bioluminescently labeled ligands could then be used for imaging of receptor targets in small animals. The advantage of using a bioluminescent entity to label a protein over similar fluorescent or radioactive approaches is that in the context of small animal imaging the bioluminescent approach has the potential to be more sensitive.

The beetle luciferases (e.g., firefly), however, are not optimal for employment as bioluminescent tags. These luciferases are not particularly small (~62 kDa) and are dependent on ATP, molecular oxygen, and magnesium for activity. The dependence on ATP especially would hinder the application of beetle luciferases as bioluminescent tags in vivo, since serum ATP concentrations are generally below 10 nM.

Luciferases that use coelenterazine as their substrate are more appropriate for application as bioluminescent tags, as these enzymes are not ATP dependent and in general require only molecular oxygen in addition to coelenterazine for luminescence. From this group of proteins, the luciferase from *Renilla reniformis* (RLuc1) is the best characterized, in addition to being of a size (36 kDa) more appropriate for use as a tag.

The limiting factor for use of RLuc as a bioluminescent tag is its limited stability under in vivo conditions. A single point mutation of RLuc (C124A) that increases the enzyme's stability several fold has been reported, however even this level of stability is insufficient for the tagging of large proteins (e.g., antibodies) that require time scales on the order of days to sufficiently distribute.

An additional limitation to the use of any of the known coelenterazine utilizing luciferases is that the spectral peaks of these luciferases lie in the blue region of the visible spectrum. For in vitro assays such as cell culture transfection studies, the wavelength of light that a luciferase yields is usually of little consequence. For in vivo assays such as small animal imaging studies, the wavelength is important because biological tissues are less attenuating to the red and near-infrared portions of the optical spectrum. In the case of *Renilla* Luciferase the spectral peak is at 482 nm, with only about 3-4% of the photons of wavelengths above 600 nm. For luciferase at depths greater than superficial depths, the majority of the photons that actually make it out of the animal are these few above 600 nm wavelength photons.

As such, there is a continued need in the art for the development of luciferases that exhibit improved properties. The present disclosure addresses this and other needs.

SUMMARY

Briefly described, embodiments of this disclosure include polynucleotides that encode mutant *Cnidarian* luciferases that exhibit modulated properties as compared to the corresponding wild-type luciferase, and the modulated properties include at least one of: modulated stability; enhanced light output; and modulated emission maximum. Embodiments of the present disclosure also include polypeptides or fragments thereof encoded by the polynucleotides, constructs including the polynucleotide, expression cassettes, cells, methods of producing the polynucleotides and polypeptides, antibodies, transgenic cells and/or animals, kits, and the like.

An embodiment of the present disclosure includes polynucleotides that are present in other than their naturally occurring environment and that encode a mutant *Cnidarian* luciferase. The mutant *Cnidarian* luciferase exhibits modulated properties as compared to its corresponding wild-type luciferase, and the modulated properties included at least one of: modulated stability, enhanced light output, and modulated emission maximum.

An embodiment of the present disclosure includes constructs that include a vector and a polynucleotide as described herein.

An embodiment of the present disclosure includes expression cassettes that include a transcriptional initiation region functional in an expression host; a polynucleotide as described herein; and a transcriptional termination region functional in the expression host.

An embodiment of the present disclosure includes cells, or the progeny thereof, that include an expression cassette as described herein as part of an extrachromosomal element or integrated into the genome of a host cell as a result of introduction of the expression cassette into the host cell.

An embodiment of the present disclosure includes methods of producing a luciferase that include growing a cell as described herein, whereby the protein is expressed, and isolating the protein so that it is substantially free of other proteins.

An embodiment of the present disclosure includes proteins or fragments thereof encoded by a polynucleotide as described herein.

An embodiment of the present disclosure includes antibodies binding specifically to a protein as described herein.

An embodiment of the present disclosure includes transgenic cells or the progeny thereof that include a transgene that includes a polynucleotide as described herein.

An embodiment of the present disclosure includes transgenic organisms that include a transgene that includes a polynucleotide as described herein.

An embodiment of the present disclosure includes applications as described herein that employ the polynucleotides and/or polypeptides or fragments thereof as described herein.

An embodiment of the present disclosure includes kits that include a polynucleotide as described herein.

An embodiment of the present disclosure includes kits that include a protein or fragment thereof encoded by a polynucleotide as described herein.

An embodiment of the present disclosure includes polynucleotides that encode a mutant *Cnidarian* luciferase. The mutant *Cnidarian* luciferase exhibits modulated properties as compared to its corresponding wild-type luciferase, and the modulated properties include at least one of: modulated stability, enhanced light output, and modulated emission maximum.

An embodiment of the present disclosure includes polypeptides having modulated properties as compared to their corresponding wild-type luciferase and where the modulated properties include at least one of: modulated stability, enhanced light output, and modulated emission maximum.

BRIEF DESCRIPTION OF THE FIGURES

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
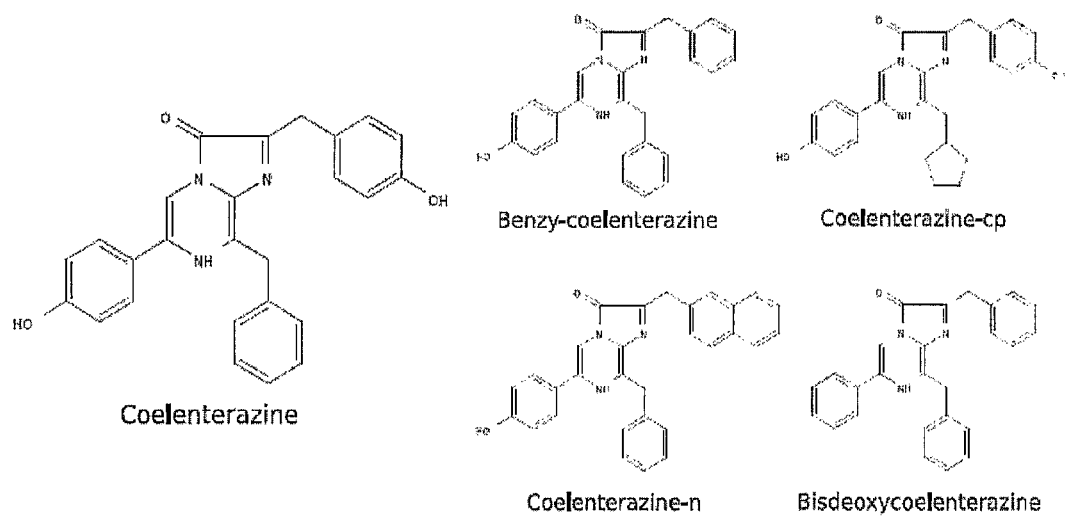
FIG. 1 illustrates the chemical structures of coelenterazine and several analogs.

Before the present disclosure is described in greater detail, it is to be understood that this disclosure is not limited to particular embodiments described, as such may, of course, vary. It is also to be understood that the terminology used herein is for the purpose of describing particular embodiments only and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

"Bioluminescent donor protein" refers to a protein capable of acting on a bioluminescent initiator molecule to generate bioluminescence.

"Bioluminescent initiator molecule" is a molecule that can react with a bioluminescent donor protein to generate bioluminescence.

As used herein, the terms "antibody" and "antibodies" can include, but are not limited to, monoclonal antibodies, multispecific antibodies, human antibodies, humanized antibodies, camelised antibodies, chimeric antibodies, single-chain Fvs (scFv), single chain antibodies, Fab fragments, F(ab') fragments, disulfide-linked Fvs (sdFv), and anti-idiotypic (anti-Id) antibodies (e.g., anti-Id antibodies to antibodies of the disclosure), and epitope-binding fragments of any of the above. In particular, antibodies include immunoglobulin molecules and immunologically active fragments of immunoglobulin molecules (e.g., molecules that contain an antigen binding site). Immunoglobulin molecules can be of any type (e.g., IgG, IgE, IgM, IgD, IgA and IgY), class (e.g., IgG1, IgG2, IgG3, IgG4, IgA1 and IgA2), or subclass. The antibodies may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes. The antibodies may be monospecific, bispecific, trispecific, or of greater multispecificity.

As used herein, "humanized" describes antibodies wherein some, most or all of the amino acids outside the CDR regions are replaced with corresponding amino acids derived from human immunoglobulin molecules. In one embodiment of the humanized forms of the antibodies, some, most, or all of the amino acids outside the CDR regions have been replaced with amino acids from human immunoglobulin molecules but where some, most, or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press. Wilson, T. and Hastings, J. W. (1998). Bioluminescence. *Annu Rev Cell Dev Biol* 14, 197-230.). Bioluminescence does not include so-called ultra-weak light emission, which can be detected in virtually all living structures using sensitive luminometric equipment (Murphy, M. E. and Sies, H. (1990), *Meth. Enzymol* 186, 595-610; Radotic, K, Radenovic, C, Jeremic, M. (1998), *Gen Physiol Biophys* 17, 289-308). Bioluminescence also does not include weak light emissions, which most probably does not play any ecological role, such as the glowing of bamboo growth cone (Totsune, H., Nakano, M., Inaba, H. (1993), *Biochem. Biophys. Res Comm.* 194, 1025-1029). Bioluminescence also does not include emission of light during fertilization of animal eggs (Klebanoff, S. J., Froeder, C. A., Eddy, E. M., Shapiro, B. M. (1979), *J. Exp. Med.* 149, 938-953; Schomer, B. and Epel, D. (1998), *Dev Biol* 203, 1-11).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7);

serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.*, 113: 2722, 1991; Ellman, et al., *Methods Enzymol.*, 202: 301, 1991; Chung, et al., *Science*, 259: 806-9, 1993; and Chung, et al., *Proc. Natl. Acad. Sci. USA*, 90: 10145-9, 1993). In a second method, translation is carried out in *Xenopus* oocytes by microinjection of mutated mRNA and chemically aminoacylated suppressor tRNAs (Turcatti, et al., *J. Biol. Chem.*, 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.*, 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

A DNA "coding sequence" is a DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

A cell has been "transformed" or "transfected" by a nucleic acid sequence such as an exogenous or a heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. The nucleic acid may be in the form of naked DNA or RNA, associated with various proteins or the nucleic acid may be incorporated into a vector.

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of one or more of the above.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, the term "reporter gene" refers to a coding sequence attached to heterologous promoter or enhancer elements and whose product may be assayed easily and quantifiably when the construct is introduced into tissues or cells.

As used herein, the term "hybridization" refers to the process of association of two nucleic acid strands to form an antiparallel duplex stabilized by means of hydrogen bonding between residues of the opposite nucleic acid strands.

The term "immunologically active" defines the capability of the natural, recombinant or synthetic bioluminescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

"Optional" or "optionally" means that the subsequently described circumstance may or may not occur, so that the description includes instances where the circumstance occurs and instances where it does not.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids (e.g., surface bound and solution phase nucleic acids) of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the disclosure can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid is specifically hybridized to a surface bound nucleic acid. Wash conditions used to identify nucleic acids may include (e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions). Stringent conditions for washing can also be (e.g., 0.2×SSC/0.1% SDS at 42° C.).

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "salts" herein refers to both salts of carboxyl groups and to acid addition salts of amino groups of the polypeptides of the present disclosure. Salts of a carboxyl group may be formed by methods known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the present disclosure or their analogs.

The polynucleotides and the vectors can be introduced into cells with different purposes, generating transgenic cells and organisms. A process for producing cells capable of expressing a polypeptide of the present disclosure includes genetically engineering cells with such vectors and nucleic acids.

In particular, host cells (e.g., bacterial cells) can be modified by transformation for allowing the transient or stable expression of the polypeptides encoded by the nucleic acids and the vectors of the present disclosure. Alternatively the molecules can be used to generate transgenic animal cells or non-human animals (by non-/homologous recombination or by any other method allowing their stable integration and maintenance), having enhanced or reduced expression levels of the polypeptides of the present disclosure, when the level is compared with the normal expression levels. Such precise modifications can be obtained by making use of the nucleic acids of the present disclosure and of technologies associated, for example, to gene therapy (Meth. Enzymol., vol. 346, 2002) or to site-specific recombinases (Kolb A F, 2002).

Gene silencing approaches may also be undertaken to down-regulate endogenous expression of a gene encoding a polypeptide of the present disclosure. RNA interference (RNAI) (Elbashir, S M et al., Nature 2001, 411, 494-498) is one method of sequence specific post-transcriptional gene silencing that may be employed. Short dsRNA oligonucleotides are synthesised in vivo and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The polypeptides of the present disclosure can be prepared by any method known in the art, including recombinant DNA-related technologies, and chemical synthesis technologies. In particular, a method for making a polypeptide of the present disclosure may include culturing a host or transgenic cell as described above under conditions in which the nucleic acid or vector is expressed, and recovering the polypeptide encoded by said nucleic acid or vector from the culture. For example, when the vector expresses the polypeptide as a fusion protein with an extracellular or signal-peptide containing proteins, the recombinant product can be secreted in the extracellular space, and can be more easily collected and purified from cultured cells in view of further processing or, alternatively, the cells can be directly used or administered.

The DNA sequence coding for the proteins of the present disclosure can be inserted and ligated into a suitable episomal or non-/homologously integrating vectors, which can be introduced in the appropriate host cells by any suitable means (transformation, transfection, conjugation, protoplast fusion, electroporation calcium phosphate-precipitation, direct microinjection, etc.). Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

The vectors should allow the expression of the isolated or fusion protein including the polypeptide of the disclosure in the prokaryotic or eukaryotic host cells under the control of transcriptional initiation/termination regulatory sequences, which are chosen to be constitutively active or inducible in the host cell. A cell line substantially enriched in such cells can be then isolated to provide a stable cell line.

For eukaryotic hosts (e.g., yeasts, insect plant, or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene, which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells stably transformed by the introduced DNA can be selected by introducing one or more markers allowing the selection of host cells which contain the expression vector. The marker may also provide for prototrophy to an auxotropic host biocide resistance, e.g., antibiotics, or heavy metals such as copper, or the like. The selectable marker gene can either be directly linked to the DNA gene sequences to be expressed, or introduced into the same cell by co-transfection.

Host cells may be either prokaryotic or eukaryotic. Preferred are eukaryotic hosts, e.g., mammalian cells, such as human, monkey, mouse, and Chinese Hamster Ovary (CHO) cells, because they provide post-translational modifications to proteins, including correct folding and glycosylation. Also yeast cells can carry out post-translational peptide modifications including glycosylation. A number of recombinant DNA strategies exist that utilize strong promoter sequences and high copy number of plasmids, which can be utilized for production of the desired proteins in yeast. Yeast recognizes leader sequences in cloned mammalian gene products and secretes peptides bearing leader sequences (i.e., pre-peptides).

"Contacting" means to bring or put together. As such, a first item is contacted with a second item when the two items are brought or put together (e.g., by touching them to each other).

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal.

Discussion

Polypeptides (luciferases) having modulated properties, as well as the polynucleotides encoding the same, are provided. In representative embodiments, the luciferases exhibit at least one of modulated stability, enhanced light output, and modulated emission maximum. Also provided are fragments of the subject polynucleotides and the subject polypeptides encoded thereby, as well as antibodies to the subject polypeptides and transgenic cells and organisms. In addition, fusion proteins including the subject polypeptides or portions thereof and the subject polynucleotides encoding the same are provided. The subject polynucleotide and/or polypeptide compositions find use in a variety of different applications as discussed below. In addition, kits for use in such applications (e.g., kits that include the subject polynucleotide and/or subject polypeptide compositions) are provided.

Embodiments of the present disclosure can be used in systems to detect cellular events, such as, but not limited to, protein-protein interactions, protein dimerization, protein phosphorylation, caspase detection, and/or cellular ion exchange. In addition, the embodiments of the present disclosure can be used to detect (and visualize) and quantitate cellular events in vitro as well as in vivo. Embodiments of the polynucleotides and polypeptides can be used as bioluminescent donor proteins, reporter proteins, split reporter proteins, oxygen sensors, activatable proteins, and the like. Embodiments of the present disclosure can be used in bioluminescence resonance energy transfer (BRET) systems, protein interaction detection systems, systems where the protein is activated by another protein (e.g., caspase or matrix-metalloprotease activatable), the monitoring of gene regulatory systems, and the like.

In further describing the subject disclosure, the subject polynucleotide compositions will be described first, followed by a discussion of the subject polypeptide compositions, antibody compositions, fusion polypeptides, and transgenic cells/organisms. Next a review of representative methods in which the subject proteins find use is provided.

Polynucleotide Compositions

Embodiments of the present disclosure provide mutant polynucleotides (also referred to as nucleic acid or polynucleotide compositions) encoding mutant luciferases (also referred to as "polypeptides"), as well as fragments and homologues of these polypeptides.

As used herein, luciferases refer to oxygenases that catalyze a light emitting reaction, and luciferin refers to a substrate that is catabolized in the reaction by the given luciferase. For instance, bacterial luciferases catalyze the oxidation of flavin mononucleotide (FMN) and aliphatic aldehydes, which reaction produces light. Another class of luciferases, found among marine arthropods, catalyzes the oxidation of *Cypridina* (Vargula) luciferin, and another class of luciferases catalyzes the oxidation of *Coleoptera* luciferin. Thus, luciferase refers to an enzyme or photoprotein that catalyzes a bioluminescent reaction (a reaction that produces bioluminescence). The luciferases, such as *Coleoptera* and *Renilla* luciferases, are enzymes that act catalytically and are unchanged during the bioluminescence generating reaction. The luciferase photoproteins, such as the *aequorin* photoprotein to which luciferin is non-covalently bound, are changed, such as by release of the luciferin, during bioluminescence generating reaction. For purposes herein, reference to luciferase refers to either the photoproteins or luciferases.

In Representative embodiments, the mutant luciferase polynucleotides, encoded by the nucleic acids, are mutants of luciferases that include an α/β-hydrolase fold, where this structure may occur at a position ranging from about residue 50 to about residue 500 (e.g., from about residue 70 to about residue 300 (as numbered from the N-terminal amino acid)). In representative embodiments, the mutant luciferase polynucleotides encoded by the nucleic acids are mutants of luciferases that have a molecular weight which is less than the molecular weight of *Coleoptera* luciferases (e.g., less than about 60 kD, such as less than about 50 kD, less than about 40 kD, and less than about 36 kD). In representative embodiments, the mutant luciferase polynucleotides encoded by the nucleic acids are mutants of luciferases that exhibit a significant level of homology (e.g., from about 30 to 60%, from about 34 to 56%) to a number of different bacterial haloalkane dehalogenases. In representative embodiments, the mutant luciferase polynucleotides encoded by the nucleic acids are mutants of luciferase polynucleotides that employ a coelenterazine as a substrate, where the term coelenterazine refers collectively to native coelenterazine, as well as analogues thereof, where representative coelenterazine analogues of interest include, but are not limited to: benzy-coelenterazine; coelenterazine-cp; coelenterazine-n; bisdeoxycoelenterazine; and the like. Additional details regarding substrates are provided below.

In representative embodiments, the subject luciferase polynucleotides are mutants of wild-type luciferases found in *Cnidarian* species (e.g., an *Anthozoan* species, such as a *Renilla* species (e.g., *Renilla koellikeri*; *Renilla muelleri* and *Renilla reniformis*, where in representative embodiments, the mutant luciferase is a mutant of the *Renilla reniformis* wild-type luciferase)). The subject polynucleotides and the encoded subject polypeptide sequences of the *Renilla reniformis* wild-type luciferase are known and reported in Lorenz et al., Proc. Nat'l Acad. Sci. USA (1991) 88:4438-4442 and also reported in U.S. Pat. No. 6,451,549 as SEQ ID NOS: 1 and 2, the disclosure of which is herein incorporated by reference. In certain embodiments, the subject polynucleotides are mutants of a luciferase encoded by a "humanized" version of the wild-type *Renilla reniformis* luciferase polynucleotide coding sequence, where the luciferase protein encoded therein includes an amino acid substitution at position 2 from threonine (T) to alanine (A) (also called a T2A substitution).

As mentioned above, the subject polynucleotides encode mutant luciferases. The term "mutant" is employed broadly to refer to a protein that differs in some way from a reference wild-type protein, where the subject protein may retain biological properties of the reference wild-type (e.g., naturally occurring) protein, or may have biological properties that differ from the reference wild-type protein. The term "biological property" of the subject proteins includes, but is not limited to, spectral properties, such emission maximum, quantum yield, and brightness (e.g., as compared to the wild-type protein or another reference protein such as firefly luciferase from *P. pyralis*), and the like; in vivo and/or in vitro stability (e.g., half-life); and the like. Mutants of the disclosure include single amino acid changes (point mutations), deletions of one or more amino acids (point-deletions), N-terminal truncations, C-terminal truncations, insertions, and the like.

For purposes of the disclosure, a naturally occurring luciferase is a reference wild type luciferase for a given mutant if the amino acid sequences of the wild-type and the mutant have high identity over at least the length of the mutant (e.g., at least about 90%, at least about 95%, at least about 97%, at least about 98%, at least about 99% or higher) but will not have complete sequence identity in representative embodiments. In representative embodiments, the mutant will be encoded by a polynucleotide that has been derived from a polynucleotide that encodes the reference wild-type protein (e.g., derived from the wild type encoding nucleic acid by a targeted mutagenesis approach) where a first nucleic acid is considered to be derived from a second nucleic acid if, at some time during the development of the first nucleic acid, the second nucleic acid, or at least the sequence information thereof, is used.

Embodiments of the disclosure provide for subject polynucloetides that encode luciferase mutants that retain luciferase activity (e.g., catalyze the conversion of a coelenterazine substrate into a luminescent product in the presence of molecular oxygen). A feature of embodiments of the disclosure is that the subject luciferase mutants encoded by the subject polynucleotide compositions have at least one of the following properties relative to their corresponding reference wild-type nucleic acid: modulated stability; enhanced light output; and modulated emission wavelength maximum. In certain embodiments, the subject mutants include two or more of the above properties (e.g., modulated stability and enhanced brightness, enhanced light output and modulated emission maximum, modulated stability and modulated emission maximum) or include three or more of the above properties (e.g., modulated stability, enhanced light output and modulated emission maximum).

In representative embodiments, the subject mutants encoded by the subject polynucleotides have at least modulated stability as compared to their corresponding reference wild type protein. Specifically, the mutants have at least modulated stability under in vivo conditions as compared to their corresponding reference wild type. For purposes of the present disclosure, modulated stability under in vivo conditions is determined by evaluating the activity of a given mutant and its corresponding reference wild type protein under mammalian (e.g., rat or mouse) serum conditions for a duration of time.

In certain embodiments, a given mutant exhibits enhanced stability, where the magnitude of enhancement may be at least about 50%, at least about 75% at least about 80%, at least about 85%, or more (e.g., by at least about 2-fold or more, by at least about 10-fold or more, by at least about 50-fold or more, by at least about 150-fold more).

In representative embodiments in which the subject polynucleotides encode a mutant of *Renilla* luciferase that exhibits enhanced stability, the encoded mutant may include a point mutation at least one of the following positions: A55; S130; K136, A143; M253, and S287. Specific point mutations of interest include, but are not limited to: A55T; S130A; K136R; A143M, M253L, and S287L (SEQ ID NOS: 3-8). In those embodiments where a C124 mutation (C124A mutation) is present, the encoded mutant typically further includes at least one additional mutation, such as one or more of the above additional point mutations and/or one or more of the light output enhancing and/or emission wavelength maximum modulating mutations described in greater detail below. In certain embodiments, the subject polynucleotides encode a mutant that includes two or more of the above mutations, three or more of the above mutations, four or more of the above mutations, five or more of the above mutations, or even all of the above mutations, where additional mutations may also be present.

In certain embodiments, a given mutant exhibits enhanced lability (i.e., decreased stability), where the magnitude of enhanced lability may be at least about 10%, at least about 25% or more, at least about 50% or more (e.g., by at least about 2-fold or more, by at least about 10-fold or more, by at least about 50-fold or more).

In representative embodiments in which the subject polynucleotides encode a mutant of *Renilla* luciferase that exhibits enhanced lability, the encoded mutant may include a point mutation at least one of the following positions: Q235 and S257. Specific point mutations of interest include, but are not limited to: Q235A and S257G (SEQ ID NOS: 9-10). In certain embodiments, the subject polynucleotides encode a mutant that includes both the above mutations, where additional mutations may also be present.

In representative embodiments, the mutants encoded by the subject polynucleotides exhibit increased light output as compared to their corresponding reference wild type protein. Specifically, the subject mutants have at least enhanced light output with a given coelenterazine substrate as compared to their corresponding reference wild type. For purposes of the present disclosure, increased light output is determined by evaluating at least one of the kinetics and quantum yield of a given mutant using a convenient assay known to those of skill in the art, where specific assays of interest for determining increased light output are described in the Examples below.

In certain embodiments, these subject mutants exhibit at least increased kinetics, where the magnitude of the increase (as compared to a reference wild type protein) is, in representative embodiments, at least about 25%, at least about 50%, at least about 75% or more (e.g., at least about 2-fold or more, at least about 25-fold or more, at least about 50-fold or more, at least about 100-fold or more).

In certain embodiments, these subject mutants exhibit at least increased quantum yield for a given coelenterazine substrate, where the magnitude of the increase (as compared to a reference wild type protein) is, in representative embodiments, at least about 25%, at least about 50%, at least about 75% or more (e.g., at least about 2-fold or more, at least about 25-fold or more, at least about 50-fold or more, at least about 100-fold or more).

In representative embodiments in which the subject polynucleotides encode a mutant of *Renilla* luciferase that exhibits enhanced light output, the encoded mutant may include a point mutation at least one of the following positions: K136; M185, and S287. Specific point mutations of interest include, but are not limited to: K136R, M185V, and S287L (SEQ ID NOS: 3, 11, and 8). In certain embodiments, the subject polynucleotides encode a mutant that includes two or more of the above mutations, such as all of the above mutations, where additional mutations may also be present.

In representative embodiments, the mutants encoded by the subject polynucleotides provide at least a modulated emission wavelength maximum as compared to their corresponding reference wild type protein. Specifically, the mutants provide at a least modulated wavelength maximum for a given coelenterazine substrate as compared to their corresponding reference wild type protein. For purposes of the present disclosure, wavelength emission maximum is determined by any convenient assay known to those of skill in the art, where a specific assay of interest for determining wavelength emission maximum of a given mutant is provided in the Examples below.

In certain embodiments, a given mutant exhibits a blue shifted emission wavelength maximum, by which is meant that the wavelength of the emission maximum is reduced as compared to the reference wild type control, where the magnitude of blue shift may be at least about 5 nm or at least about 10 nm or more (e.g., at least about 15 nm or more and at least about 20 nm or more).

In representative embodiments in which the subject polynucleotides encode a mutant of *Renilla* luciferase that exhibits an emission wavelength maximum shifted to shorter wavelengths of light (blue shifted), the encoded mutant may include a point mutation in the substrate binding pocket (or enzymatic pocket). In certain of these embodiments, the point mutation is at least one of the following positions: N53, A54, D120, W121, V146, F181, and F286. Specific point mutations of interest include, but are not limited to: N53Q, A54P, D120N, W121F, V146I, V146M, F181W, and F286Y (SEQ ID NOS 31-38). In certain embodiments, the subject polynucleotides encode a mutant that includes two or more of the above mutations, three or more of the above mutations, four or more of the above mutations, five or more of the above mutations, six or more of the above mutations, or even all of the above mutations, where additional mutations may also be present.

In representative embodiments in which the subject polynucleotides encode a mutant of *Renilla* luciferase that exhibits shifted wavelength light output, the encoded mutant may include red-shifted mutated *Renilla* Luciferase proteins that have their major radiation peak 15 nm or more toward longer wavelengths than unmutated *Renilla* Luciferase proteins without excessive (where excessive implies a >95% loss) enzymatic activity loss, portions thereof, mutants thereof, variants thereof, conservative variants thereof, and the like. Red shifted emission of photons is advantageous because the longer wavelength photons can penetrate tissue better than shorter wavelength photons.

In representative embodiments in which the subject polynucleotides encode a mutant of *Renilla* luciferase that exhibits shifted wavelength light output, the encoded mutant may include red-shifted mutated *Renilla* Luciferase proteins that have their major radiation peak at least 15 nm or more toward longer wavelengths than unmutated *Renilla* Luciferase proteins without excessive enzymatic activity loss, at least 20 nm or more toward longer wavelengths than unmutated *Renilla* Luciferase proteins without excessive enzymatic activity loss, at least 25 nm or more toward longer wavelengths than unmutated *Renilla* Luciferase proteins without excessive enzymatic activity loss, at least 30 nm or more toward longer wavelengths than unmutated *Renilla* Luciferase proteins without excessive enzymatic activity loss, at least 35 nm or more toward longer wavelengths than unmutated *Renilla* Luciferase proteins without excessive enzymatic activity loss, at least 40 nm or more toward longer wavelengths than unmutated *Renilla* Luciferase proteins without excessive enzymatic activity loss, at least 45 nm or more toward longer wavelengths than unmutated *Renilla* Luciferase proteins without excessive enzymatic activity loss, at least 50 nm or more toward longer wavelengths than unmutated *Renilla* Luciferase proteins without excessive enzymatic activity loss, at least 55 nm or more toward longer wavelengths than unmutated *Renilla* Luciferase proteins, or at least 60 nm or more toward longer wavelengths than unmutated *Renilla* Luciferase proteins.

In representative embodiments in which the subject polynucleotides encode a mutant of *Renilla* luciferase that exhibits shifted wavelength light output, the encoded mutant may include a red-shifted mutated *Renilla* Luciferase protein that has its major radiation peak about 15 to 60 nm more toward longer wavelengths than unmutated *Renilla* Luciferase proteins. In representative embodiments in which the subject polynucleotides encode a mutant of *Renilla* luciferase that exhibits shifted wavelength light output, the encoded mutant may include red-shifted mutated *Renilla* Luciferase proteins that have their major radiation peak about 25 to 50 nm or more toward longer wavelengths than unmutated *Renilla* Luciferase proteins without excessive enzymatic activity loss.

In representative embodiments in which the subject polynucleotides encode a mutant of *Renilla* luciferase that exhibits shifted wavelength light output, the encoded mutant may include a red-shifted mutated *Renilla* Luciferase protein that emits about 5 to 30% of its radiation above 600 nm, about 6 to 23% of its radiation above 600 nm, about 10 to 23% of its radiation above 600 nm, about 15 to 23% of its radiation above 600 nm, or about 20 to 23% of its radiation above 600 nm.

The red-shifted mutated *Renilla* Luciferase proteins can include proteins that have an amino acid-sequence selected from: SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30, portions of each, mutants of each, variants of each, or conservative variants of each.

Table 1 includes some exemplary embodiments of the red-shifted mutated *Renilla* Luciferase proteins.

TABLE 1

| Mutations (SEQ ID NO) | Activity (relative to native *Renilla* luciferase) | Red-shift compared to native *Renilla* luciferase (nm) | % of photons above 600 nm |
|---|---|---|---|
| RLuc8/I159H (18) | 0.05 | 24 | 10 |
| RLuc8/I163Y (19) | 0.17 | 20 | 8 |
| RLuc8/F261W (20) | 0.26 | 22 | 8 |
| RLuc8/F262W (21) | 0.75 | 18 | 7 |
| RLuc8/I223C (22) | 3.9 | 21 | 9 |
| RLuc8/F181Y (23) | 0.09 | 15 | 6 |
| RLuc8/A123S/D162E/I163L (24) | 3.8 | 41 | 12 |
| RLuc8/A123S/D162N/I163L (25) | 3.1 | 25 | 7 |
| RLuc8/A123S/D162E/I163L/V185L (26) | 3.4 | 50 | 15 |
| RLuc8/A123S/D154M/E155G/D162E/I163L/V185L (27) | 6.0 | 53 | 17 |
| RLuc8/A123S/D154K/E155N/D162E/I163L/F261W (28) | 1.9 | 63 | 21 |
| RLuc8/A123S/D154V/E155G/D162E/I163V/F262W (29) | 1.7 | 61 | 21 |
| RLuc8/A123S/D154A/E155G/D162E/I163V/F262W (30) | 1.2 | 65 | 23 |

Note:
RLuc8 is RLuc with the following mutations: A55T, C124A, S130A, K136R, A143M, M185V, M253L, and S287L (SEQ ID NO: 13).

In representative embodiments in which the subject polynucleotides encode a mutant of *Renilla* luciferase that exhibits a red shifted emission wavelength maximum, the encoded mutant may include a point mutation in the substrate binding pocket (or enzymatic pocket). In certain of these embodiments, the point mutation is at least one of the following positions: A123, D154, E155, I159, D162, I163, F181, V185, I223, F261, and/or F262. Specific point mutations of interest include, but are not limited to: A123S, D154A, D154K, D154M, D154V, E155G, E155N, I159F, I159H, I159Y, D162E, D162N, I163H, I163L, I163V, I163W, I163Y, F181Y, M185L, I223C, I223H, I223M, and/or I223Q, F261W, F262W, and F262Y. In certain embodiments, the mutant includes two or more of the above mutations, such as three or more, four or more, five or more, or even all of the above mutations, where additional mutations may also be present as well.

Specific polynucleotides of interest include those polynucleotides that encode the specific mutant luciferases of Renilla luciferase (e.g., Rluc8) (SEQ ID NO: 13).

Subject polynucleotide compositions of the disclosure include compositions that include a sequence of DNA having an open reading frame that encodes a luciferase polypeptide of the subject disclosure, such that the sequence of DNA may be referred to as a luciferase gene, and is capable, under appropriate conditions, of being expressed as a luciferase protein according to the subject disclosure. Also encompassed in this term are polynucleotides that are homologous, substantially similar, or identical to the polynucleotides of the present disclosure. Thus, embodiments of the disclosure provide genes and coding sequences thereof encoding the polynucleotides of the subject disclosure, as well as homologs thereof. The subject polynucleotides, if naturally occurring, are present in other than their natural environment (e.g., they are isolated), and/or present in enriched amounts from their naturally occurring environment (e.g., the organism from which they are obtained). Embodiments of the present disclosure include, but are not limited to, isolated subject polynucleotides, isolated subject polypeptides, isolated subject antibodies, isolated subject cells (e.g., transgenic), and the like.

In addition to the above-described luciferase mutants, additional luciferase mutants that include at least one of modulated stability, enhanced light output, and modulated wavelength emission maximum are also encompassed by the disclosure. In representative embodiments, such mutants or variants have point mutations such as those described above in analogous or corresponding positions of their sequence with respect to the specific positions identified in the above representative mutants. Analogous or corresponding sequence positions to make point mutations in a given protein are readily determined by aligning the enclosed specific mutants and the sequences of the wild-type protein from the species of interest, a consensus sequence, as reported in the experimental section below, to identify appropriate positions for variation.

In addition to the above-described specific subject polynucleotide compositions, also of interest are homologues of the above-sequences. With respect to homologues of the subject polynucleotide, the source of homologous genes may be any species of plant or animal, or the sequence may be wholly or partially synthetic. In certain embodiments, sequence similarity between homologues is at least about 20%, at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, and the like. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, e.g. parameters w=4 and T=17). The sequences provided herein are used for recognizing related and homologous nucleic acids in database searches.

Of particular interest in certain embodiments are subject polynucleotides of substantially the same length as the coding portion of the published cDNA for Renilla reniformis luciferase (where by "substantially the same length" is meant that any difference in length does not exceed about 20 number %, does not exceed about 10 number %, and does not exceed about 5 number %) and having sequence identity to any of these sequences of at least about 90%, at least about 95% and at least about 99% over the entire length of the subject polynucleotide. In many embodiments, the subject polynucleotides have a sequence that is substantially similar or identical to the wild type sequence. By "substantially similar" is meant that sequence identity will generally be at least about 60%, at least about 75%, and at least about 80, 85, 90, or 95%.

Also provided are subject polynucleotides that encode the polypeptide encoded by the above-described subject polynucleotides, but differ in sequence from the above-described nucleic acids due to the degeneracy of the genetic code. Also provided are subject polynucleotides that hybridize to the above-described subject polynucleotide under stringent conditions.

The subject polynucleotides can be generated using any convenient protocol. Mutant polynucleotides can be generated by random mutagenesis or targeted mutagenesis, using well-known techniques that are known in the art. In some embodiments, homologue or mutant polynucleotides encode mutant luciferases with altered spectral properties, as described in more detail herein.

Subject polynucleotides of the subject disclosure may be cDNA of genomic DNA or fragments thereof. In certain embodiments, the subject polynucleotides of the subject disclosure include one or more of the open reading frames encoding specific luciferases, and introns, as well as adjacent 5' and 3' non-coding nucleotide sequences involved in the regulation of expression, up to about 20 kb beyond the coding region, but possibly further in either direction. The subject polynucleotides may be introduced into an appropriate vector for extrachromosomal maintenance or for integration into a host genome, as described in greater detail below.

The term "cDNA" as used herein is intended to include all polynucleotides that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the polypeptide.

A genomic sequence of interest includes the subject polynucleotides present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, and the like, including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The subject polynucleotide compositions may encode all or a part of the subject proteins. Double or single stranded fragments may be obtained from the DNA sequence by chemically synthesizing oligonucleotides in accordance with conventional methods, by restriction enzyme digestion, by PCR amplification. For the most part, DNA fragments will be of at least about 15 nt, at least about 18 nt or about 25 nt, and at least about 50 nt. In some embodiments, the polynucleotide molecules may be about 100 nt, about 200 nt, about 300 nt, about 400 nt, about 500 nt, about 600 nt, about 700 nt, or about 720 nt in length. The subject polynucleotides may encode fragments of the polypeptides or the full-length polypeptides (e.g., the subject polynucleotides may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein). In representative embodiments, polynucleotides of interest include at least a sufficient amount of the parent nucleic acid to retain at least some luciferase activity, such that the fragment encodes a product that has luciferase activity.

In representative embodiments, the subject polynucleotides are isolated and obtained in substantial purity, generally as other than an intact chromosome. Usually, the DNA will be obtained substantially free of other polynucleotide sequences that do not include a polynucleotides or fragment thereof, generally being at least about 50% to at least about 90% pure or more and are typically "recombinant" (e.g., flanked by one or more nucleotides with which it is not normally associated on a naturally occurring chromosome).

The polynucleotides of the corresponding cDNA, the full-length gene, and constructs of the subject polynucleotides are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual,* 2nd Ed., (1989) Cold Spring Harbor Press, Cold Spring Harbor, N.Y., and under current regulations described in United States Dept. of HHS, National Institute of Health (NIH) Guidelines for Recombinant DNA Research, which are both incorporated herein by reference.

Also provided are polynucleotides that encode fusion proteins of the subject polypeptides, or fragments thereof, which are fused to a second protein (e.g., a degradation sequence, a signal peptide, an antibody or binding fragment/mimetic thereof, and a ligand of interest). As such, fusion proteins may include a subject polypeptide, or fragment thereof, and a non-*Anthozoan* polypeptide ("the fusion partner") fused in-frame at the N-terminus and/or C-terminus of the subject polypeptide. Fusion partners include, but are not limited to, polypeptides that can bind antibodies specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject luciferase portion of the fusion protein, and is typically not a luciferase protein or derivative/fragment thereof (e.g., it is not found in *Cnidarian* or at least *Anthozoan* species).

In certain embodiments, the fusion partner of a fusion protein of the subject disclosure is a targeting moiety, where by "targeting moiety" is meant a moiety that binds specifically to a target molecule of interest. The target molecule of interest can be any of a number of molecules, including but not limited to, a protein/polypeptide, a carbohydrate, a lipid, or a nucleic acid. In certain embodiments, the targeting moiety is specific for a target molecule that is present on the surface of a cell of interest (e.g., a cell surface moiety). In some of these embodiments, the cell surface moiety to which the targeting moiety binds is a cell surface expressed protein. For example, if the cell surface protein of interest is a receptor that binds specifically to a ligand, then a targeting moiety of a fusion protein of the present disclosure could be that ligand (or the receptor-binding portion thereof). As is evident to one of skill in the art, targeting moieties that find use in the fusion proteins of the of the present disclosure can be specific for a wide variety of molecules present on the surface of a cell for which a specific binding partner is known, and as such, no limitation in this regard is intended.

Also provided are constructs that include the subject polynucleotides inserted into a vector, where such constructs may be used for a number of different applications, including propagation, protein production, and the like. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the disclosure is expressed in any convenient expression system, including, for example, bacterial, yeast, insect, amphibian and mammalian systems. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared including a transcription initiation region, the gene or fragment thereof, and a transcriptional termination region. Of particular interest is the use of sequences that allow for the expression of functional epitopes or domains of the encoded polypeptide, usually at least about 8 amino acids in length, at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional uses, depending upon the purpose for expression. For large scale production of the protein, a unicellular organism, such as E. coli, B. subtilis, S. cerevisiae, insect cells in combination with baculovirus vectors, or cells of a higher organism such as vertebrates (e.g., COS 7 cells, HEK 293, CHO, Xenopus Oocytes, and the like) may be used as the expression host cells. In some situations, it is desirable to express the gene in eukaryotic cells, where the expressed protein will benefit from native folding and post-translational modifications. Specific expression systems of interest include bacterial, yeast, insect cell and mammalian cell derived expression systems. Small peptides can also be synthesized in the laboratory. Polypeptides that are subsets of the complete protein sequence may be used to identify and investigate parts of the protein important for function.

When any of the above host cells, or other appropriate host cells or organisms, are used to replicate and/or express the polynucleotides or nucleic acids of the disclosure, the resulting replicated nucleic acid, RNA, expressed protein or polypeptide, is within the scope of the disclosure as a product of the host cell or organism. The product is recovered by any appropriate means known in the art.

Also provided are homologs of the polynucleotides. Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, they can hybridize at 50° C. and 6×SSC (0.9 M sodium chloride/0.09 M sodium citrate), and remain bound when subjected to washing at 55° C. in 1×SSC (0.15 M sodium chloride/0.015 M sodium citrate). Sequence identity may be determined by hybridization under stringent conditions, for example at 50° C. or higher and 0.1×SSC (15 mM sodium chloride/1.5 mM sodium citrate). Nucleic acids having a region of substantial identity to the provided sequences (e.g., allelic variants, genetically altered versions of the gene, and the like) bind to the provided sequences under stringent hybridization conditions. By using probes, particularly labeled probes of DNA sequences, one can isolate homologous or related genes.

Also provided are small DNA fragments of the subject polynucleotides, which fragments are useful as primers for PCR, hybridization screening probes, and the like. Larger DNA fragments (e.g., greater than 100 nt) are useful for production of the encoded polypeptide, as described herein. For use in geometric amplification reactions, such as geometric PCR, a pair of primers will be used. The exact composition of the primer sequences is not critical to the disclosure, but for most applications the primers will hybridize to the subject sequence under stringent conditions, as known in the art. It is preferable to choose a pair of primers that will generate an amplification product of at least about 50 nt and at least about 100 nt. Algorithms for the selection of primer sequences are generally known, and are available in commercial software packages. Amplification primers hybridize to complementary strands of DNA, and will prime towards each other.

The subject polynucleotides, including flanking promoter regions and coding regions, may be mutated in various ways known in the art to generate targeted changes in promoter strength, sequence of the encoded protein, properties of the encoded protein, including bioluminescent properties of the encoded protein, and the like. The DNA sequence or protein product of such a mutation will usually be substantially similar to the sequences provided herein (e.g. will differ by at least one nucleotide or amino acid, respectively) and may differ by at least two but not more than about ten nucleotides or amino acids. The sequence changes may be substitutions, insertions, deletions, or a combination thereof. Deletions may further include larger changes, such as deletions of a domain or exon (e.g., of stretches of 10, 20, 50, 75, 100, 150 or more aa residues). Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated nucleic acid derivatives may be used to study structure-function relationships of a particular bioluminescent protein, or to alter properties of the protein that affect its function or regulation.

Also of interest are humanized versions of the subject polynucleotides. As used herein, the term "humanized" refers to changes made to the nucleic acid sequence to optimize the codons for expression of the protein in human cells (Yang et al., *Nucleic Acids Research* 24 (1996), 4592-4593). See also U.S. Pat. No. 5,795,737 that describes humanization of proteins, the disclosure of which is herein incorporated by reference.

Protein/Polypeptide Compositions

Embodiments of the present disclosure include mutant luciferase polypeptides (also called "subject polypeptides" that are encoded by the subject polynucleotides described herein), as well as subject polypeptide compositions related thereto. The terms polypeptide, protein, and polypeptide composition as used herein refer to the full-length protein as well as portions or fragments thereof. Also included in these terms are variations of the naturally occurring protein, where such variations are homologous or substantially similar to the naturally occurring protein, and mutants of the naturally occurring proteins, as described in greater detail below. The subject polypeptides are present in other than their natural environment. Features of embodiments of the mutant luciferase polypeptides are described above in reference to the subject polynucleotides.

Homologs or polypeptides (or fragments thereof) that vary in sequence from amino acid sequences of the above specified mutants of the subject disclosure are also provided. By homolog is meant a polypeptide having at least about 10%, at least about 20% and at least about 30%, and in many embodiments at least about 35%, at least about 40%, at least about 60%, at least about 65%, at least about 70%, at least about 75%, at least about 80%, at east about 85%, and at least about 90% or higher, amino acid sequence identity to the peptide of the subject disclosure, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153, which is hereby incorporated by reference. (Parameters used are ktuple 1, gap penalty 3, window, 5 and diagonals saved 5).

Also provided are polypeptides that are substantially identical to the specifically described subject polypeptides herein, where by substantially identical is meant that the polypeptide has an amino acid sequence identity to the subject polypeptide of at least about 60%, at least about 65%, at least about 70%, at least about 75%, at least about 80%, at least about 85%, at least about 90%, and at least about 95%, where in some instances the identity may be higher.

In representative embodiments, the subject homologues have structural features found in the above provided specific sequences, where such structural features include the α/β-hydrolase fold; a size that does not exceed about 40 kD, and the like.

Proteins that are mutants of the specifically described subject proteins herein are also provided. Mutants may retain biological properties of the parent (e.g., naturally occurring) proteins, or may have biological properties that differ from the wild-type proteins. The term "biological property" of the subject proteins includes, but is not limited to, spectral properties, such as absorbance maximum, emission maximum, maximum extinction coefficient, brightness of the product produced by the activity of the mutant, and the like; in vivo and/or in vitro stability (e.g., half-life); and the like. Mutants include single amino acid changes, deletions of one or more amino acids, N-terminal truncations, C-terminal truncations, insertions, and the like.

Mutants can be generated using standard techniques of molecular biology (e.g., random mutagenesis and targeted mutagenesis). Several mutants are described herein. Given the guidance provided in the Examples, and using standard techniques, those skilled in the art can readily generate a wide variety of additional mutants and test whether a biological property has been altered. For example, luminescence intensity can be measured using a spectrophotometer at various emission wavelengths.

The subject polypeptides of the present disclosure that are naturally occurring proteins are present in a non-naturally occurring environment (e.g., are separated from their naturally occurring environment). In certain embodiments, the subject proteins are present in a composition that is enriched for the subject protein as compared to its naturally occurring environment. For example, purified protein is provided, where by "purified" is meant that the protein is present in a composition that is substantially free of non-chromo/fluoro-protein proteins of interest, where by "substantially free" is meant that less than 90%, less than 60%, and/or less than 50% of the composition is made up of non-luciferase mutants of interest. The polypeptides of the subject disclosure may also be present as an isolate, by which is meant that the polypeptide is substantially free of other proteins and other naturally occurring biologic molecules, such as oligosaccharides, polynucleotides and fragments thereof, and the like, where the term "substantially free" in this instance indicates that less than 70%, less than 60%, and/or less than 50% of the composition containing the isolated protein is some other naturally occurring biological molecule. In certain embodiments, the proteins are present in substantially pure form, where by "substantially pure form" is meant at least 95%, at least 97%, and at least 99% pure.

In addition to the specifically described subject polypeptides, polypeptides that vary from these subject polypeptides (e.g., the mutant proteins described above) are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, at least about 50 aa in length, and may be as long as 300 aa in length or longer, but will usually not exceed about 1000 aa in length, where the fragment will have a stretch of amino acids that is identical to the subject protein of at least about 10 aa, and at least about 15 aa, and in many embodiments at least about 50 aa in length. In some embodiments, the subject polypeptide fragments are about 25 aa, about 50 aa, about 75 aa, about 100 aa, about 125 aa, about 150 aa, about 200 aa, about 210 aa, about 220 aa, about 230 aa, or about 240 aa in length, up to the entire polypeptide. In some embodiments, a polypeptide fragment retains all or substantially all of a biological property of the wild-type protein.

The subject proteins and polypeptides may be obtained from naturally occurring sources or synthetically produced. For example, wild type proteins may be derived from biological sources that express the proteins (e.g., bioluminescent Cnidarian, e.g., Anthozoan, species) such as the specific sources listed above. The subject polypeptides may also be derived from synthetic methods (e.g., by expressing a recombinant gene or nucleic acid coding sequence encoding the protein of interest in a suitable host) as described above. Any convenient protein purification procedures may be employed, where suitable protein purification methodologies are described in Guide to Protein Purification, (Deuthser ed.) (Academic Press, 1990). For example, a lysate may be prepared from the original source and purified using HPLC, exclusion chromatography, gel electrophoresis, affinity chromatography, and the like.

Antibody Compositions

Also provided are antibodies that specifically bind to the subject bioluminescent proteins. Suitable antibodies are obtained by immunizing a host animal with peptides comprising all or a portion of the subject protein(s). Suitable host animals include, but are not limited to, mouse, rat sheep, goat, hamster, and rabbit. The origin of the protein immunogen will generally be a Cnidarian species, specifically an Anthozoan species, such as a Renilla species. The host animal will generally be a different species than the immunogen (e.g., mice).

The immunogen may include the complete polypeptide, or fragments and derivatives thereof. Preferred immunogens comprise all or a part of the polypeptide, where these residues contain the post-translation modifications found on the native target protein. Immunogens are produced in a variety of ways known in the art (e.g., expression of cloned genes using conventional recombinant methods, isolation from Anthozoan species of origin, and the like).

For preparation of polyclonal antibodies, the first step is immunization of the host animal with the target polypeptide, where the target polypeptide will preferably be in substantially pure form, e.g., including less than about 1% contaminant. The immunogen may include the complete target polypeptide, of fragments or derivatives thereof. To increase the immune response of the host animal, the target polypeptide may be combined with an adjuvant, where suitable adjuvants include alum, dextran, sulfate, large polymeric anions, oil & water emulsions (e.g., Freund's adjuvant, Freund's complete adjuvant, and the like). The target polypeptide may also be conjugated to synthetic carrier proteins or synthetic antigens. A variety of hosts may be immunized to produce the polyclonal antibodies. Such hosts include, but are not limited to, rabbits, guinea pigs, and rodents (e.g., mice, rats, sheep, goats, and the like). The target polypeptide is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques known to those of skill in the art. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include, but are not limited to, mouse, rat, hamster, and the like. To raise antibodies against the mouse protein, the animal will generally be a hamster, guinea pig, rabbit, and the like. The antibody may be purified from the hybridoma cell supernatants or ascites fluid by conventional techniques (e.g., affinity chromatography using protein bound to an insoluble support, protein A sepharose, and the like).

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036), which are incorporated herein by reference. Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521, which are incorporated herein by reference). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242, which is incorporated herein by reference. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa, or lambda, may be used. The chimeric, humanized antibody is then expressed by conventional methods.

Antibody fragments, such as Fv, F(ab')$_2$ and Fab may be prepared by cleavage of the intact protein (e.g., by protease or chemical cleavage). Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design polynucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, and the like.

Transgenics

The polypeptides can be used to generate transgenic, non-human plants or animals or site specific gene modifications in cell lines. Transgenic cells of the subject disclosure include one or more polypeptides according to the present disclosure present as a transgene, where included within this definition are the parent cells transformed to include the transgene and the progeny thereof. In many embodiments, the transgenic cells are cells that do not normally harbor or contain the polypeptides according to the present disclosure. In those embodiments where the transgenic cells do naturally contain the subject polypeptides, the subject polypeptides will be present in the cell in a position other than its natural location (e.g., integrated into the genomic material of the cell at a non-natural location). Transgenic animals may be made through homologous recombination, where the endogenous locus is altered. Alternatively, a polypeptide construct is randomly integrated into the genome. Vectors for stable integration include plasmids, retroviruses and other animal viruses, YACs, and the like.

Transgenic organisms of the subject disclosure include cells and multicellular organisms (e.g., plants and animals) that are endogenous knockouts in which expression of the endogenous gene is at least reduced if not eliminated. Transgenic organisms of interest also include cells and multicellular organisms (e.g., plants and animals) in which the protein or variants thereof is expressed in cells or tissues where it is not normally expressed and/or at levels not normally present in such cells or tissues.

DNA constructs for homologous recombination include at least a portion of the gene of the present disclosure, where the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537, which is incorporated herein by reference.

For embryonic stem (ES) cells, an ES cell line may be employed, or embryonic cells may be obtained freshly from a host (e.g., mouse, rat, guinea pig, and the like). Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, and the like. The transgenic animals may be used in functional studies, drug screening, and the like. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275-295. In brief, a suitable plant cell or tissue is harvested, depending on the nature of the plant species. As such, in certain instances, protoplasts will be isolated, where such protoplasts may be isolated from a variety of different plant tissues (e.g., leaf, hypoctyl, root, and the like). For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arises for introduction via DNA-mediated gene transfer protocols, including: incubation of the protoplasts with naked DNA (e.g., plasmids) including the exogenous coding sequence of interest in the presence of polyvalent cations (e.g., PEG or PLO); and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors (e.g., auxins and cytokinins). With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain (e.g., *A. tumefaciens*). The resultant bacteria are then incubated with prepared protoplasts or tissue explants (e.g., leaf disks, and a callus is produced). The callus is then grown under selective conditions, selected, and subjected to growth media to induce root and shoot growth to ultimately produce a transgenic plant.

Methods of Use

The luciferase mutants (subject polynucleotides encoding the mutants and the subject polypeptides) find use in a variety of different applications. Representative uses are described below, where the following described uses are merely representative and are in no way meant to limit the use of the subject polypeptides to those described below.

The subject polynucleotides and polypeptides of the present disclosure (as well as other components of the subject disclosure described above) find use in a variety of different applications, where such applications include, but are not limited to, the following.

One representative application of interest is the use of the subject polypeptides in bioluminescence resonance energy transfer (BRET) applications. The present disclosure provides for subject polypeptides, subject polynucleotides, a bioluminescence initiating compound, and the like, that can be used for studying (e.g., detecting, localizing, or quantifying) protein-protein interactions inside a host living cell, tissue, or organ, or a host living organism sing the one or methods. In these applications, the subject proteins serve as donor and/or acceptors in combination with a second fluorescent protein or dye (e.g., a fluorescent protein as described in Matz et al., Nature Biotechnology (October 1999) 17:969-973; a green fluorescent protein from *Aequoria victoria* or fluorescent mutant thereof (e.g., as described in U.S. Pat. Nos. 6,066, 476; 6,020,192; 5,985,577; 5,976,796; 5,968,750; 5,968,738; 5,958,713; 5,919,445; 5,874,304, the disclosures of which are herein incorporated by reference); and other fluorescent dyes, e.g., coumarin and its derivatives (e.g. 7-amino-4-methylcoumarin, aminocoumarin), bodipy dyes such as Bodipy FL, cascade blue, fluorescein and its derivatives (e.g., fluorescein isothiocyanate), Oregon green, rhodamine dyes (e.g., texas red, tetramethylrhodamine), eosins and erythrosins, cyanine dyes (e.g., Cy3 and Cy5), macrocyclic chelates of lanthanide ions (e.g., quantum dye, etc.), and chemilumescent dyes, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where BRET assays employing the subject luciferases may be used include, but are not limited to: the detection of protein-protein interactions (e.g., mammalian two-hybrid system, transcription factor dimerization, membrane protein multimerization, multiprotein complex formation, etc.), and as a biosensor for a number of different events where a peptide or protein covalently links a BRET fluorescent combination including the subject fluorescent proteins and where the linking peptide or protein is, e.g., a protease specific substrate (e.g., for caspase mediated cleavage), a linker that undergoes conformational change upon receiving a signal that increases or decreases BRET (e.g., PKA regulatory domain (cAMP-sensor), phosphorylation, e.g., where there is a phosphorylation site in the linker, or the linker has binding specificity to the phosphorylated/dephosphorylated domain of another protein, or the linker has $Ca^{2+}$ binding domain). Representative BRET applications in which the subject proteins find use include, but are not limited to, those described in: U.S. Pat. Nos. 6,436,682 and 6,232,107; as well as published U.S. Patent Application Publication Nos. 20040214227; 20030203404 and 20030092098; the disclosures of which are herein incorporated by reference.

The luciferase polypeptides also find use in applications involving the automated screening of arrays of cells expressing luciferase reporting groups by using microscopic imaging and electronic analysis. Screening can be used for drug discovery and in the field of functional genomics: e.g., where the subject polypeptides are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, and the like.

The subject luciferase polypeptides also find use in high through-put screening assays. For example, polypeptides according to the subject disclosure can be fused with a putative proteolytic signal sequence derived from a protein with shorter half-life, e.g., PEST sequence from the mouse ornithine decarboxylase gene, mouse cyclin B1 destruction box, and ubiquitin. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject luciferase proteins for drug screening (e.g., AP1, NFAT, NF-kB, Smad, STAT, p53, E2F, Rb, myc, CRE, ER, GR and TRE, and the like).

The subject polypeptides can be used as second messenger detectors, e.g., by fusing the subject proteins to specific domains: e.g., PKCgamma Ca binding domain, PKCgamma DAG binding domain, SH2 domain, and SH3 domain.

Secreted forms of the subject polypeptides can be prepared, e.g. by fusing secreted leading sequences (e.g., as described in published United States Patent Application 20020081644, the disclosure of which is herein incorporated by reference) to the subject polypeptides to construct secreted forms of the subject proteins, which in turn can be used in a variety of different applications.

The subject polypeptides also find use as in vivo markers in animals (e.g., transgenic animals). For example, expression of the subject protein can be driven by tissue specific promoters, where such methods find use in research for gene therapy, e.g., testing efficiency of transgenic expression, among other applications.

Additional applications of the subject polypeptides include, but are not limited to: as markers following injection into cells or animals and in calibration for quantitative measurements (luminescence and protein); as markers or reporters in oxygen biosensor devices for monitoring cell viability; as markers or labels for animals, pets, toys, food, and the like.

The subject polypeptides also find use in protease cleavage assays. For example, cleavage inactivated luminescence assays can be developed using the subject proteins, where the subject proteins are engineered to include a protease specific cleavage sequence without destroying the luminescent character of the protein. Upon cleavage of the protein by an activated protease, luminescence would sharply decrease due to the destruction of a functional active site. Alternatively, cleavage activated luminescence can be developed using the subject polypeptides, where the subject proteins are engineered to contain an additional spacer sequence in close proximity/or inside the active site. This variant would be significantly decreased in its activity, because parts of the functional active site would be divided by the spacer. The spacer would be framed by two identical protease specific cleavage sites. Upon cleavage via the activated protease the spacer would be cut out and the two residual "subunits" of the protein would be able to reassemble to generate a functional protein. Cleavage activated luminescence could also be developed using the subject proteins, where the subject proteins are engineered to contain another protein on either terminus, with a protease cleavage site in the linker between the two proteins. Fusions to the n-terminus of the subject proteins in particular can result in large decreases in the enzymatic activity of the subject proteins. Cleavage at the protease specific cleavage site contained within the linker would split the fusion protein, releasing the subject proteins and allowing them to regain full activity. All of the above types of applications could be developed in assays for a variety of different types of proteases (e.g., caspases).

The subject polypeptides also find use in marking and/or identifying specific cell types in vitro and in vivo. For example, fusion proteins between a luciferase of the subject disclosure and a fusion partner that is a targeting moiety specific for a cell surface molecule (as described above in the Nucleic Acids section), can be contacted to the cells to be assayed/screened under conditions that allow binding of the targeting moiety to the target cell surface molecule (e.g., via specific interaction between the fusion partner and the target cell surface molecule). For in vitro analysis, the fusion protein can be contacted to the cells by introducing it into the culture media. For in vivo analysis, the fusion protein can be injected into the subject to the site of interest (e.g., intravenously or into a tissue or anatomical location of interest). Binding of the fusion protein to the cells can then be visualized by providing a luciferase substrate (e.g., coelenterazine) to the cells and spatially detecting the photon emission pattern, even in whole animals. In this way, the presence and/or location of cells that express a specific cell surface molecule can be assayed.

In certain embodiments, the cell surface molecule for which a targeting moiety of a fusion protein is specific is associated with a cellular phenotype of interest. For example, the cell surface molecule of interest might be associated with neoplastic, pre-neoplastic or metastatic cancer cells (e.g., receptors that promote angiogenesis, as described in the Experimental section below), with specific growth potential of a cell (e.g., a receptor that transduces growth signals), or with a specific developmental stage of a cell (e.g., effector T cells).

Additional utilities of the subject mutant luciferases include, but are not limited to, those described in Published U.S. Patent Application Ser. Nos. 20050186606; 20050152838; 20050112576; 20050112551; 20050095583; 20040219622; 20040214227; 20040209274; 20040209246; 20040197855; 20040171099; 20040137454; 20040121365; 20040096924; 20040002123; 20030219723; 20030203404; 20030186313; 20030153090; 20030092098; 20030066096; 20030059798; 20020192726; 20020150912; 20020090659; 20020081644; as well as in U.S. Pat. Nos. 6,451,549; 6,436,682; 6,232,107; 6,228,604; 5,418,155 and 5,292,658; the disclosures of which are herein incorporated by reference.

The antibodies of the subject disclosure, described above, also find use in a number of applications, including the differentiation of the subject proteins from other bioluminescent proteins.

Bioluminescence Initiating Compound

The subject polypeptides can be used in conjunction with a bioluminescence initiating compound to produce a radiation emission. The bioluminescence initiating compound can include, but is not limited to, coelenterazine, analogs thereof, and functional derivatives thereof. Derivatives of coelenterazine include, but are not limited to, bisdeoxycoelenterazine (also known as coelenterazine 400a, coelenterazine-hh, and deep blue coelenterazine (DBC)), benzyl-coelenterazine (also known as coelenterazine-h), coelenterazine-cp, coelenterazine-f, coelenterazine-fcp, coelenterazine-hcp, coelenterazine-ip, coelenterazine-n, coelenterazine-o, coelenterazine-i, coelenterazine-icp, and coelenterazine 2-methyl (described in more detail in U.S. Pat. Nos. 6,020,192; 5,968,750 and 5,874,304).

In general, coelenterazines are known to luminesce when acted upon by a wide variety of bioluminescent proteins, specifically Luciferases. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997, which is incorporated herein by reference.

Kits

Also provided by the subject disclosure are kits for use in practicing one or more of the above described applications, where the subject kits typically include elements for making the subject polypeptides, e.g., a construct comprising a vector that includes a coding region for the subject polypeptide. The subject kit components are typically present in a suitable storage medium, e.g., buffered solution, typically in a suitable container. Also present in the subject kits may be antibodies to the subject polypeptide. In certain embodiments, the kit comprises a plurality of different vectors each encoding the subject polypeptide, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression.

In representative embodiments, the kits further include a substrate for the luciferase, where in representative embodiments the substrate is a coelenterazine. As reviewed above, the term coelenterazine refers collectively to native coelenterazine, as well as analogues thereof, where representative coelenterazine analogues of interest include, but are not limited to coelenterazine; coelenterazine-cp; coelenterazine-n; and bisdeoxycoelenterazine.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert. Yet another form would be a computer readable medium, e.g., diskette, CD, and the like, on which the information has been recorded. Yet another form that may be present is a website address which may be used via the internet to access the information at a removed site. Any convenient form of instructions may be present in the kits.

EXAMPLES

Now having described the embodiments of the of the present disclosure, in general, examples 1 and 2 describe some additional embodiments of the of the present disclosure. While embodiments of the present disclosure are described in connection with examples 1 and 2 and the corresponding text and figures, there is no intent to limit embodiments of the present disclosure to these descriptions. On the contrary, the intent is to cover all alternatives, modifications, and equivalents included within the spirit and scope of embodiments of the present disclosure. Examples 1 and 2 are attached to this document. In addition, each of the references described in the Examples are hereby included by reference.

Example 1

Generation and Functional Analysis of *Renilla* Luciferase Mutants

Materials and Methods
Coelenterazine

Coelenterazine was from Prolume (Pinetop, Ariz.). Benzyl-coelenterazine (coelenterazine-h) was a generous gift from Dr. Bruce Bryan. Coelenterazine-n and coelenterazine-cp were from Biotium (Hayward, Calif.). Bisdeoxycoelenterazine (coelenterazine-400a, di-dehydro coelenterazine, DeepBlueC) was from Perkin Elmer (Boston, Mass.). The chemical structures of these compounds are shown in FIG. 1. Coelenterazine and the analogs were dissolved in propylene glycol and stored in small aliquots at −80° C.

Luminometer Calibration

Light measurements were made using a Turner 20/20 and later a Turner 20/20n luminometer (Turner Designs, Sunnyvale, Calif.). The luminometers were calibrated to absolute units (photons/s) using the luminol light standard performed in dimethyl sulfoxide (DMSO) (Lee, J., Wesley, A. S., Ferguson, J. F., III, and Seliger, H. H. (1966) in Bioluminescence in Progress (Johnson, F. H. and Haneda, Y., eds.), pp. 35-43, Princeton, N.J.; O'Kane, D. J. and Lee, J. (2000) Methods Enzymol. 305, 87-96). No corrections were applied for the spectral sensitivity of the luminometer, as the spectral peak of luminol chemiluminescence in DMSO (486 nm) is close to the spectral peak of *Renilla* luciferase bioluminescence (482 nm).

Computational Prediction

A PSI-BLAST search (Altschul, S. F., Madden, T. L., Schäffer, A. A., Zhang, J., Zhang, Z., Miller, W., and Lipman, D. J. (1997) Nucl. Acids Res. 25, 3389-3402), performed using the PredictProtein server (Rost, B. and Liu, J. (2003) Nucl. Acids Res. 31, 3300-3304), identified a number of sequences homologous to RLuc. An alignment between RLuc and the 9 most similar sequences (46% similarity) was then generated using CLUSTAL W (Thompson, J. D., Higgins, D. G., and Gibson, T. J. (1994) Nucl. Acids Res. 22, 4673-4680).

A homology model of RLuc was built with SWISS-MODEL (v3.5) (Schwede, T., Kopp, J., Guex, N., and Peitsch, M. C. (2003) Nucl. Acids Res. 31, 3381-3385) using the default parameters (FIG. 4(a)). In generating this homology model, SWISS-MODEL utilized several crystal structures of the haloalkane dehalogenase LinB from *Sphingomonas paucimobilis* (PDB files 1iz8, 1k63, 1k6e, 1iz7, and 1mj5).

Construction of *Renilla* Luciferase Mutants

The hrluc gene from the plasmid phRL-CMV (Promega, Madison, Wis.) was used as the initial template for cloning. This gene is a human codon useage optimized version of rluc, and encodes a protein identical to RLuc with the exception of a T2A substitution. To construct a bacterial expression plasmid, CR was used to remove the stop codon and to replace the N-terminal methionine codon with a pelB leader sequence. The pelB leader sequence, consisting of the first 22 codons of the pectate lyase B gene from *Erwinia carotovora* (Lei, S. P., Lin, H. C., Wang, S. S., Callaway, J., and Wilcox, G. (1987) J. Bacteriol. 169, 4379-4383), directs protein expression into the bacterial periplasm and is cleaved from the final protein product. Using NcoI and HindIII restriction sites, the PCR product was inserted into the pBAD/Myc-His A plasmid (Invitrogen, Carlsbad, Calif.), which adds a Myc epitope, a 6×His tag, and a stop codon to the C-terminus of the gene. In some later constructs, the plasmid's SalI site was used for insertion in order to remove the Myc epitope from the construct. Site directed mutagenesis was performed using a QuikChange II XL kit (Stratagene, La Jolla, Calif.). All constructs and mutations were confirmed by sequencing.

Protein Production and Purification

Protein was produced in *E. coli* LMG 194 cells grown at 32° C. in Terrific Broth. Cultures were allowed to reach an $OD_{600}$ of 0.7 and were then induced by addition of L-(+)-Arabinose to a final concentration of 0.2%. 12-14 hours later, cells were harvested and the periplasm extracted by osmotic shock (Neu, H. C. and Heppel, L. A. (1965) J. Biol. Chem. 240, 3685-3692).

Figure 2:
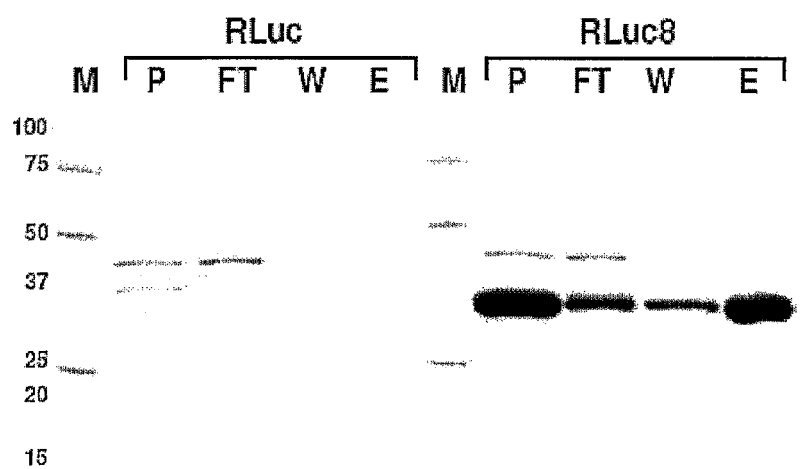
FIG. 2 illustrates a coomassie stained SDS-PAGE gel of RLuc and RLuc8 at several points during the purification process. The lanes are labeled as follows: M—Marker, P—Periplasmic fraction, FT—Flow through from nickel affinity column, W—Wash from column, E—Elution from column. As the elution volume is 5% of the periplasmic fraction, the periplasmic fraction, flow through, and wash were concentrated twenty fold using 3 kDa cut-off centrifugal concentrators (Pall, Ann Arbor, Mich.). The expected sizes for RLuc and RLuc8 are 38.7 kDa and 36.9 kDa, respectively, with the difference in size arising from a Myc epitope added by the expression vector used for RLuc. These protein masses were confirmed by MALDI-TOF. Final recovery of purified protein was typically 5 mg/L of culture for RLuc, and 50 mg/L of culture for RLuc8.

The periplasmic fraction was brought to the same concentration as the wash buffer (WB: 300 mM NaCl, 20 mM HEPES, 20 mM imidazole, pH 8) using a 10× stock, and Phenylmethylsulphonylfluoride was added to 1 mM. The solution was clarified by 0.2 mm filtration and ran over a nickel affinity column (Ni-NTA Superflow, Qiagen, Valencia, Calif.). The column was washed with WB and eluted with elution buffer (EB: 300 mM NaCl, 20 mM HEPES, 250 mM imidazole, pH 8). Protein concentration measurements were made using the Bradford assay (Bradford, M. (1976) Anal. Biochem. 72, 248-254) with human serum albumin (HSA: Baxter Healthcare Corporation, Glendale, Calif.) as the standard. Aliquots were taken at this point for gel electrophoresis (FIG. 2). To the remainder of the elution, HSA was added to 1% as a carrier protein. All samples were stored at 4° C.

Characterization of *Renilla* Luciferase Mutants

Luciferase activity was measured by adding 1 ml of sample (diluted as necessary in EB containing 1% HSA) to 100 ml room temperature 100 mM sodium phosphate buffer (pH 7) (Sørensen, S. P. L. (1909) *Biochem*. 2. 22, 6), manually adding 1 ml of 0.5 mg/ml coelenterazine or analog, manually mixing, and reading for 10 s in a luminometer. The time between the addition of the luciferin and the start of measurement was approximately 4 s.

Serum stability measurements were done by mixing 0.5 ml dilute luciferase with either 20 ml mouse serum or 50 ml rat serum (Equitech-Bio, Kerrville, Tex.), placing the sample in a 37° C. incubator, and removing aliquots for activity testing. To calculate serum half-lives, mono-exponential decay curves were fit to the serum stability data using a Nelder/Mead Simplex non-linear least squares minimization algorithm provided by the Octave numerical programming language. Emission spectra at ambient temperature were measured using a Triax 320 (Horiba Jobin Yvon, Edison, N.J.), which incorporates an optical grating device with a liquid $N_2$ cooled CCD detector.

Protein size and monodispersity was confirmed using a Superdex 200 analytical grade gel filtration column (GE/Amersham Biosciences, Piscataway, N.J.) followed by in-line multiangle light scattering and refractive index detectors (DAWN EOS and Optilab DSP, Wyatt Technologies, Santa Barbara, Calif.). A dn/dc value of 0.185 mL/g was assumed in all calculations, and all processing was performed using the ASTRA software package (Wyatt Technologies).

For quantum yield measurements, separate 1 ml drops of protein (32 pm) and substrate (0.2 pm) were placed in a tube, 100 ml of 100 mM sodium phosphate buffer (pH 7) was injected by the luminometer to mix, and the total light output was integrated (generally 5-10 min). For coelenterazine-n, the protein amount was increased 10 fold and the acquisition time lengthened to insure the reaction approached completion.

Kinetics

Kinetics were assessed by injecting 100 ml of 100 mM sodium phosphate buffer (pH 7) containing coelenterazine onto 1 ml of protein (diluted appropriately in EB containing 1% HSA), and recording the light output for 20 min. The final coelenterazine concentrations tested were 118, 24, 4.7, 0.94, 0.19, and 0.038 mM. The final luciferase concentrations were in the range of 1-7 pM. Coelenterazine absorbance was corrected for, although this was only significant for the highest concentration (10% attenuation). The values were converted from photons/s to molecules/s using the data from the quantum yield measurements, inverted from flux units to mass units via integration, and processed using the magnetic curve fitting program Dynafit (Kuzmic, P. (1996) Anal. Biochem. pp. 260-273).

Mammalian Expression

In order to construct mammalian expression vectors, bacterial expression vectors containing the desired mutations were used as templates for PCR, with primers designed such that the N-terminal pelB sequence would be replaced by a methionine codon and a C-terminal stop codon would replace the Myc epitope and 6×His tag. The primers also contained appropriate NheI and HindIII restriction sites to allow insertion of the product into the pcDNA 3.1 plasmid (Invitrogen). The resultant plasmids were transiently transfected using SuperFect (Qiagen) into 293T (DuBridge, R. B., Tang, P., Hsia, H. C., Leong, P. M., Miller, J. H., and Calos, M. P. (1987) Mol. Cell. Biol. 7, 379-387) cells growing in 24 well plates following the manufacturer's protocol. The transfection medium was replaced with fresh medium after 3 h. At several time points following the transfection, cells were lysed using passive lysis buffer (Promega), measured for total protein content using the Bradford assay, and assessed for luciferase activity using coelenterazine in the same manner as described above for bacterially expressed luciferase. Intracellular stability of the luciferases was assessed by adding cycloheximide to the wells at a concentration of 100 g/ml, and lysing cells at several time points thereafter. Westerns were run on lysates with a monoclonal antibody to RLuc (MAb 4400, Chemicon, Temecula, Calif.) in order determine the luciferase protein content, with bacterially produced purified RLuc8 used as the standard.

Results

Computational Predictions for *Renilla* Luciferase

Via sequence similarity searches, RLuc was predicted to contain a characteristic α/β-hydrolase fold from around amino acid 71 to 301 (Marchler-Bauer, A., Anderson, J. B., DeWeese-Scott, C., Fedorova, N. D., Geer, L. Y., He, S., Hurwitz, D. I., Jackson, J. D., Jacobs, A. R., Lanczycki, C. J., Liebert, C. A., Liu, C., Madej, T., Marchler, G. H., Mazumder, R., Nikolskaya, A. N., Panchenko, A., Rao, B. S., Shoemaker, B. A., Simonyan, V., Song, J. S., Thiessen, P. A., Vasudevan, S., Wang, Y., Yamashita, R. A., Yin, J. J., and Bryant, S. H. (2003) Mol Acids Res. 31, 383-387), and was found to have a high level 1-56% similar) to a number of bacterial haloalkane dehalogenases.

Mutagenesis of *Renilla* Luciferase and Screening

In the hopes of further enhancing the stability of RLuc beyond that achieved with the C124A mutation (C152A in (Liu, J. and Escher, A. (1999) Gene 237, 153-159)), a number of further mutations were explored. Candidate mutations were chosen from the alignment data at positions where RLuc most clearly diverged from the consensus sequence. For instance, the candidate mutation A55T was chosen because RLuc harbors the aliphatic amino acid alanine at position 55, while all of the dehalogenases harbor a hydroxylic residue of either threonine or serine. Similarly, S287L was chosen as a candidate because RLuc contains a hydroxylic residue at this position, differing from the consensus aliphatic residue. Some of the candidates, such as M253L, are less obvious. This mutation substitutes an aliphatic residue for another aliphatic, but brings the RLuc sequence into consensus with the highly conserved local sequence near this position.

Complete results with respect to serum stability, activity, and emission spectra peaks are summarized in Table 2 for 25 initial mutations, on a background of RLuc with the C124A mutation, along with data from several other constructs described below. Note that activity was defined as a 10 s integration of the light output curve in order to disfavor mutations that merely increased the burst value at the expense of total light output.

TABLE 2

Mutations of RLuc altered serum stability and light output.

| | Activity (photons/s/mole enzyme) | | | | | Serum $\tau_{1/2}$ (h) | | Wavelength (nm) | |
|---|---|---|---|---|---|---|---|---|---|
| | native | bc | cp | n | bdc | mouse | rat | peak | mean |
| Native RLuc | $(3.2 \pm 0.3) \times 10^{22}$ | $5.4 \times 10^{22}$ | $1.7 \times 10^{22}$ | $8.3 \times 10^{21}$ | $5.8 \times 10^{19}$ | 0.9 | 0.4 | 482 | 497 |
| | Activity (relative to RLuc) | | | | | | | | |
| Initial Mutations | | | | | | | | | |
| C124A | $1.2 \pm 0.1$ | 0.75 | 0.79 | 0.63 | 0.68 | $7.1 \pm 0.4$ | $6.6 \pm 0.5$ | 482 | 498 |
| C124A-ΔMyc | $1.3 \pm 0.1$ | 0.91 | 1.1 | 0.87 | 1.0 | 4.0 | 4.5 | 481 | 499 |
| F33R/I34M/C124A | 0.15 | 0.15 | 0.16 | 0.12 | 0.20 | 0.3 | 0.3 | 481 | 497 |
| E44G/C124A | 0.94 | 0.78 | 0.74 | 0.66 | 0.98 | 2.6 | 3.3 | 486 | 502 |
| A54G/A55G/C124A | 0.12 | 0.10 | 0.06 | 0.15 | 0.19 | 2.4 | 3.0 | 476 | 492 |
| A54P/A55T/C124A | 0.21 | 0.15 | 0.11 | 0.38 | 0.22 | 119 | 129 | 470 | 483 |
| A54P/C124A | 0.05 | 0.04 | 0.05 | 0.08 | 0.06 | 14 | 13 | 468 | 482 |
| A55T/C124A | 1.7 | 1.2 | 0.58 | 1.4 | 2.4 | 30 | 29 | 486 | 504 |
| F116L/C124A | 1.3 | 1.0 | 1.3 | 0.88 | 1.8 | 11 | 9.4 | 486 | 502 |
| C124A/S130A | 1.7 | 1.4 | 1.7 | 1.4 | 2.6 | 18 | 14 | 482 | 498 |
| C124A/K136R | $2.5 \pm 0.3$ | 2.1 | 1.9 | 1.9 | 2.6 | 12 | 11 | 482 | 498 |
| C124A/A143M | 1.7 | 1.3 | 0.95 | 1.5 | 1.6 | 30 | 29 | 480 | 497 |
| C124A/F180A | 0.02 | 0.01 | 0.03 | 0.01 | 0.01 | 1.6 | 1.6 | 488 | 504 |
| C124A/M185V | 3.4 | 3.0 | 15 | 7.8 | 44 | 5.7 | 3.7 | 485 | 500 |
| C124A/M191L | 1.1 | 0.99 | 0.97 | 1.0 | 1.2 | 6.5 | 5.1 | 480 | 496 |
| C124A/E195S/P196D | 0.12 | 0.10 | 0.12 | 0.10 | 0.15 | 1.0 | 0.7 | 482 | 498 |
| C124A/F199M | 0.58 | 0.44 | 0.53 | 0.49 | 0.46 | 6.7 | 6.0 | 480 | 495 |
| C124A/L203R | 0.55 | 0.55 | 0.52 | 0.41 | 0.43 | 2.7 | 2.2 | 484 | 501 |
| C124A/G229E | 0.02 | 0.01 | 0.03 | 0.03 | 0.01 | 1.9 | 1.8 | 473 | 490 |
| C124A/Q235A | 1.2 | 1.1 | 1.1 | 1.0 | 1.2 | 3.3 | 3.6 | 473 | 489 |
| C124A/M253L | 1.9 | 1.4 | 1.6 | 1.6 | 1.7 | 15 | 10 | 471 | 488 |
| C124A/S257G | 1.1 | 0.95 | 1.3 | 1.1 | 3.0 | 1.3 | 1.4 | 477 | 493 |
| C124A/F261L/F262L | 0.00 | 0.00 | 0.00 | 0.00 | 0.00 | N/D | | N/D | |
| C124A/F262L | 0.03 | 0.03 | 0.01 | 0.06 | 0.03 | 5.8 | 6.4 | 478 | 495 |
| C124A/S287L | 3.9 | 2.8 | 3.4 | 5.0 | 9.5 | 28 | 20 | 478 | 496 |
| C124A/M295I | 1.0 | 0.83 | 0.57 | 0.72 | 0.86 | 5.0 | 4.9 | 480 | 497 |
| C124A/K300A | 1.1 | 1.0 | 1.1 | 1.0 | 1.3 | 3.5 | 3.9 | 481 | 497 |
| Stabilized Luciferase | | | | | | | | | |
| RLuc8 | $4.3 \pm 0.2$ | 3.0 | 5.8 | 8.8 | 59 | $253 \pm 58$ | $88 \pm 12.4$ | 487 | 503 |
| Active Site Mutations | | | | | | | | | |
| RLuc8/D120A | 0.000 | 0.001 | 0.001 | 0.003 | 0.21 | >100 | >100 | N/D | |
| RLuc8/D120N | 0.023 | 0.016 | 0.050 | 0.34 | 5.1 | >100 | >100 | N/D | |
| RLuc8/E144A | 0.000 | 0.000 | 0.000 | 0.000 | 0.000 | 57 | 13 | N/D | |
| RLuc8/E144Q | 0.000 | 0.000 | 0.000 | 0.000 | 0.002 | >100 | >100 | N/D | |
| RLuc8/H285A | 0.023 | 0.020 | 0.046 | 0.028 | 0.20 | >100 | 21 | N/D | |

TABLE 2-continued

Mutations of RLuc altered serum stability and light output.

|  | Activity (photons/s/mole enzyme) | | | | | Serum $\tau_{1/2}$ (h) | | Wavelength (nm) | |
|---|---|---|---|---|---|---|---|---|---|
|  | native | bc | cp | n | bdc | mouse | rat | peak | mean |
| Destabilized Luciferases | | | | | | | | | |
| M185V | 4.4 | 2.6 | 12 | 4.1 | 20 | 0.8 | 0.3 | N/D | |
| M185V/Q235A | 4.8 | 2.7 | 14 | 7.1 | 20 | 0.5 | 0.2 | N/D | |

Activity values are the result of integrating over 10 s and are not peak burst values. "Native" indicates the native substrate, while "bc", "cp", "n", and "bdc" indicate the analogs benzyl-coelenterazine, coelenterazinecp, coelenterazine-n, and bisdeoxycoelenterazine, respectively. The results for the native enzyme are reported in absolute units, while the values for the mutants are reported as relative to the native enzyme for the given substrate. Bisdeoxycoelenterazine's emission spectrum is significantly blue shifted from the other substrates, and since the luminometer's enhanced spectral sensitivity at these shorter wavelengths was not corrected for, the absolute unit values represent an overestimation of the real values. The wavelength measurements shown are for native coelenterazine, and the mean and peak wavelengths differ due to the non-symmetrical distribution of the emission spectrum. C124A-DMyc differs from C124A in that the Myc epitope introduced by the bacterial expression plasmid has been removed in order to make it directly comparable to RLuc8. RLuc8 contains the mutations A55T, C124A, S130A, K136R, A143M, M185V, M253L, and S287L. In cases were a particular protein was produced, purified, and assayed independently three or more times, the standard error of the mean is reported.
N/D—Not Determined.

Figure 3:
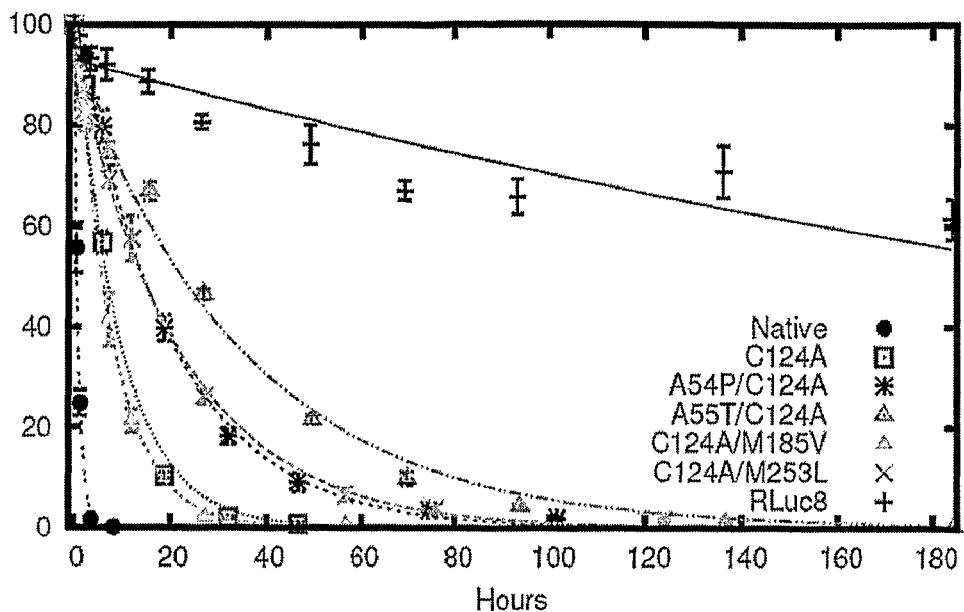
FIG. 3A illustrates mouse serum stability data for RLuc, RLuc8, and several other mutations. The polypeptides were incubated in mouse serum at 37° C. in triplicate, with aliquots removed at various times to determine the remaining luciferase activity. The error bars represent the standard error of the mean, and the lines drawn between the points are from mono-exponential curve fits.
FIG. 3B illustrates a normalized bioluminescence emission spectra for RLuc, RLuc8, and several other mutations. The normalized emission spectrum of RLuc8 when used with bisdeoxycoelenterazine (bdc) is also included for comparison.
Figure 3:
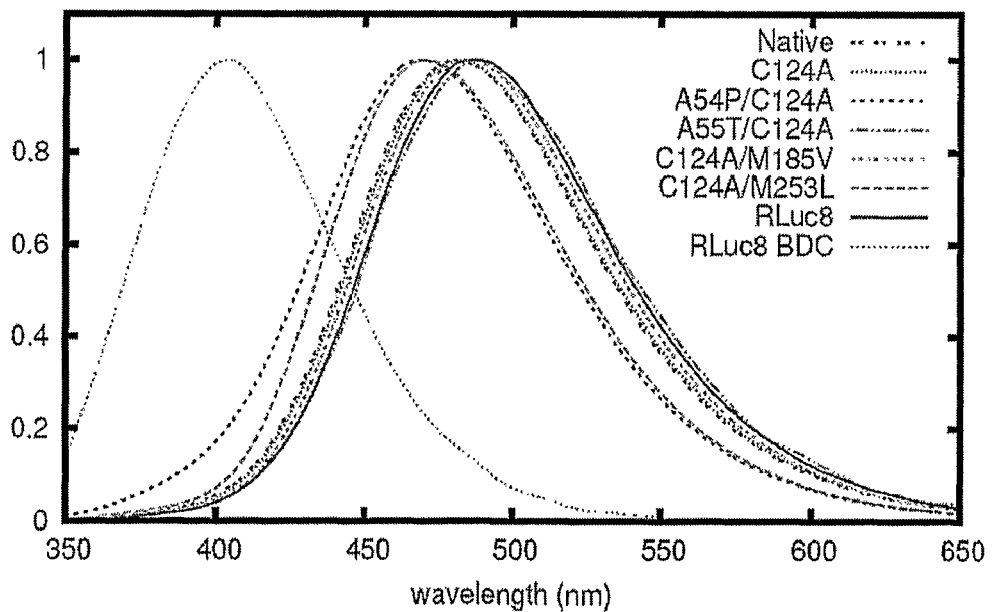

Representative serum stability data and emission spectra are shown in FIGS. 3(a) and 3(b), respectively.

The assayed values for RLuc reported in Table 1 corresponded well with previous values reported in the literature. In terms of stability under serum like conditions, our reported values for recombinant RLuc ($t_{1/2}$=0.4-0.9 h) are in line with Liu et al., who reported a half-life of 0.6 h for recombinant RLuc in hamster blood at 37° C. (Liu, J., O'Kane, D. J., and Escher, A. (1997) Gene 203, 141-148), as well as Lorenz et al. who reported a half-life of 0.5 h for recombinant high ionic strength buffer (Lorenz, W. W., Gray, J. P., Cormier, M. J., Gibson, B. G., and O'Kane, D. J. (1993) in Bioluminescence and Chemiluminescence: Status Report, pp. 191-195, 7th International Symposium on Bioluminescence and Chemiluminescence, Banff, Canada). The measured emission peak for RLuc with coelenterazine (482 nm) corresponded exactly with a previously published value of 482 nm for RLuc purified directly from *Renilla reniformis* (Hart, R. C., Matthews, J. C., Hori, K., and Cormier, M. J. (1979) Biochemistry 18, 2204-2210).

Peak light flux from recombinant RLuc was determined to be $1.2\pm0.210^{23}$ photons/s/mole enzyme when in the presence of 24 mM coelenterazine. Our value corresponds acceptably with the value of $6.5\times10^{22}$ photons/s/mole enzyme reported for RLuc purified directly from *Renilla reniformis* (Matthews, J. C., Hori, K., and Cormier, M. J. (1977) Biochemistry 16, 85-91), and $9\times10^{22}$ photons/s/mole enzyme reported for recombinant RLuc (Lorenz, W. W., Gray, J. P., Cormier, M. J., Gibson, B. G., and O'Kane, D. J. (1993) in Bioluminescence and Chemiluminescence: Status Report, pp. 191-195, 7th International Symposium on Bioluminescence and Chemiluminescence, Banff, Canada).

Combining Mutations for a Stabilized Luciferase

For the purpose of generating a mutant RLuc more appropriate for use as a bioluminescent tag in small animal imaging applications, the initial mutations were judged for serum stability and light output. In all, 7 mutations were deemed as having the most favorable properties and were combined, along with the C124A mutation, into a single protein designated as "RLuc8". The 8 mutations present in RLuc8 are A55T, C124A, S130A, K136R, A143M, M185V, M253L, and S287L (SEQ ID No: 13). Since the Myc epitope was removed during the cloning of RLuc8, a C124A mutant was constructed without the Myc epitope to facilitate a valid comparison (C124A-Δmyc). The stability, activity, and spectra peak values for these two enzymes are shown in Table 1. When compared to the native enzyme, RLuc8 exhibited a greater than 4 fold increase in activity, a 150 fold increase in serum stability, and a small but measurable 5 nm red shift in the emission spectrum. Compared to the C124A mutant, RLuc8 showed a 3 fold increase in activity and at least a 20 fold improvement in murine serum stability.

Light scattering results suggest RLuc8 exists as a monomer in solution, as molar mass moment calculations based on the multiangle scattering indicate a molecular weight of 33.8 kDa (error: 7%) with a relatively low polydispersity across the gel filtration elution profile (~11%).

Quantum Yield and Kinetic Parameters of Mutants

To understand the basis for RLuc8's higher activity, both quantum yield and kinetic measurements were undertaken. The results shown in Table 3 indicated that RLuc8 had a 30% improvement in quantum yield for native coelenterazine, and a ~30 fold increase in quantum yield for bisdeoxycoelenterazine. A Michaelis-Menten model was fit to initial reaction velocity data for coelenterazine concentrations in the range of 0.038 to 24 mM. The results for RLuc, the C124A mutant, and RLuc8 were $K_m$=2.9±1.0, 2.7±0.8, 1.6±0.2, and $k_{cat}$=3.9±0.4, 4.7±0.4, 4.9±0.1, respectively, with the errors presented representing the formal standard errors of the fitted parameters. The results for RLuc are roughly consistent with a previously published $K_m$ value of 2 mM for RLuc in the presence of benzyl-coelenterazine (Matthews, J. C., Hori, K., and Cormier, M. J. (1977) Biochemistry 16, 5217-5220).

TABLE 3

Mutations of RLuc altered quantum yield.

| | Quantum Yield (%) | | | | |
|---|---|---|---|---|---|
| | native | bc | cp | n | bdc |
| Native RLuc | 5.3 ± 0.1 | 3.2 ± 0.04 | 4.7 ± 0.03 | 6.1 ± 0.2 | $(6.1 \pm 0.9) \times 10^{-3}$ |
| C124A | 5.4 ± 0.3 | 3.6 ± 0.1 | 5.2 ± 0.1 | 6.4 ± 0.01 | $(7.7 \pm 0.5) \times 10^{-3}$ |
| A55T/C124A | 5.7 ± 0.2 | 3.9 ± 0.1 | 4.5 ± 0.1 | 5.7 ± 0.1 | $(1.0 \pm 0.9) \times 10^{-3}$ |
| C124A/S130A | 5.3 ± 0.1 | 3.4 ± 0.04 | 5.0 ± 0.1 | 5.9 ± 0.2 | $(6.7 \pm 0.3) \times 10^{-3}$ |
| C124A/K136R | 5.4 ± 0.1 | 3.3 ± 0.1 | 5.1 ± 0.1 | 6.0 ± 0.1 | $(7.1 \pm 0.3) \times 10^{-3}$ |

TABLE 3-continued

Mutations of RLuc altered quantum yield.

| | Quantum Yield (%) | | | | |
|---|---|---|---|---|---|
| | native | bc | cp | n | bdc |
| C124A/A143M | 5.2 ± 0.3 | 3.5 ± 0.1 | 4.8 ± 0.1 | 5.8 ± 0.2 | $(6.3 ± 0.7) \times 10^{-3}$ |
| C124A/M185V | 6.9 ± 0.3 | 6.3 ± 0.1 | 10.1 ± 0.2 | 9.4 ± 0.4 | $(174.4 ± 6.7) \times 10^{-3}$ |
| C124A/M253L | 5.5 ± 0.1 | 3.5 ± 0.1 | 5.1 ± 0.2 | 5.8 ± 0.1 | $(7.6 ± 0.3) \times 10^{-3}$ |
| C124A/S287L | 6.1 ± 0.2 | 5.0 ± 0.1 | 7.2 ± 0.3 | 7.7 ± 0.2 | $(20.9 ± 0.6) \times 10^{-3}$ |
| RLuc8 | 6.9 ± 0.1 | 6.1 ± 0.1 | 8.9 ± 0.1 | 9.6 ± 0.4 | $(198.2 ± 8.5) \times 10^{-3}$ |

Since bisdeoxycoelenterazine's emission spectrum is significantly blue shifted from the other substrates, and since the luminometer's enhanced spectral sensitivity at these shorter wavelengths was not corrected for, the absolute unit values are not accurate although the relative values between proteins are. Standard errors of the mean are reported.

Mutations to Test Proposed Active Site

Figure 4:
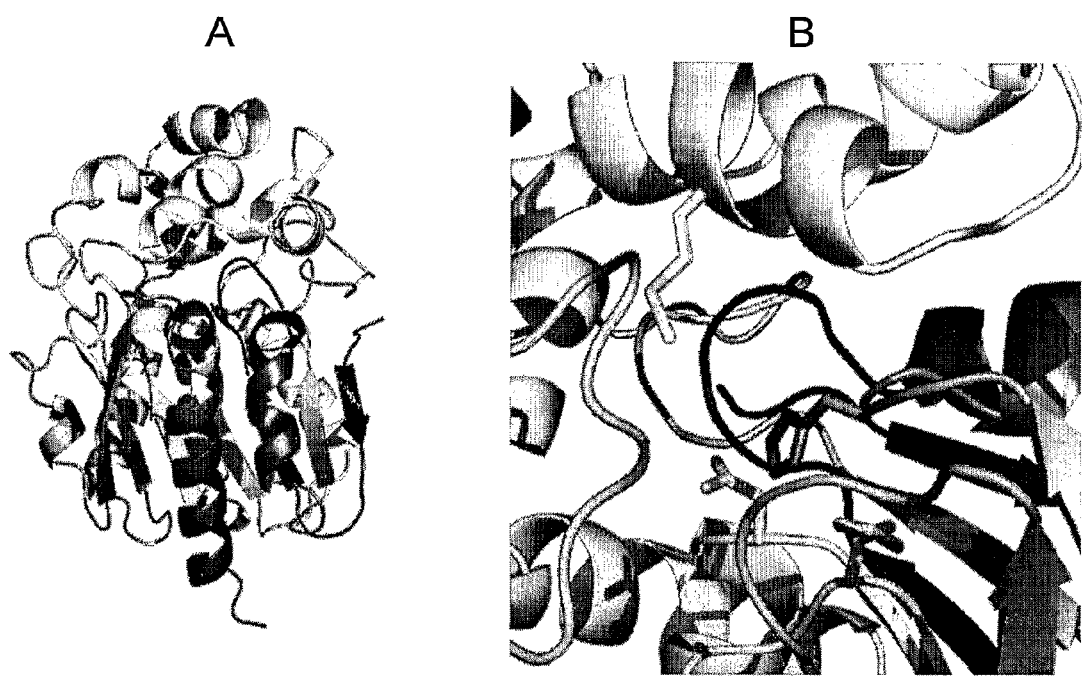
FIG. 4A illustrates a homology model of *Renilla* luciferase based on its similarity to the haloalkane de-halogenase LinB. The region of the enzyme from residue 35 to 309 was successfully modelled using Swiss-Model and is shown. The N-terminus is blue and the C-terminus is red. The presumptive active site is located at the intersection of the red, green, and green-cyan loops.
FIG. 4B illustrates a close up of the homology model showing the potential active site. The side chains for the potential active site residues D120, E144, and H285 are shown, along with the mutation site M185.
Figure 5:
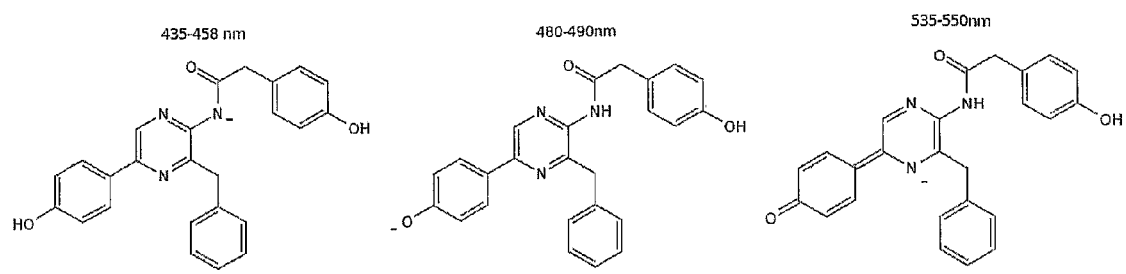
FIG. 5 Illustrates different ionic forms of coelenteramide have different fluorescent emission peaks. The bioluminescent emission spectrum of the *Renilla* luciferase catalyzed oxidation of coelenterazine is believed to be related to the fluorescent emission spectrum of the product of that reaction, coelenteramide.
Figure 6:
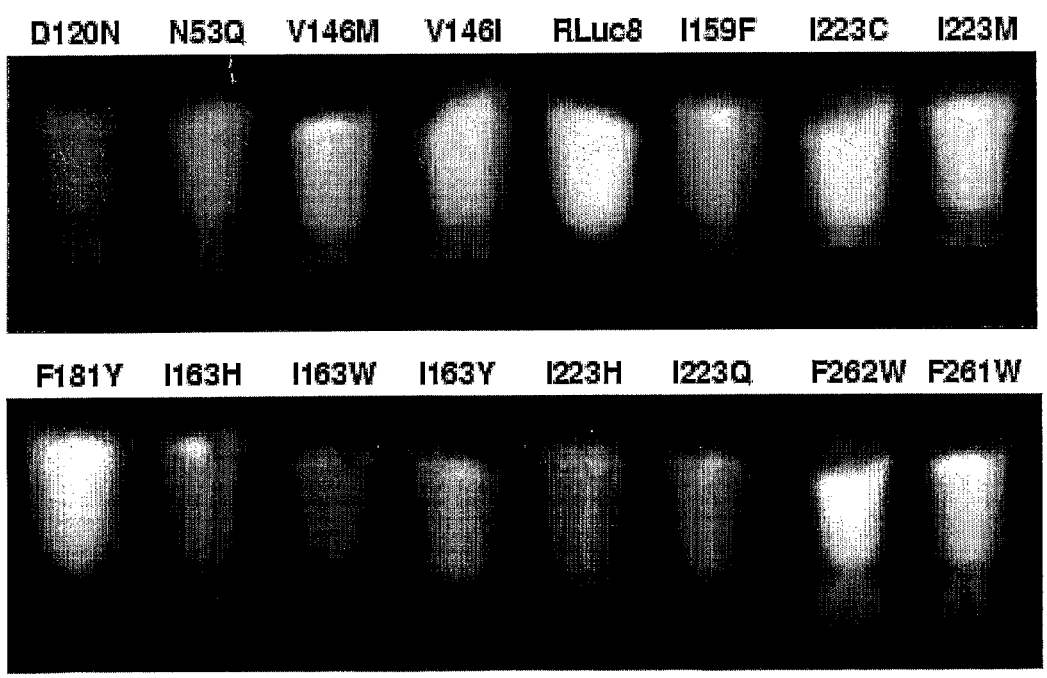
FIG. 6 illustrates that mutations in *Renilla* luciferase's substrate binding pocket (or enzymatic pocket) can lead to shifts in the bioluminescent emission spectrum.

Based on the residues known to be critical for haloalkane dehalogenases activity, D120, E144, and H285 were expected to be required for *Renilla* luciferase activity as well. The locations of these residues in a homology model *Renilla* Luciferase are shown in FIG. 4(*b*). To test the hypothesis that these residues comprise a portion of the enzyme's active site, further mutations were made at these sites on the RLuc8 construct, with the results shown in Table 2. With respect to maintaining luciferase activity, mutations at these proposed active site residues were deleterious.

Combining Mutants for a Destabilized Luciferase

In order to construct brighter yet destabilized mutants, the initial double mutants where compared to the single mutant C124A to identify mutations that led to increased activity without increasing serum stability (e.g. M185V) or decreased serum stability without affecting activity (e.g. Q235A, S257G). Combining these mutations in the absence of C124A resulted in the mutants M185V and M185V/Q235A (Table 2) that showed increased lability and activity in comparison to RLuc.

Testing of Mutants in Mammalian Expression

Figure 7:
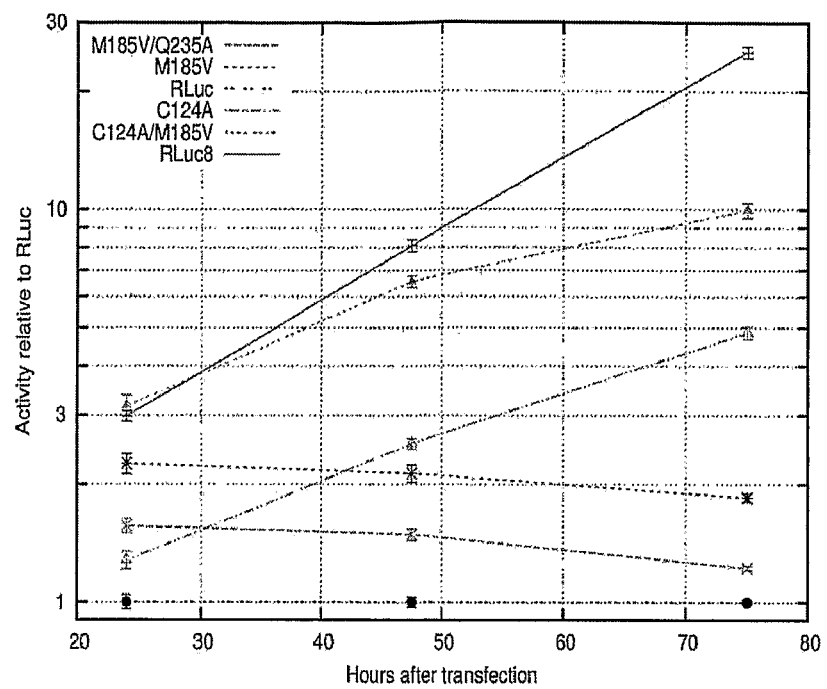
FIG. 7 illustrates mammalian cell expression of native RLuc and several mutants following transient transfection into 293T cells. Light output per total cellular protein was recorded for each condition, and is reported as relative to the value of the RLuc condition at the given time point.
Figure 8:
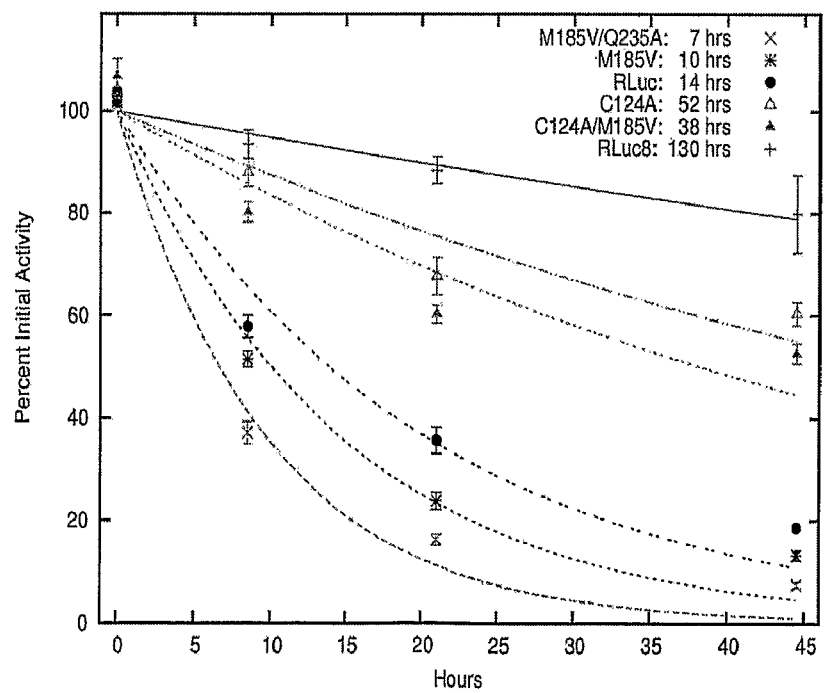
FIG. 8 illustrates the intracellular inactivation of luciferase activity for several of the luciferase variants. The estimated intracellular activity half-lives are given in the figure key.

In order to determine whether the in vitro data gathered for the RLuc mutants and RLuc8 would translate into the context of a mammalian reporter gene, expression vectors were constructed for RLuc, Q235A/M185V, M185V, C124A, C124A/M185V, and RLuc8 in a pcDNA 3.1 backbone. These mammalian expression plasmids were then transiently transfected into 293T cells. Measurements of light output over time following transfection, as shown in FIG. 7 with respect to the RLuc plasmid, demonstrated that the mutations conferred increased light output following transfection in mammalian cells. A cycloheximide study was performed to assess the enzymatic stability for the luciferase variants in the context of the mammalian cytoplasm. As shown in FIG. 8, the relative differences in inactivation resistance, but not the absolute differences, were consistent with the serum inactivation experiments. Through densitometry measurements of western blots performed on the cell lysates, the amount of luciferase was estimated for the different conditions and used to calculate the specific activity values shown in Table 4. These values were roughly consistent with the in vitro data from bacterially expressed protein.

TABLE 4

| | photons/s/mole enzyme |
|---|---|
| RLuc | $(4.2 ± 0.2) \times 10^{22}$ |
| Mutant | Activity (relative to RLuc) |
| C124A | 1.6 ± 0.1 |
| C124A/M185V | 4.2 ± 0.6 |
| M185V | 2.5 ± 0.2 |
| M185V/Q235A | 2.6 ± 0.2 |
| RLuc8 | 4.4 ± 0.2 |

Estimated specific activity values for *Renilla luciferase* and several variants expressed in mammalian cells. 48 h following transfection into 293T cells, the cells were lysed and analyzed for *luciferase* activity. *Luciferase* protein mass in the lysates was estimated via western blotting. Values were measured in quadruplicate, and standard errors of the mean are given. The estimated activity of RLuc is given in absolute values, with the remaining conditions given as relative to that of the RLuc condition.

Conclusion

Luciferases are extraordinarily useful in a variety of experiments that require reporter genes. In instances where the reporter gene is constitutively expressed (e.g. cell trafficking studies (Beilhack, A., Schulz, S., Baker, J., Beilhack, G. F., Wieland, C. B., Herman, E. I., Baker, E. M., Cao, Y.-A., Contag, C. H., and Negrin, R. S. (2005) Blood 206, 1113-1122)), RLuc8 should be advantageous because of its greatly increased light output compared to RLuc in mammalian cells.

In many reporter gene experiments, however, the investigator wishes to follow the dynamics of gene induction and suppression. In these contexts, the high stability of RLuc8 might be a detriment to the experiment, as the stability of this protein could obscure the monitoring of transient gene expression changes. The single mutant M185V and the double mutant M185V/Q235A would be of great utility in these cases, as both these mutants show a ~4 fold increase in activity as well as an increase in protein lability relative to RLuc.

An issue with the use of coelenterazine catalyzing luciferases for reporter gene assays in mammalian cells is that coelenterazine is a substrate for MDR1 P-glycoprotein (Pgp). While the resultant transport of coelenterazine out of mammalian cells can be used to measure levels of Pgp, in most studies this phenomenon leads to an inadvertent modulation of signal intensity. For this reason, there has been interest in the coelenterazine analogs coelenterazine-cp and coelenterazine-n as they are not substrates for Pgp. These analogs, however, suffer from reduced light output when used with RLuc (see Table 2) as well as higher background rates of auto-chemiluminescence. The M185V mutation greatly reduces the disadvantages of these alternative substrates. In the case of coelenterazine-cp, the signal to background ratio when using the M185V mutation is nearly equivalent whether the native substrate or the analog is used.

Bisdeoxycoelenterazine has been proposed as a better analog to use with bioluminescence resonance energy transfer (BRET) studies because of the increased separation between the bioluminescence and the fluorescence spectrums. Bisdeoxycoelenterazine, however, suffers from extraordinary low light output when used with native RLuc (Table 2) because of poor quantum yield (Table 3). Although low bioluminescence quantum efficiency doesn't necessarily imply low light output from BRET, and increased bioluminescence quantum efficiency may not translate into a corresponding increase in BRET output, preliminary data indicate that bioluminescence quantum yield and BRET output are indeed related, at least when the acceptor moiety is a variant of *Aequorea* GFP. Both RLuc8 and the M185V mutation can be of great utility in these BRET assays, as they confer a 20-60 fold increase in light output with bisdeoxycoelenterazine. Interestingly, although C124A alone doesn't improve utilization of bisdeoxycoelenterazine, it appears to facilitate the M185V mutation, as C124A/M185V has a ~2 fold better light output with this substrate compared to M185V alone.

In summary, in the present example mutants of RLuc were characterized with respect to serum stability and light output and these results were used to develop luciferases optimized for different purposes. An 8 mutation form of RLuc (RLuc8) was created that has greatly improved characteristics for use as a bioluminescent label. Compared to the native enzyme, RLuc8 exhibited a 150 fold stability improvement in murine serum, a 4 fold improvement in light output, and a 5 nm red shift in the emission spectrum. The enhancement in light output arises from a combination of increases in quantum yield and improved kinetics. A double mutant of RLuc (M185V/Q235A) was created that has improved performance as a reporter gene. Compared to the native enzyme it has half the stability, as measured in murine serum, while incorporating a close to 5 fold improvement in light output. These optimized *Renilla* luciferases represent significant improvements that will increase the sensitivity of luciferase based assays for both in vitro experiments and in vivo imaging.

Example 2

Bioluminescence Imaging of Angiogenesis in Living Subjects with a Bifunctional *Renilla* Luciferase-VEGF Fusion Reporter Protein Materials and Methods Cell Culture Porcine aortic endothelial (PAE) cells with and without expression of human VEGFR-2 (PAE/VEGFR-2) (kind gift of M. L. Iruela-Arispe; University of California, Los Angeles, Calif.) were cultured in Ham's F-12 media supplemented with 10% fetal bovine serum and 1% penicillin (100 µg/ml) and streptomycin (292 µg/ml), (Invitrogen, Carlsbad, Calif.). Murine SVR angiosarcoma cells were cultured in high-glucose DMEM supplemented with 10% fetal bovine serum and 1% penicillin (100 µg/ml) and streptomycin (292 µg/ml). A375M human melanoma cells (kind gift of M. Kolodny; University of California, Los Angeles, Calif.) were cultured in high-glucose DMEM supplemented with 10% fetal bovine serum and 1% penicillin (100 µg/ml) and streptomycin (292 µg/ml). All cell lines were in subconfluent (70-80%) growth prior to harvesting and counting for tumor xenograft preparation.

Design, Expression, and Purification of Rluc8-VEGF121 (RL8-VEGF) and a VEGFR-2 Binding Mutant (RIK 83.2) and Control Rluc8 Proteins The fusion gene Rluc8-VEGF121 encoding the protein RL8-VEGF was successfully ligated using directional cloning of an amplified VEGF121 PCR product into an expression vector using MfeI and SalI. The prokaryotic expression vector (pBAD-pelB-Rluc8-EGF-His$_6$) has been constructed as previously described. Briefly, a pelB periplasmic leader sequence was placed upstream of the Rluc8 gene encoding a highly stable *Renilla reniformis* luciferase mutant. These eight mutations in the Rluc gene stabilize the luciferase activity of bacterially expressed recombinant protein in serum. The coding sequence for human EGF gene was ligated downstream of the Rluc8 gene and spanned by MfeI and SalI sites. The human VEGF121 cDNA was amplified from an adenoviral genome (kind gift of R. Crystal, Cornell University) using paired primers spanning the full length coding sequence. The 5' primer: 5VEGFMFE (5'-ACGTCAATTGGGAATGGCA-GAAGGAGGAG-3') (SEQ ID NO: 14) contained MfeI site. The 3' primer: VEGFSAL3 (5'-AGGTCGACCCGCCTCG-GCTTGTC-3') (SEQ ID NO: 15) contained a SalI restriction site. After amplification, the PCR product was digested with MfeI and SalI for directional cloning into the MfeI and SalI-cut pBAD-pelB-Rluc8-EGF vector. The subsequent fusion gene of Rluc8-VEGF121 was separated by a two amino acid linker (Leu-Gly). The successful ligation of the Rluc8-LG-VEGF121-His$_6$ fusion gene (encoding the protein probe RL8-VEGF) was confirmed by DNA sequencing. The C-terminal hexahistidine was chosen at this location to ensure purification of full length RL8-VEGF-His$_6$ fusion protein. The QuikChange XL Mutagenesis kit (Stratagene, La Jolla, Calif.) was used to make a VEGF 121 binding mutant by converting amino acids 82-84 from Arg-Ile-Lys to Asp-Leu-Ser. The mutation confers a 50-fold decrease in affinity to VEGFR-2 compared with wild-type VEGF. The primers used for the mutagenesis of the plasmid pBAD-pelB-Rluc8-VEGF121-His$_6$ were RIK83up.1 (5'-CAA CAT CAC CAT GCA GAT TAT GGC AGC AGC ACC TCA CCA AGG CCA GCAC-3') (SEQ ID NO: 16) and RIK83.down.1 (5'-GTG CTG GCC TTG GTG AGG TGC TGC TGC CAT AAT CTG CAT GGT GAT GTT G'-3') (SEQ ID NO: 17) based on modifications of primer pairs used to create binding mutants of VEGF as previously described. DNA sequencing confirmed successful mutagenesis.

Protein Expression

LMG 194 *E. coli* (Invitrogen, Carlsbad, Calif.) were transformed with pBAD-pelB-Rluc8-VEGF121-His$_6$ (RL8-VEGF), pBAD-pelB-Rluc8-RIK 83.2-His$_6$ (RL8-RIK 83.2), and pBAD-pelB-Rluc8-His$_6$ (Rluc8) and grown to OD$_{600}$=0.7 in mini-Luria-Bertani (LB)-ampicillin cultures. Larger LB-ampicillin cultures were brought to a final arabinose concentration of 0.2% arabinose for induction at the prokaryotic araC promoter in the pBAD vector (Invitrogen, Carlsbad, Calif.). Once induced, the cultures were grown for 12 hours at 30° C. at 210 rpm in a rotatory incubator. Cells were pelleted and a modified osmotic shock protocol was used to isolate the periplasmic fractions. Periplasmic fractions were brought to 1 mM PMSF and filtered through a 0.22 µM membrane (Nalgene, Rochester, N.Y.). Periplasmic fractions were purified using Ni-NTA SuperFlow columns (QIAGEN, Chatsworth, Calif.) in 300 mM Nacl and 20 mM HEPES, pH 8.0 with 20 mM imidazole in the loading and washing steps. The elution buffer contained 300 mM NaCl, 20 mM HEPES, pH 8.0 and 250 mM imidazole. Pooled fractions were subsequently concentrated in an Amicon 10,000 MW concentrator (Millipore, Villerica, MA) and then dialyzed against 3 changes of phosphate-buffered saline, pH 7.4 overnight at 4° C. in a 10,000 MW Slid-A-Lyzer cassette (Pierce, Rockford, Ill.).

The luciferase activity of equal amounts of purified protein was measured in a TD 20/20 luminometer (Turner Designs, Sunnyvale, Calif.) for a period of 10 seconds in the presence of 0.5 μg of coelenterazine (Nanolight Technology/Prolume Ltd., Pinetop, Ariz.).

Characterization of RL8-VEGF, RL8-RIK 83.2, and Rluc8 by SDS-PAGE and Western Blotting and Luciferase Activity Equal amounts (5 micrograms) of purified proteins were analyzed by gel electrophoresis in 4-20% gradient SDS-PAGE gels under reducing conditions. The gels were stained with Coomassie Blue (Bio-Rad, Hercules, Calif.). For Western Blots, equal amounts (1 microgram) of purified proteins were resolved by gel electrophoresis in a 4-20% gradient SDS PAGE gel and then transferred to nitrocellulose. Western Blot of the proteins using anti-C-terminal His-tag conjugated with HRP at 1:5000 dilution (Invitrogen, Carlsbad, Calif.) confirmed the presence of His-tagged luciferase in all three constructs. After stripping of the nitrocellulose membrane, an anti-Renilla luciferase (RL) antibody (Chemicon, Temecula, Calif.) at 1:10,000 was used to detect the RL protein in each of the proteins. Goat anti-mouse heavy and light chain antibody conjugated with horseradish peroxidase was used at 1:30,000 for secondary antibody detection. The Enhanced ECL chemiluminescence detection kit (GE Healthcare, Piscataway, N.J.) was used for exposure of protein bands to x-ray film.

Competition Bioluminescence Cell ELISA

PAE cells without and with human VEGFR-2 expression were plated overnight in 48 well culture dishes and incubated in serum free Ham's F-12 media with RL8-VEGF fusion protein or RL8-RIK 83.2 binding mutant protein for 1 hour at 37° C. in the presence of varying amounts of "cold" recombinant human VEGF 121 (PeproTech, Rocky Hill, N.J.). Cells were washed and incubated with 0.5 μg of coelenterazine substrate and immediately imaged in the Xenogen IVIS 100 optical cooled charge-coupled device (CCD) (Xenogen, Alameda, Calif.). Regions of interest (ROIs) were drawn over the cell area and quantified in average photons/second/centimeter$^2$/steradian (photons/s/cm$^2$/sr) by using Living carnage Software version 2.50 (Xenogen, Alameda, Calif.).

Mouse Serum Stability Assays

Mouse serum (Calbiochem, EMD Biosciences, La Jolla, Calif.) was aliquoted at 50 μL into mini-reaction tubes and incubated with 1 μg each of RL8-VEGF or RL8-RIK 83.2. Time points of incubation were 0, 4, 8, 12, 24, and 48 hours. PAE/VEGFR-2 cells were plated in 48 well culture plates at 50,000 cells/well and grown overnight. After washing once in PBS, pH 7.4, cells were re-fed serum free Ham's F-12 media. 25 μL aliquots of the given incubated proteins in serum was added to each well and allowed to incubate for 30 minutes. Cells were washed 2× with PBS, pH 7.4 and then 0.5 μg of coelenterazine added per well and imaged in the Xenogen IVIS optical cooled charge-coupled device (CCD) (Xenogen, Alameda, Calif.). Regions of interest (ROIs) were drawn over the cell area and quantified in average photons/second/centimeter$^2$/steradian (photons/s/cm$^2$/sr) by using Living Image Software version 2.50 (Xenogen, Alameda, Calif.). Each condition was performed in triplicate, and error measurements are in S.D.

Results

Design, Expression, and Purification of Rluc8-VEGF121 (RL8-VEGF) and VEGFR-2 Binding Mutant Rluc8-RIK 83.2 (RL8-RIK 83.2) and Control Rluc8

Figure 9:
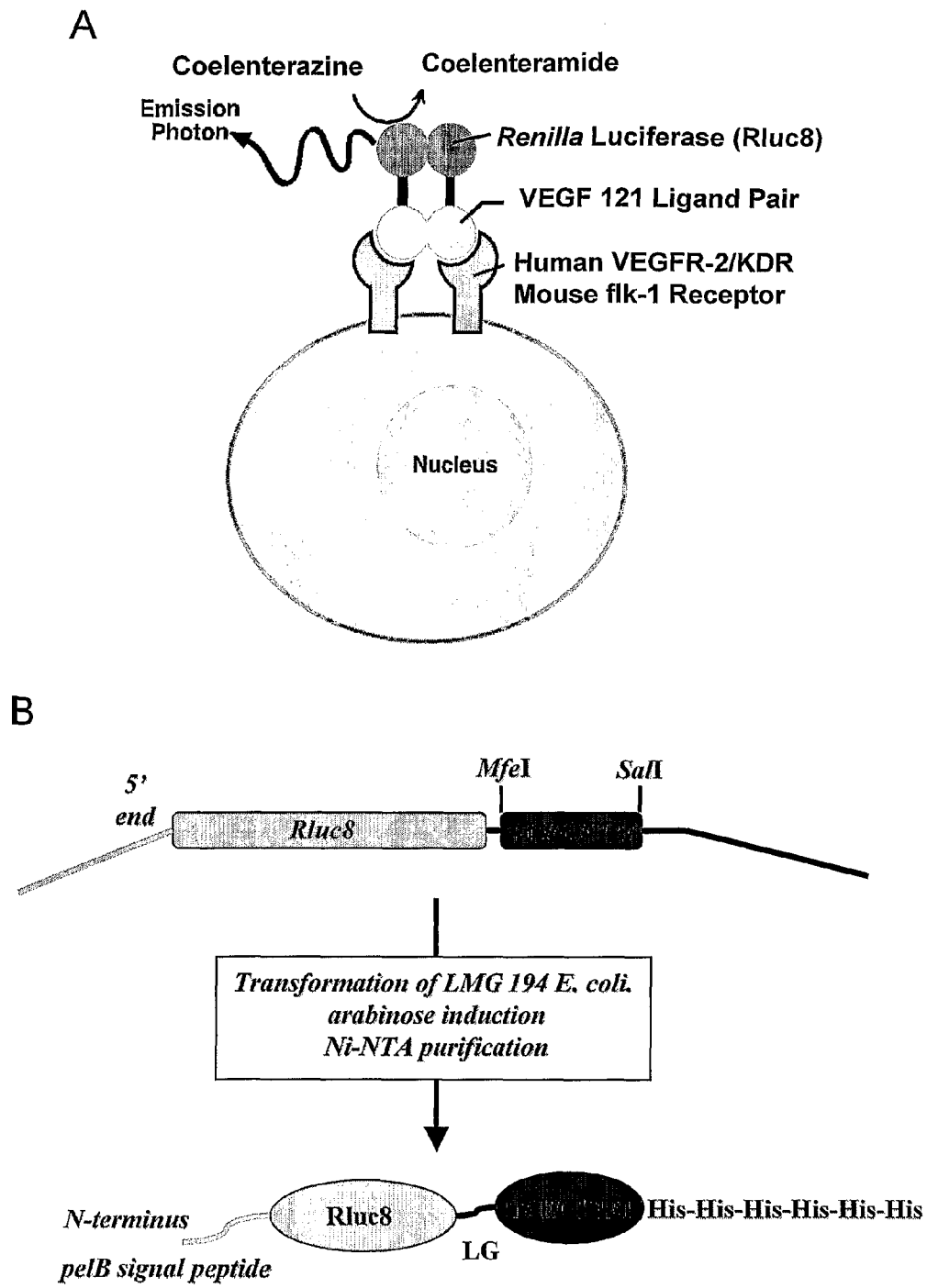
FIG. 9A illustrates a schematic diagram of RL8-VEGF fusion reporter protein binding to target receptors on cells. The novel probe can target receptors (VEGFR-2/FLT-1) based on the targeting moiety (e.g., VEGF121 dimer). The enzymatic reporter moiety (RL8) can then oxidize its substrate coelenterazine into coelenteramide without the need for ATP, leading to detectable photon emission.
FIG. 9B illustrates an assembly of genes encoding novel fusion reporter probe RL8-VEGF. A directional cloning strategy was used to ligate the human VEGF 121 cDNA in-frame to the Rluc8 mutant gene resulting in a leu-gly (LG) linker. A hexahistidine sequence in the C-terminal protein was used for nickel column purification of the protein from the periplasmic fraction of LMG 194 *Escherichia coli*.

The prokaryotic expression vector (pBAD-pelB-Rluc8-EGF-His$_6$) has been constructed as previously described. A directional cloning strategy using MfeI and SalI sites flanking the epidermal growth factor (EGF) coding sequence was used to ligate VEGF 121 in-frame to the Rluc8 gene (FIG. 9b). PCR oligonucleotide primers with 5' MfeI and 3' SalI sites were designed for amplification of VEGF 121 from an adenoviral genome and subsequent digestion with the restriction enzymes. The double-digest was ligated into the pBAD-pelB-Rluc8-His$_6$ vector that also had been digested with MfeI and SalI. Successful ligation was confirmed by DNA sequencing, and a dipeptide linker of Leu-Gly was the final linker between the Rluc8-VEGF 121 fusion protein. LMG 194 *E. coli* were transformed with the expression vector and logarithmic phase LB-ampicillin cultures were induced with L-arabinose for induction at the araC prokaryotic promoter for inducible expression of the RL8-VEGF protein. The periplasmic leader sequence was used to direct translation of protein into the periplasm of the cells. Osmotic shock was used to isolate the periplasmic action of the cells and the recombinant fusion protein was purified by metal chelate affinity chromatography.

As a control, a VEGF mutant was created using site-directed mutagenesis of three amino acids in the conserved binding portion of the VEGF protein. The critical amino acid residues in the hairpin loop of VEGF are Arg-82, Lys-84, and His-86. Mutants were created in this binding pocket as a control for these studies. The amino acids Arg-82, Ile-83, and Lys-84 were successfully exchanged to Asn-Leu-Ser, and the same purification scheme was followed to isolate nearly equivalent amounts using the osmotic shock protocol and metal chelate chromatography. As a further control, the Rluc8 control protein was expressed and purified without the VEGF targeting domain.

Characterization of Purified Protein

Figure 10:
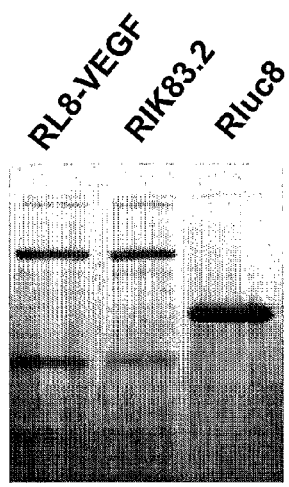
FIG. 10A illustrates coomassie Blue staining of purified fusion proteins and control proteins. Lane 1: RL8-VEGF, Lane 2: RL8-RIK 83.2 binding mutant, Lane 3: Rluc8 only. The 50 kDa fusion proteins are the predominant bands in Lane 1 and Lane 2 for RL8-VEGF and RL8-RIK 83.2, respectively. The Rluc8 lane shows a dominant 36 kDa band as expected and a possible dimerization band in Lane 3.
FIG. 10B illustrates a Western Blot of purified proteins. The first panel shows anti-C-terminal histidine tag antibody detection of the purified proteins. After stripping of the membrane, an anti-Renilla luciferase antibody was used to re-probe and showed the identification of the same bands recognized by the anti-C-terminal histidine tag antibody.
FIG. 10C illustrates competitive bioluminescence ELISA on PAE/VEGFR-2 overexpressing cells. RL8-VEGF fusion protein preferentially bound to VEGFR-2 over-expressing cells (PAE/VEGFR-2), while the RIK83.2 binding mutant showed 80% loss of binding. Increasing the "cold" VEGF 121 concentration (in ng/mL) showed a dose-dependent competition for VEGFR-2 binding with RL8-VEGF. Fifty percent inhibition of binding of RL8-VEGF was achieved at 45 ng/mL VEGF 121. The RIK 83.2 binding mutant showed no effect from competition by VEGF 121.
Figure 10:
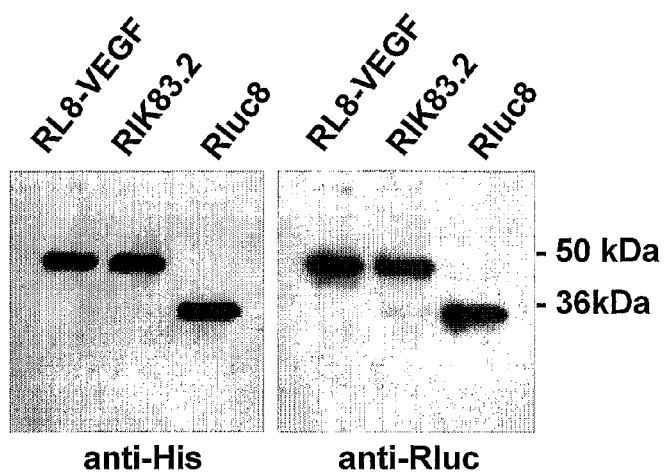
Figure 10:
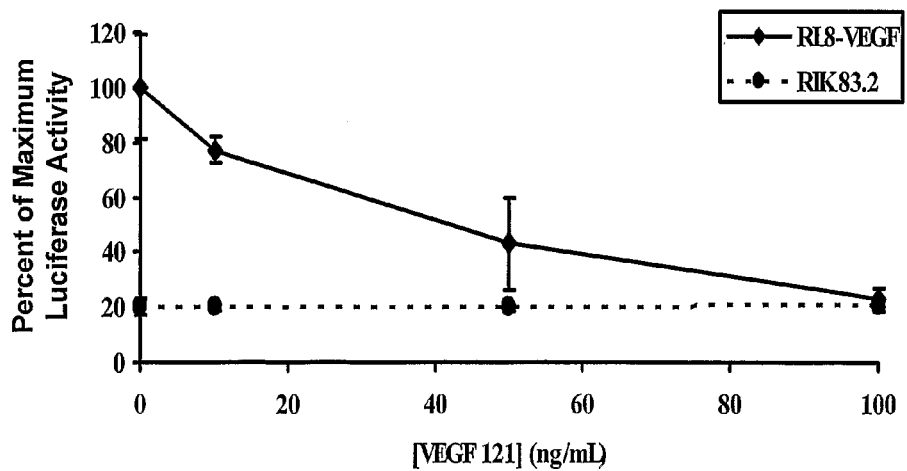

The RL8-VEGF and RL8-RIK 83.2 VEGFR-2 binding mutant fusion proteins were analyzed for retention of activity after periplasmic harvesting and nickel ion metal chelate affinity purification. Coomassie Blue staining of equally loaded purified protein extracts showed equal intensities of the expected 50 kDa (VEGF 121=14 kDa, Rluc8=36 kDa) fusion proteins in each lane labeled RL8-VEGF and RL8-RIK 83.2 (FIG. 10z). Multiple additional bands were identified which likely represent impurities in the purification process. Proteolytic degradation of the protein was expected since it has been commonly shown that fusion proteins with eukaryotic peptide sequences can be degraded. Using an anti-C-terminal His-tag mAb conjugated with horseradish peroxidase, single bands of fusion proteins were seen, and the multiple impurities in the Coomassie Blue stained gel were not seen in the Western Blots (FIG. 10b). For confirmation of correct translation of *Renilla* luciferase (RL) protein, the nitrocellulose membrane was stripped and re-probed using an anti-RL mAb and demonstrated recognition of RL sequences in the purified proteins. Non-specific background staining can be seen at higher molecular weights and likely reflects secondary antibody binding, as the previously probed blot with anti-C-terminal His-tag mAb does not show corresponding contaminating bands. Rluc8 as a control was shown to resolve at the expected molecular weight of 36 kDa.

The luciferase activities were expected to be nearly equivalent between equal mass amounts of the RL8-VEGF and RL8-RIK 83.2 mutant. Using a luminometer the luciferase activity of purified protein (1 μg each) was assessed and showed that the final luminescence activities of purified proteins were $5.50\times10^{11}\pm2.11\times10^{9}$ RLU/μg for RL8-VEGF and $6.14\times10^{11}\pm4.25\times10^{10}$ RLU/μg for RL8-RIK 83.2 binding mutant (n=3 for both, p<0.05).

To test for preservation of VEGFR-2 affinity of RL8-VEGF, and the lack of binding affinity of RL8-RIK 83.2, a competition bioluminescence ELISA assay was used. Porcine aortic endothelial (PAE) cells with overexpression of human VEGFR-2 (PAE/VEGFR-2) were assayed for retention of bioluminescence in the presence of purified proteins. Purified recombinant human VEGF 121 was co-incubated in the wells of the assay plate at 0, 10, 50, and 100 ng/mL in triplicate. FIG. 10c shows the dose-dependent inhibition of binding of RL8-VEGF with increasing concentration of purified VEGF 121. The VEGFR-2 binding mutant RL8-RIK 83.2 shows a 5-fold decrease in binding to PAE/KDR cells relative to RL8-VEGF and no dose-dependent competition from purified VEGF 121.

Figure 11:
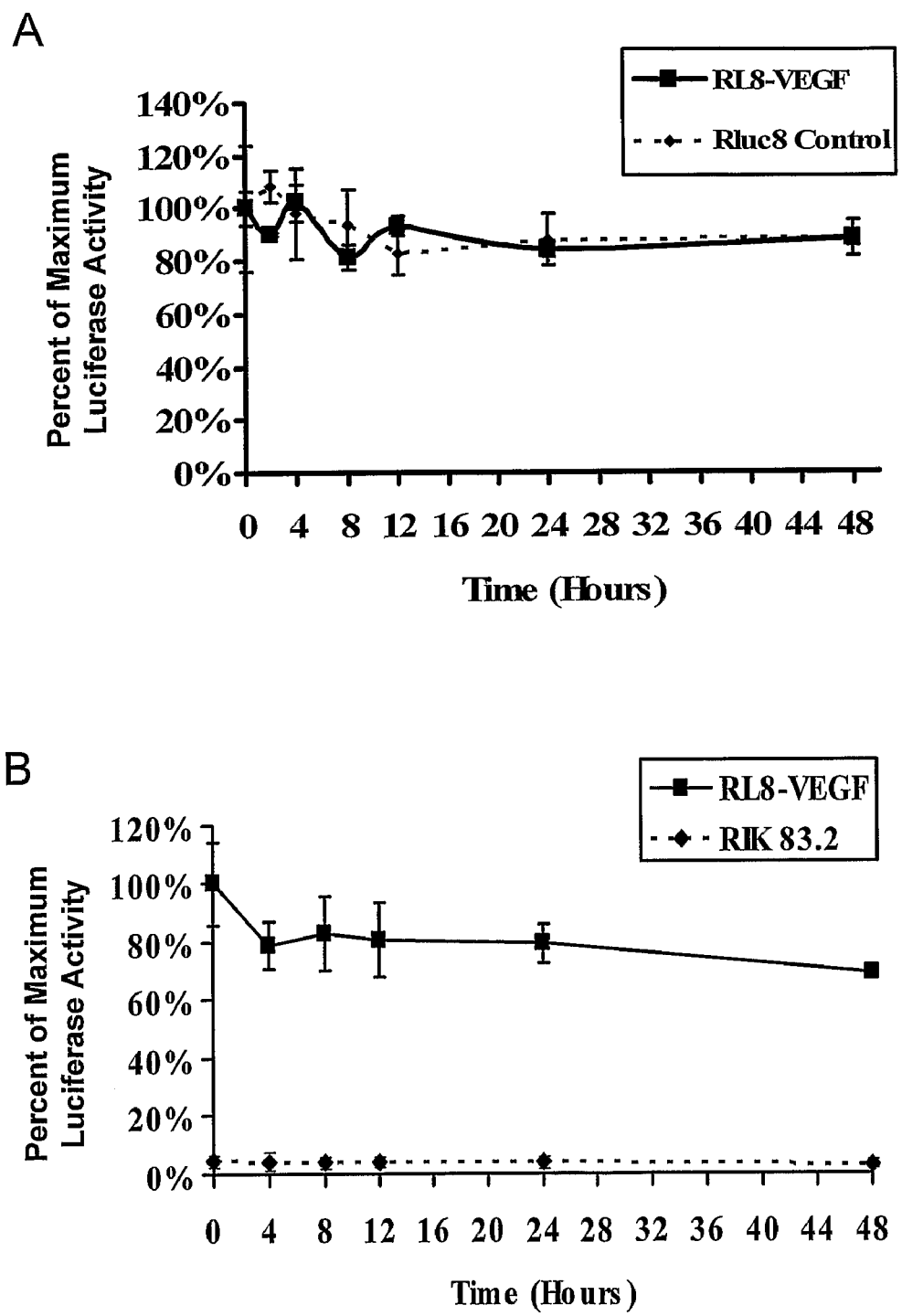
FIG. 11A illustrates an in vitro assay for serum stability. One microgram of indicated RL8-VEGF fusion reporter probe or Rluc8 control protein was incubated at 37° C. in 50 microliters of mouse serum at 0, 2, 4, 8, 12, 24, and 48 hours. Aliquots were incubated with coelenterazine substrate and assayed for luciferase activity in a luminometer. Values are represented as percent of Time 0 hours luciferase activity.
FIG. 11B illustrates the serum effect on bifunctional reporter protein affinity. The RL8-VEGF and RL8-RIK 83.2 binding mutant fusion proteins were incubated at 37° C. at the indicated times. The cell binding affinities using bioluminescence ELISA was tested on PAE/VEGFR-2 cells and showed 75% retention of binding up to 48 hours of incubation. The RL8-RIK 83.2 binding mutant showed a significant loss of binding compared with the RL8-VEGF fusion protein after 48 hours of serum incubation.

Serum Stability of Purified RL8-VEGF, RL8-RIK 83.2 and RLuc8:

The goal of using an injectable fusion reporter protein probe would require high serum stability in the face of factors that would decrease the luciferase activity from the blood including proteolytic degradation. Therefore, the serum stability of the fusion protein was assayed to determine whether placement of the VEGF targeting portion altered the extremely stable nature of the Rluc8 luciferase activity. 1 μg of purified RL8-VEGF and Rluc8 were incubated for 0, 2, 4, 8, 12, 24, and 48 hours in mouse serum at 37° C. Aliquots of serum were assayed in the presence of 0.5 μg of coelenterazine substrate in a luminometer in triplicate. The addition of the VEGF domain did not alter the serum stability for the Rluc8 control alone. Both RL8-VEGF and Rluc8 retained 88% of their luciferase activity after 48 hours of incubation in mouse serum (FIG. 11a).

To determine whether serum incubation would alter the VEGF affinity to VEGFR-2 over time in serum at 37° C., PAE/KDR cells were plated in 48 well plates and incubated with aliquots of 50 μL of serum plus 1 μg of either RL8-VEGF or RIK 83.2 VEGFR-2 binding mutant at 0, 4, 8, 12, 24, and 48 hours. FIG. 11b shows that RL8-VEGF fusion protein retained 69% of its binding and activity to VEGFR-2 on PAE cells. The VEGFR-2 binding mutant RIK 83.2 showed only 4% binding relative to the RL8-VEGF fusion protein binding throughout the assay from 0 to 48 hours. Rluc8 also showed a very similar level of 3-5% binding throughout a separate assay (data not shown).

Discussion

The VEGFR-2 (human KDR/mouse flk-1) receptor tyrosine kinase is a potentially useful target for delivery of tracers or probes to image nascent vascular networks in and around tumors. Since the VEGFR-2 is found in both tumor cells and the microvasculature around these cells, the delivery of a reporter protein probe (e.g., targeting moiety) in vivo makes it possible to image small micrometastases for early detection (see FIG. 9a for schematic of how the VEGFR-2 targeting moiety functions). The genes that encode for the soluble ligands, VEGF 121 and VEGF 165, and for the receptor VEGFR-2 have been cloned. Attaching an enzymatic reporter protein makes it possible to identify areas where early angiogenic signals are delivered by targeting the same pathway that cells use to recruit endothelial cells in times of hypoxia and increased metabolic demand. The soluble form of the VEGF ligand, VEGF 121, was chosen for this purpose. An injectable 50 kDa fusion protein was engineered for VEGFR-2 targeting and subsequent bioluminescence reporter activity in living subjects (e.g., a VEGFR-2 specific targeting moiety).

Attempts at imaging angiogenesis have relied more on surrogate markers for increased blood vessel formation such as changes in vessel permeability, perfusion, and MRI blood pool agents. Radionuclide approaches include PET using $^{18}$F to measure glucose metabolism and blood pooling. Direct methods of imaging VEGFR-2 in new endothelial cells include $^{123}$I and [111]Indium labeled VEGF recombinant protein in tumor and pro-angiogenic gene therapy trials for ishemic heart disease, respectively. Sensitivity is the main limitation of these studies of direct camera imaging of angiogenic receptors. Recent reports include using a prokaryotically expressed VEGF targeting protein for use with SPECT detection. Optical imaging has been examined for the feasibility of detecting gene transfer into vascular endothelial cells with green fluorescent protein gene, but autofluorescence in background tissue limited the signal detection[28]. Bioluminescence reporter imaging has been useful to prevent unwanted background autofluorescence and has been utilized in reporter gene therapy studies. For this reason, exogenously delivered protein conjugated with fluorochrome dyes such as Cy5.5 or Cy7 would have poor signal-to-noise images. Hence a bioluminescent enzyme deliverable by the fused VEGF protein as chosen and targeted to VEGFR-2 on the surface of dividing endothelial cells.

The functional expression and targeting of therapeutic toxin-VEGF fusion proteins have been described using VEGF 121 fused in-frame to the *Diptheria* exotoxin, Shiga-like toxin, and a plant toxin, gelonin. The present example demonstrates a diagnostic imaging agent with bifunctional ends with targeting and reporter activities. This targeting moiety retained highly stable serum target binding and enzymatic activity allowing for clearance of the agent from the blood pool over time.

Cell cultures results using PAE/VEGFR-2 cells validated binding from human VEGF 121 to human VEGFR-2. Although the human VEGF 121 coding sequence was used, good binding to mouse flk-1 receptor was expected due to the 85% binding homology. Competitive bioluminescence ELISA against these cells confirmed the specific targeting of the VEGF domain to VEGFR-2. The serum stability of this protein showed 88% of retained binding and bioluminescence activity to 48 hours of incubation in mouse serum. In the previously described toxin-VEGF studies, therapeutic effects were elicited regardless of the domain order in the fusion protein. Therefore, the VEGF targeting, which resides in the internal residues of the protein, should not be limited by the effects of protein domains at either N-terminal or C-terminal ends. The molecular imaging of tumor xenografts have been described using a novel SPECT labeling approach with $^{99m}$Tc-VEGF.

Combined molecular imaging approaches for the earlier detection of breast cancer using PET and optical hand-held transducers may be important for earlier detection of small radiographically occult breast cancers as a complement to mammography. Mammography has achieved much success in reducing the overall deaths from breast cancer. Earlier detection may be achieved once methods to image the events preceding cancer invasion and metastasis can be developed as an adjunct to radiographic screening.

Example 3

Development of Color Shifted *Renilla* Luciferase Variants

Methods

Please note that many of the methods used in this example are similar to those from Example 1 and are not repeated here. Only those methods that have not been previously described or have been modified are discussed below.

Random Mutagenesis

Random mutagenesis was accomplished using Mutazyme II (Stratagene). Following PCR, the product was purified and digested overnight in a 37° C. bacterial incubator with DpnI (to remove parental template) along with the appropriate restriction enzymes (NcoI/SalI) for insertion into the plasmid backbone. After gel purification, a total of 200 ng of mutated insert and plasmid backbone (SalI/NcoI digested pBAD) at a 2:1 insert/backbone molar ratio were ligated overnight at 16° C. in a 20 µl reaction. 5 µl of the ligated product was then transformed into 50 µl Top 10 bacteria cells (Invitrogen), and spread on 8 150 mm diameter Terrific Broth/50 µg/ml ampicillin (TB/Amp) agar plates containing 0.2% L-(+)-arabinose. Following 20 h of incubation at 32° C., the plates were airbrushed with a phosphate buffered saline (PBS) solution containing 1% 0.5 mg/ml coelenterazine in propylene glycol and imaged immediately using an IVIS 200 bioluminescence imaging system (Xenogen). Three 5 s acquisitions were made using a DsRed, a GFP, and an open filter. Acquired images were processed in GNU Octave using a collection of custom scripts. Colonies were selected both automatically with these scripts as well as manually for brightness and/or spectral shifts. Colonies were then screened further as described below in "Small Scale Protein Purification".

Saturation Mutagenesis

Saturation mutagenesis at specific locations was performed by making use of Type IIs restriction enzymes and primers containing a randomized codon sequence. The method presented here is a modification of a previously published protocol (Ko J K, Ma J. *Am. J. Physiol. Cell Physiol.* 288(6):C1273-C1278, 2005) and differs mainly in that the entire plasmid is used as the template for PCR, obviating the need for a second ligation step. Standard PCR conditions were used, with the exception that the extension time was increased to 2 min/kb, 5% DMSO was included in the reaction, template was used at 10% of usual concentrations and primers were used at 20% of usual concentrations. restriction digests using BpiI (Fermentas, Hanover, Md.) and DpnI were performed overnight in a 37° C. bacterial incubator. Following gel purification, ligation, transformation, and plating was done as in the random mutagenesis case.

Small Scale Protein Expression

For random and saturation mutagenesis experiments, the clones initially selected from the agar plates were further screened by small scale expression experiments. Selected colonies were picked into 2 ml TB/Amp each and grown to saturating conditions at 37 C (~12 h). 2 ml TB/Amp containing 0.2% L-(+)-arabinose was then added to each tube and the cultures were grown an additional 12 h at 32° C. Following this, half of each culture was spun down and submitted to the osmotic shock protocol as described in Example 1. The periplasmic fractions were assayed for specific activity, assayed for bioluminescence color shifts visually, and stored at 4° C. Bright and/or color shifted variants were then submitted for sequencing. For variants identified as having novel mutations, the periplasmic fraction was brought to 1×WB (Example 1) from a 10× stock, and further purified using nickel affinity spin columns (Ni-NTA Spin Kit, Qiagen) with 1×EB as the elution buffer. The elution was brought to 1% HSA, and then assayed for specific activity. Interesting color shifts were confirmed by spectrophotometry as described in Example 1. As before, emission spectra were filtered as necessary and normalized to equalize the total area under the curve.

Results

Probing of the Active Site of RLuc8

Figure 12:
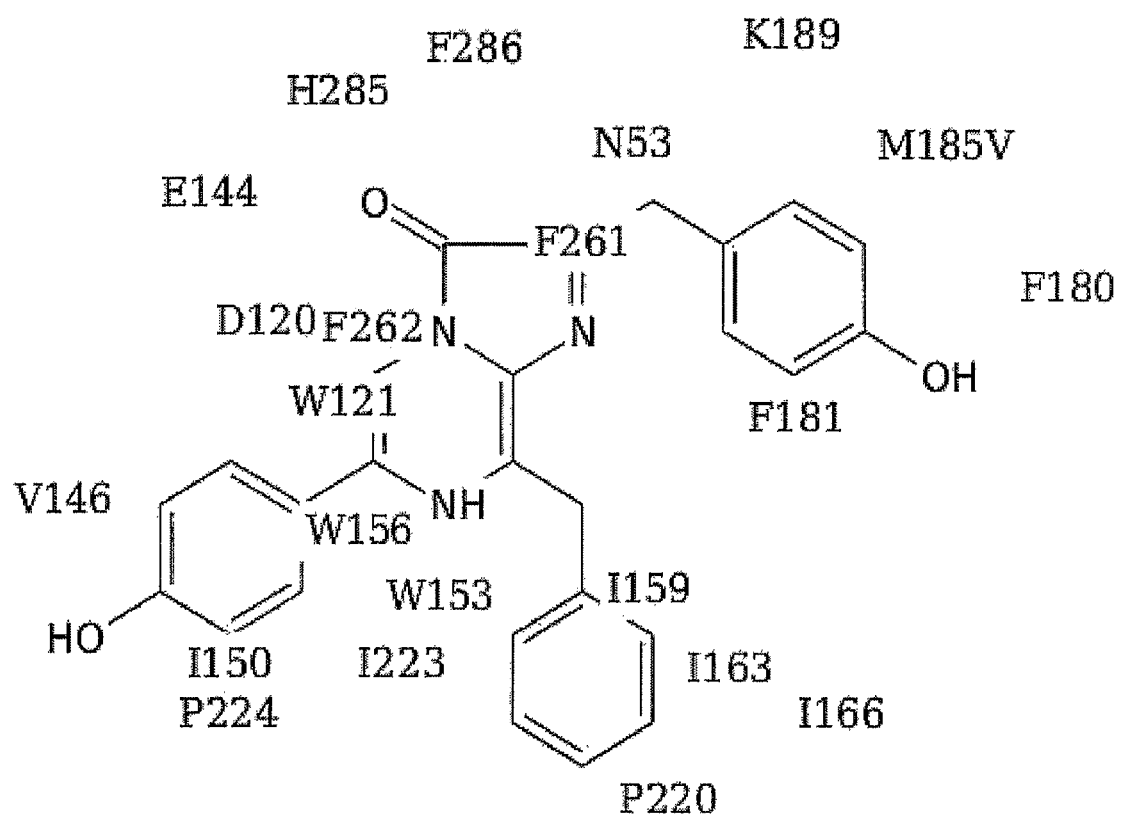
FIG. 12 illustrates an estimation for the coelenterazine orientation in the context of a Swiss-Model derived RLuc8 homology model. The schematic shows which residues putatively interact with the substrate based on the estimate.

In an attempt to rationally alter the emitted wavelength of *Renilla* luciferase, the location and orientation of the substrate in the active pocket was conjectured. This was done by assuming the catalytic triad was used for coordinating the oxygen, that the orientation of the substrate would be similar to that seen with other a/b-hydrolases, and that the varying affinities of the different mutations in Example 1 for the various coelenterazine analogs were due to close interactions between the mutation and the altered side chain of the analog. This conjecture was formulated using a Swiss-Model derived RLuc8 homology structure. The results of this exercise are shown in FIG. 12. Using this model of coelenterazine/coelenteramide in the active pocket as a guide, a total of 74 site specific mutations were made at the 22 residues thought to interact with the substrate. With the exception of the I223 location at which mutagenesis was saturating, the subset of possible mutations done at each residue was selected based on what would be considered "safe" with respect to the tertiary fold of the enzyme. The results of this screen are shown in Tables 5 and 6. From this screen, a total of 21 mutations at 10 different residue locations resulted in observable shifts in the emission spectrum. The variants with bathochromic shift mutations presumably have active pockets that favor the green fluorescing anion form of coelenteramide. Unsurprisingly, given that the enzymatic pocket of RLuc8 is already evolved for the reaction at hand, nearly all these mutations led to significant reductions in the light output of the luciferase.

TABLE 5

Results of site-directed mutagenesis in the active pocket of RLuc8.

| | Specific Actvity (relative to RLuc) | | | | | Wavelength (nm) | | | |
|---|---|---|---|---|---|---|---|---|---|
| | native | hh | cp | n | bdc | peak | mean | fwhm | % > 600 nm |
| RLuc8 | 4.3 ± 0.2 | 3.0 | 5.8 | 8.8 | 59 | 486 | 503 | 94 | 4 |
| Active Pocket Mutations | | | | | | | | | |
| RLuc8/N53D | 0.002 | 0.004 | 0.002 | 0.001 | 0.01 | | | ND | |
| RLuc8/N53Q | 0.10 | 0.16 | 0.52 | 0.04 | 0.31 | 475 | 491 | 92 | 3 |
| RLuc8/N53S | 0.001 | 0.002 | 0.003 | 0.005 | 0.03 | | | ND | |
| RLuc8/W121F | 0.05 | 0.02 | 0.02 | 0.03 | 0.15 | 478 | 496 | 94 | 3 |
| RLuc8/W121H | 0.003 | 0.002 | 0.004 | 0.01 | 0.02 | | | ND | |
| RLuc8/W121Y | 0.003 | 0.007 | 0.01 | 0.01 | 0.01 | | | ND | |

TABLE 5-continued

Results of site-directed mutagenesis in the active pocket of RLuc8.

| | Specific Actvity (relative to RLuc) | | | | Wavelength (nm) | | | |
|---|---|---|---|---|---|---|---|---|
| | native | hh | cp | n | bdc | peak | mean | fwhm | % > 600 nm |
| RLuc8/V146I | 1.1 | 1.1 | 0.60 | 0.50 | 21 | 484 | 502 | 95 | 4 |
| RLuc8/V146M | 1.0 | 0.66 | 0.51 | 0.47 | 0.43 | 481 | 498 | 94 | 3 |
| RLuc8/V146W | 0.000 | 0.000 | 0.000 | 0.000 | 0.000 | | | ND | |
| RLuc8/I150F | 0.51 | 0.56 | 0.50 | 1.0 | 5.3 | 485 | 504 | 95 | 4 |
| RLuc8/I150H | 0.53 | 0.25 | 0.19 | 2.6 | 8.1 | 494 | 514 | 98 | 6 |
| RLuc8/I150M | 2.9 | 1.8 | 3.1 | 2.2 | 24 | 488 | 508 | 95 | 5 |
| RLuc8/I150W | 0.94 | 0.65 | 0.62 | 1.3 | 8.2 | 485 | 503 | 94 | 4 |
| RLuc8/I150Y | 0.02 | 0.01 | 0.02 | 0.29 | 0.15 | 487 | 506 | 97 | 4 |
| RLuc8/W153F | 4.9 | 3.1 | 4.9 | 7.9 | 104 | 484 | 502 | 95 | 4 |
| RLuc8/W153Y | 1.2 | 0.75 | 1.1 | 2.1 | 15 | 485 | 503 | 96 | 4 |
| RLuc8/W156F | 3.9 | 2.7 | 7.2 | 12 | 81 | 486 | 504 | 93 | 4 |
| RLuc8/W156H | 0.46 | 0.48 | 0.53 | 2.3 | 1.2 | 490 | 510 | 96 | 5 |
| RLuc8/W156Y | 3.0 | 2.6 | 5.2 | 9.0 | 91 | 483 | 501 | 94 | 4 |
| RLuc8/I159F | 0.60 | 0.43 | 0.56 | 1.7 | 1.4 | 491 | 510 | 101 | 5 |
| RLuc8/I159H | 0.04 | 0.04 | 0.02 | 0.11 | 0.53 | 506 | 526 | 108 | 10 |
| RLuc8/I159W | 0.12 | 0.13 | 0.08 | 0.44 | 0.28 | 490 | 508 | 104 | 6 |
| RLuc8/I159Y | 0.003 | 0.002 | 0.01 | 0.05 | 1.1 | 513 | 536 | 113 | 13 |
| RLuc8/I163F | 0.57 | 0.80 | 0.39 | 0.61 | 7.6 | 483 | 502 | 95 | 4 |
| RLuc8/I163H | 0.16 | 0.21 | 0.12 | 0.19 | 6.1 | 499 | 519 | 102 | 7 |
| RLuc8/I163W | 0.16 | 0.26 | 0.15 | 0.26 | 2.1 | 498 | 517 | 103 | 7 |
| RLuc8/I163Y | 0.13 | 0.16 | 0.10 | 0.14 | 1.2 | 502 | 521 | 103 | 8 |
| RLuc8/I166F | 1.3 | 1.2 | 1.1 | 1.8 | 11 | 483 | 501 | 96 | 4 |
| RLuc8/I166H | 0.04 | 0.08 | 0.03 | 0.05 | 0.52 | 483 | 502 | 100 | 4 |
| RLuc8/I166L | 4.4 | 2.4 | 5.3 | 9.5 | 55 | 486 | 506 | 92 | 4 |
| RLuc8/I166W | 0.004 | 0.01 | 0.003 | 0.01 | 0.20 | 498† | 508 | 110 | 7 |
| RLuc8/I166Y | 0.23 | 0.35 | 0.16 | 0.34 | 2.5 | 493 | 508 | 99 | 5 |
| RLuc8/F180I | 0.63 | 0.65 | 0.62 | 0.70 | 8.7 | 486 | 504 | 101 | 5 |
| RLuc8/F180W | 4.0 | 2.4 | 3.3 | 4.6 | 45 | 485 | 502 | 93 | 4 |
| RLuc8/F180Y | 3.0 | 2.2 | 2.6 | 3.4 | 52 | 484 | 499 | 105 | 4 |
| RLuc8/F181W | 0.07 | 0.05 | 0.05 | 0.13 | 4.8 | 479 | 494 | 95 | 3 |
| RLuc8/F181Y | 0.07 | 0.11 | 0.03 | 0.06 | 1.2 | 497 | 515 | 103 | 6 |
| RLuc8/K189E | 4.4 | 2.6 | 3.8 | 6.7 | 61 | 484 | 501 | 95 | 4 |
| RLuc8/K189H | 3.6 | 2.0 | 1.8 | 6.1 | 44 | 485 | 502 | 94 | 4 |
| RLuc8/K189I | 1.1 | 1.0 | 4.4 | 1.9 | 19 | 484 | 500 | 96 | 4 |
| RLuc8/K189R | 0.70 | 0.86 | 0.58 | 0.45 | 1.1 | 484 | 502 | 93 | 4 |
| RLuc8/P220H | 0.003 | 0.003 | 0.003 | 0.01 | 0.05 | | | ND | |
| RLuc8/P224H | 0.08 | 0.03 | 0.07 | 0.004 | 0.29 | 484 | 500 | 95 | 4 |
| RLuc8/Y240F | 5.6 | 2.0 | 4.4 | 5.3 | 48 | 484 | 502 | 92 | 4 |
| RLuc8/F261W | 0.20 | 0.38 | 0.38 | 0.02 | 0.76 | 504 | 524 | 98 | 8 |
| RLuc8/F261Y | 0.07 | 0.93 | 0.53 | 0.01 | 16 | 487 | 506 | 97 | 4 |
| RLuc8/F261W/F262W | 0.000 | 0.000 | 0.00 | 0.002 | 0.003 | 512 | 531 | 115 | 11 |
| RLuc8/F262W | 0.60 | 0.20 | 0.23 | 0.07 | 0.02 | 500 | 521 | 99 | 7 |
| RLuc8/F262Y | 0.01 | 0.01 | 0.01 | 0.001 | 0.04 | 511 | 532 | 104 | 10 |
| RLuc8/F286W | 0.08 | 0.11 | 0.07 | 0.04 | 0.24 | 481 | 499 | 92 | 3 |
| RLuc8/F286Y | 0.07 | 0.08 | 0.23 | 0.05 | 0.24 | 482 | 501 | 93 | 4 |

The data for RLuc8 is repeated from Table 2 for the purpose of comparison. Y240 is not believed to be in the active pocket, but is proximal to it. Substrate abbreviations are as previous. Spectra were measured using coelenterazine. Specific activities are relative to that of RLuc 1 and were not corrected for the luminometer's wavelength dependent sensitivity.
†RLuc8/I166W showed a shoulder peak at 415 nm that was 28% of the height of the main peak at 498 nm.
FWHM—full width at half maximum.
ND—not determined.

TABLE 6

Results of saturation mutagenesis on RLuc8 at the putative active pocket residue of I223, along with some double mutants.

| | Specific Activity (relative to RLuc) | | | | Wavelength (nm) | | | |
|---|---|---|---|---|---|---|---|---|
| | native | h | cp | n | bdc | peak | mean | fwhm | % > 600 nm |
| RLuc8 | 4.3 ± 0.2 | 3.0 | 5.8 | 8.8 | 59 | 486 | 503 | 94 | 4 |
| I223 Mutations | | | | | | | | | |
| RLuc8/I223A | 0.68 | 0.37 | 0.94 | 0.51 | 2.0 | | | ND | |
| RLuc8/I223C | 3.0 | 1.7 | 6.2 | 3.7 | 12 | 503 | 524 | 103 | 9 |
| RLuc8/I223D | 0.01 | 0.01 | 0.01 | 0.06 | 0.10 | 503 | 524 | 106 | 9 |
| RLuc8/I223E | 0.01 | 0.01 | 0.01 | 0.11 | 0.21 | 497 | 517 | 104 | 7 |
| RLuc8/I223F | 2.7 | 2.1 | 1.8 | 2.5 | 10 | 486 | 505 | 92 | 4 |
| RLuc8/I223G | 0.14 | 0.07 | 0.12 | 0.33 | 1.3 | 498 | 518 | 105 | 7 |
| RLuc8/I223H | 0.07 | 0.05 | 0.09 | 0.43 | 1.9 | 508 | 527 | 105 | 9 |
| RLuc8/I223K | 0.002 | 0.002 | 0.001 | 0.003 | 0.26 | 491 | 509 | 97 | 5 |

TABLE 6-continued

Results of saturation mutagenesis on RLuc8 at the putative active pocket residue of I223, along with some double mutants.

| | Specific Activity (relative to RLuc) | | | | | Wavelength (nm) | | | |
|---|---|---|---|---|---|---|---|---|---|
| | native | h | cp | n | bdc | peak | mean | fwhm | % > 600 nm |
| RLuc8/I223L | 1.3 | 1.8 | 1.2 | 1.4 | 16 | 483 | 502 | 95 | 4 |
| RLuc8/I223M | 0.19 | 0.37 | 0.25 | 0.64 | 14 | 501 | 521 | 98 | 7 |
| RLuc8/I223N | 0.30 | 0.31 | 0.33 | 0.48 | 1.7 | 505 | 527 | 102 | 9 |
| RLuc8/I223P | 0.01 | 0.01 | 0.01 | 0.03 | 0.13 | 486 | 505 | 96 | 5 |
| RLuc8/I223Q | 0.06 | 0.06 | 0.06 | 0.31 | 2.3 | 505 | 527 | 102 | 9 |
| RLuc8/I223R | 0.003 | 0.002 | 0.002 | 0.01 | 0.24 | 505 | 528 | 108 | 10 |
| RLuc8/I223S | 0.61 | 0.45 | 0.49 | 0.71 | 1.7 | 499 | 517 | 104 | 7 |
| RLuc8/I223T | 0.43 | 0.36 | 0.33 | 0.48 | 0.54 | 499 | 517 | 102 | 7 |
| RLuc8/I223V | 2.5 | 1.9 | 2.8 | 3.0 | 31 | 490 | 509 | 97 | 5 |
| RLuc8/I223W | 0.003 | 0.004 | 0.01 | 0.02 | 0.01 | 484 | 508 | 104 | 7 |
| RLuc8/I223Y | 0.02 | 0.02 | 0.02 | 0.04 | 0.07 | 486 | 605 | 97 | 4 |
| Double Mutants | | | | | | | | | |
| RLuc8/I223C/F261W | 0.12 | 0.12 | 0.43 | 0.01 | 0.03 | 511 | 529 | 104 | 8 |
| RLuc8/I223C/F262W | 0.07 | 0.02 | 0.09 | 0.01 | 0.01 | 511 | 529 | 100 | 8 |
| RLuc8/I223H/F261W | 0.002 | 0.003 | 0.005 | 0.01 | 0.02 | | | ND | |
| RLuc8/I223H/F262W | 0.001 | 0.001 | 0.001 | 0.01 | 0.01 | | | ND | |
| RLuc8/I223M/F261W | 0.02 | 0.01 | 0.01 | 0.01 | 0.05 | | | ND | |
| RLuc8/I223M/F262W | 0.002 | 0.001 | 0.001 | 0.01 | 0.001 | | | ND | |
| ELuc8/I223Q/F261W | 0.003 | 0.005 | 0.003 | 0.01 | 0.02 | | | ND | |

The data for RLuc8 is repeated from Table 2 for the purpose of comparison. Substrate abbreviations are as previous. Spectra were measured using coelenterazine. Specific activities are relative to that of RLuc and were not corrected for the luminometer's wavelength dependent sensitivity.
FWHM—full width at half maximum.
ND—not determined.

Random Mutagenesis on RLuc8
Round 1—Random Mutagenesis on RLuc8/F261W, RLuc8/F262W The original purpose of the random mutagenesis study was to take some of the red-shifted mutations identified in the active pocket site directed mutagenesis study and improve their catalytic abilities. The RLuc8/F261W and RLuc8/F262W variants were picked as starting points, as they both gave rise to appreciable bathochromic shifts while not overly compromising the light output of the luciferase. Random mutagenesis was performed on these templates, and screened in bacteria for both increases in light output as well as emission color shifts. The results of this study are given in Table 6. Interestingly, several mutation locations were over represented. Of these mutations, those at residues E155 and G269 lead to increases in light output, and those at D162 lead to further bathochromic shifts in the emission spectra.

TABLE 7

Results of random mutagenesis on RLuc8/F261W and RLuc8/F262W.

| | Specific Activity | Wavelength (nm) | | | |
|---|---|---|---|---|---|
| | | peak | mean | fwhm | % > 600 nm |
| F261W Mutants | | | | | |
| RLuc8/F261W | 0.20 | 505 | 524 | 98 | 8 |
| RLuc8/R11P/F261W/V267I | 0.25 | 501 | 522 | 99 | 7 |
| RLuc8/A22P/D162N/F261W | 0.10 | 526 | 547 | 97 | 13 |
| RLuc8/V63I/L94F/F261W/F278I | 0.36 | 501 | 522 | 98 | 7 |
| RLuc8/R93L/D162E/F261W | 0.05 | 535 | 551 | 112 | 17 |
| RLuc8/L94F/F261W | 0.15 | 501 | 521 | 97 | 7 |
| RLuc8/K113R/E155K/F261W | 0.54 | 503 | 523 | 98 | 7 |
| RLuc8/A123S/F261W | 0.48 | 504 | 523 | 98 | 7 |
| RLuc8/M143T/F261W | 0.26 | 503 | 523 | 98 | 7 |
| RLuc8/D162N/F261W/S188N | 0.05 | 525 | 544 | 97 | 13 |
| RLuc8/A164T/D248E/F261W/K297N | 0.12 | 502 | 521 | 98 | 7 |
| RLuc8/F261W/N264S | 0.27 | 503 | 523 | 99 | 7 |
| RLuc8/F261W/K271R | 0.14 | 505 | 526 | 99 | 8 |
| F262W Mutants | | | | | |
| RLuc8/F262W | 0.60 | 500 | 521 | 99 | 7 |
| RLuc8/Q26K/E155K/F262W | 0.75 | 500 | 521 | 99 | 7 |
| RLuc8/P65H/A130T/F262W | 0.12 | 501 | 522 | 99 | 8 |
| RLuc8/F105V/E151K/D162E/F262W | 0.07 | 535 | 551 | 119 | 18 |
| RLuc8/A123S/F262W | 0.50 | 499 | 519 | 98 | 7 |
| RLuc8/E155G/E183D/F262W | 0.89 | 501 | 522 | 98 | 7 |
| RLuc8/E155K/E169D/F262W | 0.60 | 501 | 521 | 98 | 7 |
| RLuc8/K167M/K173N/F262W | 0.54 | 498 | 519 | 98 | 7 |
| RLuc8/V234I/F262W/G269R | 0.86 | 501 | 523 | 99 | 8 |

TABLE 7-continued

Results of random mutagenesis on RLuc8/F261W and RLuc8/F262W.

|  | Specific Activity | Wavelength (nm) | | | % > 600 nm |
|---|---|---|---|---|---|
|  |  | peak | mean | fwhm |  |
| RLuc8/F262W/G269E | 0.57 | 500 | 520 | 98 | 7 |
| RLuc8/F262W/G269R | 1.3 | 502 | 523 | 100 | 8 |
| RLuc8/F262W/M295V | 0.47 | 499 | 520 | 98 | 7 |

Mutation locations that showed up multiple times are designated by bold text. The data for RLuc8/F261W and RLuc8/F262W is repeated from Table 6 for the purpose of comparison. Coelenterazine was used for measuring the spectra and specific activity. Specific activities are relative to that of RLuc (Table 2) and were not corrected for the luminometer's wavelength dependent sensitivity.
FWHM—full width at half maximum.

Round 2—Saturation Mutagenesis at D162/I163

As the A123S mutation showed some potential for increasing the light output of RLuc8/F261W, it was incorporated into RLuc8, RLuc8/F261W, and RLuc8/F262W by site specific mutation. Although this mutation is somewhat detrimental for RLuc8 and RLuc8/F262W, it was retained with the idea that a later round of mutagenesis would be done at the F261 site. These three A123S containing templates, along with RLuc8, were used for saturation mutagenesis at the D162 residue identified in the previous random mutagenesis screen. As the D162 residue borders the active pocket residue I163, this residue was incorporated into the saturation mutagenesis screen as well. Results of saturation mutagenesis at D162/I163 performed on the templates RLuc8, RLuc8/A123S, RLuc8/A123S/F261W, and RLuc8/A123S/F262W are given in Table 8. Quite surprisingly, a single point mutation (D162E) could lead to a significant red-shift of the emission spectra of the luciferase without a severe compromise in the luciferase's ability to output light. Also interesting, is that several of the selected mutants had significant side peaks around 410 nm. This side peak is presumptively emanating from the neutral species of coelenteramide. For RLuc8/A123S/D162L/I163V, it gives the variant a whitish purple color when the bioluminescence is visualized.

TABLE 8

Results from saturation mutagenesis at the D162/I163 residues of RLuc, RLuc8/A123S, RLuc8/A123S/F261W, and RLuc8/A123S/F262W.

|  | Specific Activity | Wavelength (nm) | | | | Shoulder/Peak Ratio | % > 600 nm | Clones |
|---|---|---|---|---|---|---|---|---|
|  |  | peak | mean | fwhm | shoulder |  |  |  |
| RLuc8 Mutants |  |  |  |  |  |  |  |  |
| RLuc8 | 4.3 | 486 | 503 | 94 |  |  | 4 |  |
| RLuc8/D162E | 1.4 | 522 | 537 | 108 |  |  | 12 | 1 |
| RLuc8/D162E/I163M | 1.2 | 519 | 530 | 108 |  |  | 10 | 1 |
| RLuc8/D162E/I163T | 0.08 | 539 | 547 | 125 |  |  | 19 | 1 |
| RLuc8/D162N | 2.1 | 510 | 526 | 96 | 408 | 0.05 | 8 | 2 |
| RLuc8/D162N/I163V | 1.6 | 516 | 531 | 103 | 408 | 0.08 | 10 | 6 |
| RLuc8/D162P/I163L | 0.28 | 525 | 515 | 103 | 406 | 0.50 | 10 | 1 |
| RLuc8/D162S/I163V | 4.7 | 485 | 504 | 92 |  |  | 4 | 1 |
| RLuc8/A123S Mutants |  |  |  |  |  |  |  |  |
| RLuc8/A123S | 2.8 | 484 | 502 | 92 |  |  | 4 |  |
| RLuc8/A123S/D162C/I163V | 0.95 | 520 | 539 | 94 |  |  | 11 | 1 |
| RLuc8/A123S/D162E | 1.5 | 522 | 536 | 107 |  |  | 12 | 2 |
| RLuc8/A123S/D162E/I163L | 2.4 | 523 | 538 | 102 |  |  | 12 | 2 |
| RLuc8/A123S/D162L/I163V | 0.29 | 532 | 515 | 124 | 409 | 0.75 | 13 | 1 |
| RLuc8/A123S/D162N | 2.0 | 509 | 526 | 96 | 407 | 0.05 | 8 | 1 |
| RLuc8/A123S/D162N/I163L | 2.4 | 507 | 523 | 93 | 404 | 0.07 | 7 | 2 |
| RLuc8/A123S/D162N/I163S | 0.19 | 523 | 535 | 110 | 407 | 0.18 | 13 | 2 |
| RLuc8/A123S/D162T/I163C | 0.10 | 527 | 514 | 119 | 409 | 0.69 | 12 | 1 |
| RLuc8/A123S/F261W Mutants |  |  |  |  |  |  |  |  |
| RLuc8/A123S/F261W | 0.48 | 504 | 523 | 98 |  |  | 7 |  |
| RLuc8/A123S/D162T/F261W | 0.23 | 526 | 547 | 102 |  |  | 14 | 1 |
| RLuc8/A123S/D162E/F261W | 0.21 | 533 | 547 | 116 |  |  | 16 | 1 |
| RLuc8/A123S/D162E/I163L/F261W | 0.12 | 538 | 553 | 107 |  |  | 17 |  |
| RLuc8/A123S/D162N/I163M/F261W | 0.29 | 520 | 539 | 95 |  |  | 11 | 3 |
| RLuc8/A123S/D162N/I163V/F261W | 0.21 | 531 | 551 | 102 |  |  | 16 | 3 |
| RLuc8/A123S/F262W Mutants |  |  |  |  |  |  |  |  |
| RLuc8/A123S/F262W | 0.50 | 499 | 519 | 98 |  |  | 7 |  |
| RLuc8/A123S/D162E/I163V/F262W | 0.06 | 541 | 558 | 113 |  |  | 21 | 1 |
| RLuc8/A123S/D162N/F262W | 0.23 | 527 | 544 | 100 |  |  | 13 | 1 |

If the spectrum had a shoulder peak, it is noted above along with the ratio of the height of the shoulder peak to the main peak. Clones indicates how many colonies coded for the same protein sequences (but not necessarily the same nucleotide sequence), and is an indicator for how well the search space was covered. The data for RLuc, RLuc8/A123S/F261W, and RLuc8/A123S/F262W is repeated from previous tables for the purpose of comparison. Coelenterazine was used for measuring the spectra and specific activity. Specific activities are relative to that of RLuc, and were not corrected for the luminometer's wavelength dependent sensitivity.
FWHM—full width at half maximum.

Round 3—Saturation Mutagenesis at F261/F262

Using RLuc8/A123S and RLuc8/A123S/D162E/I163L as templates, saturation mutagenesis was done at the F261/F262 residues in an attempt to find the best color shift residues at this location. Out of ~15,000 colonies screened the mutagenesis with RLuc8/A123S as the template, only parental, Luc8/A123S/F261W, and RLuc8/A123S/F262W clones were selected by the screen. Out of ~9000 colonies screened from the mutagenesis performed using RLuc8/A123S/D162E/I163L as the template, the only non-parental clone selected by the screening process was RLuc8/A123S/D162E/I163L/F261W. The results of this screen would indicate that no further improvements in either light output or color shift were made at the F261/F262 position.

Round 4—Saturation Mutagenesis at I223/P224

As saturation mutagenesis at I223 yielded several bathochromic shift mutations, saturation mutagenesis was performed on the I223/P224 location, as well as on the 5 residues P220/R221/E222/I223/P224. The templates used in this screen were RLuc8 and RLuc8/A123S/D162E/I163L. For each of these 4 conditions, ~4000 colonies were screened for light output and/or color shifts. All the clones selected from this mutagenesis were the parental sequence, and were either parental template that had escaped the DpnI digestion, or templates containing silent mutations. No further optimization was seen in this region of the protein.

Round 5—Saturation Mutagenesis at V185/L186

With respect to increases in light output, the M185V mutation was the most interesting one that arose from the consensus sequence driven mutagenesis of Example 1. For this reason, saturation mutagenesis at V185/L186 and V185/L186/P187/S188/K189 was performed on the templates RLuc8 and RLuc8/A123S/D162E/I163L. The results of this screen are shown in Table 9. Interestingly, the V185L mutation coupled to A123S/D162E/I163L could lead to a further ~8 nm bathochromic shift in the emission spectrum, but when V185L was present alone in the RLuc8 background it led to no observable shift in the emission.

TABLE 9

Results from saturation mutagenesis at V185/L186, as well as random mutagenesis over V185/L186/P187/S188/K189.

| | Specific Activity | Wavelength (nm) | | | |
|---|---|---|---|---|---|
| | | peak | mean | fwhm | % > 600 nm |
| RLuc8 Mutants | | | | | |
| RLuc8 | 4.3 ± 0.2 | 486 | 503 | 94 | 4 |
| RLuc8/V185L | 3.3 | 485 | 504 | 95 | 4 |
| RLuc8/V185Q | 4.5 | 482 | 500 | 93 | 3 |
| RLuc8/V185K/L186M/P187A/S188A/K189L | 0.85 | 480 | 497 | 102 | 4 |
| RLuc8/A123S/D162E/I163L Mutants | | | | | |
| RLuc8/A123S/D162E/I163L | 2.4 | 523 | 538 | 102 | 12 |
| RLuc8/A123S/D162E/I163L/V185L | 2.1 | 532 | 545 | 106 | 15 |
| RLuc8/A123S/D162E/I163L/V185L/L186F | 0.72 | 530 | 541 | 110 | 14 |
| RLuc8/A123S/D162E/I163L/V185A/P187V/S188K/K189M | 0.31 | 510 | 525 | 113 | 10 |

The templates used for mutagenesis were RLuc8 and RLuc8/A123S/D162E/I163L, and for the purposes of comparison the data for these variants is repeated from previous tables where Coelenterazine was used for measuring the spectra and specific activity. Specific activities are relative to that of RLuc, and were not corrected for the luminometer's wavelength dependent sensitivity.
FWHM—full width at half maximum.

Round 6—Saturation Mutagenesis at D154/E155

Some of the more promising candidates from the previous rounds of mutagenesis were selected for saturation mutagenesis at the E155 position. E155 had been identified in the initial random mutagenesis screen as a residue that could be mutated to increase the light output from the RLuc8/F261W and RLuc8/F262W constructs, and it was hoped that mutagenesis at this location would lead to improvements in RLuc8/A123S/D162E/I163L/V185L, RLuc8/A123S/D162E/I163L/F261W, and RLuc8/A123S/D162E/I163V/F262W. The neighboring D154 position was included in this saturation mutagenesis screen as well. The results of this screen, shown in Table 10, demonstrated that significant improvements of all three parental constructs could be achieved by mutagenesis at these two positions.

TABLE 10

Results from saturation mutagenesis at the D154/E155 residues.

| | Specific Activity | Wavelength (nm) | | | % > 600 nm |
|---|---|---|---|---|---|
| | | Peak | Mean | fwhm | |
| RLuc8/A123S/D162E/I163L/V185L Mutants | | | | | |
| RLuc8/A123S/D162E/I163L/V185L | 2.1 | 532 | 545 | 106 | 15 |
| RLuc8/A123S/D154M/E155G/D162E/I163L/V185L | 3.5 | 535 | 550 | 104 | 17 |
| RLuc8/A123S/D154R/E155T/D162E/I163L/V185L | 2.9 | 531 | 546 | 104 | 15 |
| RLuc8/A123S/E155G/D162E/I163L/V185L | 3.4 | 532 | 545 | 104 | 15 |
| RLuc8/A123S/D162E/I163L/F261W Mutants | | | | | |
| RLuc8/A123S/D162E/I163L/F261W | 0.12 | 538 | 553 | 107 | 17 |
| RLuc8/A123S/D154K/E155N/D162E/I163L/F261W | 0.97 | 545 | 560 | 106 | 21 |
| RLuc8/A123S/D154R/E155G/D162E/I163L/F261W | 0.39 | 537 | 554 | 106 | 18 |
| RLuc8/A123S/E155G/D162E/I163L/F261W | 0.66 | 537 | 554 | 107 | 17 |
| RLuc8/A123S/E155K/D162E/I163L/F261W | 0.46 | 541 | 556 | 107 | 18 |
| RLuc8/A123S/D162E/I163V/F262W Mutants | | | | | |
| RLuc8/A123S/D162E/I163V/F262W | 0.06 | 541 | 558 | 113 | 21 |
| RLuc8/A123S/D154A/E155G/D162E/I163V/F262W | 0.60 | 547 | 564 | 111 | 23 |
| RLuc8/A123S/D154T/E155G/D162E/I163V/F262W | 0.54 | 544 | 560 | 112 | 21 |
| RLuc8/A123S/D154V/E155G/D162E/I163V/F262W | 0.87 | 543 | 560 | 112 | 21 |
| RLuc8/A123S/E155G/D162E/I163V/F262W | 0.80 | 543 | 560 | 111 | 21 |

The templates used for mutagenesis were RLuc8/A123S/D162E/I163L/V185L, RLuc8/A123S/D162E/I163L/F261W, and RLuc8/A123S/D162E/I163V/F262W. The data for these parental constructs are repeated from previous tables for the purpose of comparison. Coelenterazine was used for measuring the spectra and specific activity. Specific activities are relative to that of RLuc. Note that the spectral sensitivity of the luminometer's detector penalizes the red-shifted variants, and this was not corrected for here.
FWHM—full width at half maximum.

Round 7—Saturation Mutagenesis at G269/A270

In an attempt to further improve the green emitting luciferase variants, the results of the previous screen at the D154/E155 positions were applied to an additional saturation mutagenesis screen at the G269/A270 positions. The G269 residue was identified in the initial random mutagenesis screen as a position at which mutations could lead to significant improvements in the light output of RLuc8/F262W. With this in mind, saturation mutagenesis of G269 and the neighboring residue A270 was performed on the parental constructs RLuc8/A123S/E155G/D162E/I163/V185L, RLuc8/A123S/D154K/E155N/-D162E/I163L/F261W, and RLuc8/A123S/D154V/E155G/D162E/I163V/F262W. between ~3000-6000 colonies were screened for each condition, but no improved variants (with respect to light output or red-shift) were identified in the selection process.

Round 8—Random Mutagenesis on RLuc8/A123S/D154V/E155G/D162E/-I163V/F262W

In an attempt to identify locations that may yield further red-shifts in the bioluminescence emission spectrum, the RLuc8/A123S/D154V/E155G/D162E/-I163V/F262W construct was subjected to random mutagenesis. In a small screen of ~15,000 colonies, no further improvements in either light output or emission spectrum red-shifts were observed.

Discussion

Figure 13:
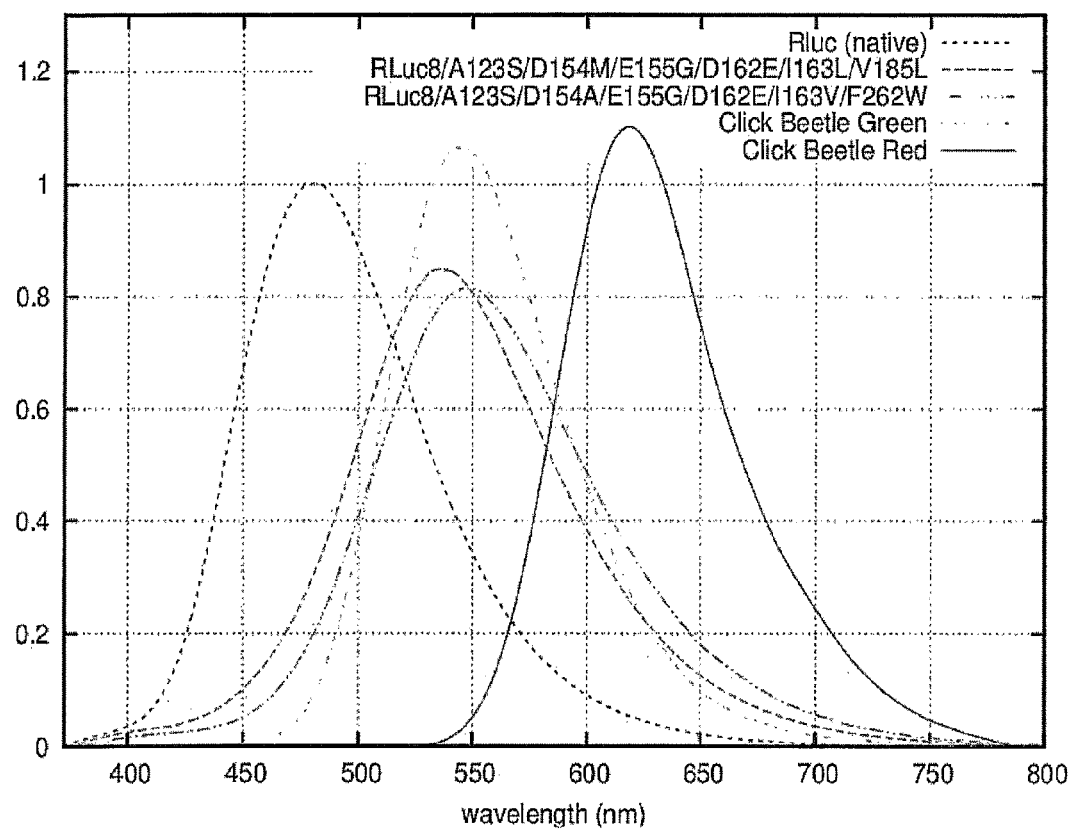
FIG. 13 illustrates normalized bioluminescence emission spectra for two of the red-shifted variants of RLuc8 that were developed. The spectra were applied after applying coelenterazine to the purified proteins. The normalization equalized the total area under the curve. The spectra for the click beetle luciferases are from Zhao et al, *Mol. Imaging.* 3:43-54, 2004 (which is incorporated by reference), and are included for comparison.

The data in this chapter shows that a green emitting coelenterazine using luciferase is indeed possible, presumably due to favoring the pyrazine anion of coelenteramide in the enzymatic pocket. Furthermore, this shift in spectrum can come with little loss in the ability of the luciferase to emit light. Bioluminescence emission spectra for two of these variants are shown in FIG. 13 in comparison to emission spectra from the click beetle luciferases.

An interesting question to ask, is how much of an effect on in vivo imaging capabilities could be expected from the ~25-65 nm emission shifts that the luciferase variants present here. The expected benefit of these bathochromic (red) shift variants is complicated by the fact that these shifts are moving the peak emission squarely into a local maximum around 550 nm in the hemoglobin absorption curve. To answer these questions, rough calculations of light attenuation were made using rat liver absorption values. Rat liver was chosen as a model organ to study because the absorption values are available in the range of wavelengths that are of interest here.

A quantitative comparison is given in Table 11, where predictions are made as to the relative gain in light output versus RLuc for the various luciferase variants at 0.1 and 0.5 cm depth of liver tissue. Again, these results underscore the advantageousness of having a red-shifted *Renilla* luciferase for small animal imaging applications. They also point out that the benefits of red-shifting the emission spectrum outweigh any penalties from the local hemoglobin absorption peak at 550 nm.

TABLE 11

Effects of tissue depth on the relative light output of several Renilla luciferase variants.

|  | Specific Activity | Corrected Activity | Wavelength mean (nm) | % Transmitted 0.1 cm | % Transmitted 0.5 cm | Effective Output 0.1 cm | Effective Output 0.5 cm |
| --- | --- | --- | --- | --- | --- | --- | --- |
| RLuc | 1.0 | 1.0 | 497 | 2.8 | 0.025 | 1.0 | 1.0 |
| RLuc8 | 4.3 | 4.3 | 503 | 3.1 | 0.029 | 4.7 | 5.0 |
| RLuc8/A123S/D162L/I163V | 0.29 | 0.35 | 515 | 5.7 | 0.17 | 0.71 | 2.4 |
| RLuc8/A123S/D162N/I163L | 2.4 | 3.1 | 523 | 4.2 | 0.065 | 4.7 | 8.1 |
| RLuc8/A123S/D162E/I163L | 2.4 | 3.6 | 538 | 5.8 | 0.13 | 7.4 | 19 |
| RLuc8/A123S/D162E/I163L/V185L | 2.1 | 3.4 | 545 | 6.9 | 0.18 | 8.4 | 25 |
| RLuc8/A123S/D154M/E155G/D162E/I163L/V185L | 3.5 | 6.0 | 550 | 7.4 | 0.20 | 16 | 48 |
| RLuc8/A123S/D154K/E155N/D162E/I163L/F261W | 0.97 | 1.9 | 560 | 8.7 | 0.26 | 5.9 | 20 |
| RLuc8/A123S/D154A/E155G/D162E/I163V/F262W | 0.60 | 1.2 | 564 | 9.7 | 0.31 | 4.2 | 15 |

Note that the spectral sensitivity of the luminometer's detector penalizes the red-shifted variants; the "Corrected Activity" takes this into account using compensation factors. "% Transmitted" is the percent of photons that are transmitted through the given depth of rat liver tissue, as calculated based on the spectra data and rat liver transmittance data. "Effective Output" is the corrected specific activity of the enzyme multiplied by the percent of photons transmitted for the given depth. The effective output values as well as the specific activity values have been normalized to those of RLuc.

It is evident from the above results and discussion that the present disclosure provides an important new class of luciferase proteins that greatly expands the utility of these molecules in a variety of different applications. As such, the subject disclosure represents a significant contribution to the art.

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

SEQ ID NO. 1 (*Renilla reniformis* wild-type luciferase polynucleotide sequence); SEQ ID NO. 2 (*Renilla reniformis* wild-type luciferase polypeptide sequence); SEQ ID NO: 3 (RLuc/A55T); SEQ ID NO: 4 (RLuc/S130A); SEQ ID NO: 5 (RLuc/K136R); SEQ ID NO: 6 (RLuc/A143M); SEQ ID NO: 7 (RLuc/M253L); SEQ ID NO: 8 (RLuc/S287L); SEQ ID NO: 9 (RLuc/Q235A); SEQ ID NO: 10 (RLuc/S257G); SEQ ID NO. 11 (Rluc/M185V); SEQ ID No: 12 (Rluc8 polynucleotide sequence); SEQ ID NO. 13 (Rluc8 protein sequence); SEQ ID NO: 14; SEQ ID NO: 15; SEQ ID NO: 16; SEQ ID NO: 17; SEQ ID NO: 18 (RLuc8/I159H); SEQ ID NO: 19: (RLuc8/I163Y); SEQ ID NO: 20: (RLuc8/F181Y); SEQ ID NO: 21: (RLuc8/I223C); SEQ ID NO: 22: (RLuc8/F261W); SEQ ID NO: 23: (RLuc8/F262W); SEQ ID NO: 24: (RLuc8/A123S/D162E/I163L); SEQ ID NO: 23: (RLuc8/A123S/D162N/I163L); SEQ ID NO: 26: (RLuc8/A123S/D162E/I163L/V185L); SEQ ID NO: 27: (RLuc8/A123S/D154M/E155G/D162E/I163L/V185L); SEQ ID NO: 28: (RLuc8/A123S/D154K/E155N/D162E/I163L/F261W); SEQ ID NO: 29: (RLuc8/A123S/D154A/E155G/D162E/I163V/F262W); SEQ ID NO: 30: (RLuc8/A123S/D154V/E155G/D162E/I163V/F262W); SEQ ID NO: 31 (RLuc8/N53Q); SEQ ID NO: 32 (RLuc8/A54P); SEQ ID NO: 33 (RLuc8/D120N; SEQ ID NO: 34 (RLuc8/W121F); SEQ ID NO: 35 (RLuc8/V146I); SEQ ID NO: 36 (RLuc81V146M); SEQ ID NO: 37 (RLuc8/F181W); SEQ ID NO: 38 (RLuc8/F286Y).

What is claimed is:

1. An isolated polynucleotide encoding a mutant Cnidarian luciferase, wherein the mutant luciferase has the sequence of SEQ ID NO:27.

2. The polynucleotide of claim 1, wherein the polynucleotide encodes a fusion protein comprising the mutant Cnidarian luciferase and at least one fusion partner.

3. The polynucleotide of claim 2, wherein the at least one fusion partner comprises an epitope tag.

4. The polynucleotide of claim 2, wherein the at least one fusion partner comprises a targeting moiety.

5. The polynucleotide of claim 4, wherein the targeting moiety is selected from the group consisting of: an antibody, a receptor, a ligand, and binding fragments or mimetics thereof.

6. The polynucleotide of claim 5, wherein the targeting moiety is a ligand that specifically binds to VEGF receptor 2.

7. The polynucleotide of claim 6, wherein the targeting moiety is VEGF 121.

8. A construct comprising: a vector and a polynucleotide according to claim 1.

9. An expression cassette comprising:
a polynucleotide according to claim 1.

10. A cell, or the progeny thereof, comprising an expression cassette according to claim 9 as part of an extrachromosomal element or integrated into the genome of a host cell as a result of introduction of the expression cassette into the host cell.

11. A method of producing a luciferase, the method comprising:
growing a cell according to claim 10, whereby the protein is expressed; and
isolating the protein substantially free of other proteins.

12. A kit comprising: a polynucleotide according to claim 1.

13. The kit of claim 12, wherein the kit further comprises a substrate for the luciferase.

14. The kit of claim 13, wherein the substrate is a coelenterazine.

* * * * *

SEQUENCE LISTING

```
<160> NUMBER OF SEQ ID NOS: 38

<210> SEQ ID NO 1
<211> LENGTH: 936
<212> TYPE: DNA
<213> ORGANISM: Renilla reniformis

<400> SEQUENCE: 1
atgacttcga aagtttatga tccagaacaa aggaaacgga tgataactgg tccgcagtgg      60
tgggccagat gtaaacaaat gaatgttctt gattcattta ttaattatta tgattcagaa     120
aaacatgcag aaaatgctgt tattttttta catggtaacg cggcctcttc ttatttatgg     180
cgacatgttg tgccacatat tgagccagta gcgcggtgta ttataccaga tcttattggt     240
atgggcaaat caggcaaatc tggtaatggt tcttataggt tacttgatca ttacaaatat     300
cttactgcat ggtttgaact tcttaattta ccaaagaaga tcattttttgt cggccatgat     360 tggggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
```

-continued

```
ttcgtggaaa ccatgttgcc atcaaaaatc atgagaaagt tagaaccaga agaatttgca    600
gcatatcttg aaccattcaa agagaaaggt gaagttcgtc gtccaacatt atcatggcct    660
cgtgaaatcc cgttagtaaa aggtggtaaa cctgacgttg tacaaattgt taggaattat    720
aatgcttatc tacgtgcaag tgatgattta ccaaaaatgt ttattgaatc ggatccagga    780 ttctttttcca atgctattgt tgaaggcgcc aagaagtttc ctaatactga atttgtcaaa    840
gtaaaaggtc ttcattttc gcaagaagat gcacctgatg aaatgggaaa atatatcaaa    900
tcgttcgttg agcgagttct caaaaatgaa caataa                             936
```

<210> SEQ ID NO 2
<211> LENGTH: 311
<212> TYPE: PRT
<213> ORGANISM: Renilla reniformis

<400> SEQUENCE: 2

```
Met Thr Ser Lys Val Tyr Asp Pro Glu Gln Arg Lys Arg Met Ile Thr
  1               5                  10                  15

Gly Pro Gln Trp Trp Ala Arg Cys Lys Gln Met Asn Val Leu Asp Ser
                 20                  25                  30

Phe Ile Asn Tyr Tyr Asp Ser Glu Lys His Ala Glu Asn Ala Val Ile
             35                  40                  45

Phe Leu His Gly Asn Ala Ala Ser Ser Tyr Leu Trp Arg His Val Val
         50                  55                  60

Pro His Ile Glu Pro Val Ala Arg Cys Ile Ile Pro Asp Leu Ile Gly
     65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300
```

-continued

Arg Val Leu Lys Asn Glu Gln
305             310

<210> SEQ ID NO 3
<211> LENGTH: 311
<212> TYPE: PRT
<213> ORGANISM: Renilla Luciferase

<400> SEQUENCE: 3

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305             310

<210> SEQ ID NO 4
<211> LENGTH: 311
<212> TYPE: PRT
<213> ORGANISM: Renilla Luciferase

<400> SEQUENCE: 4

Met Ala Ser Lys Val Tyr Asp Pro Glu Gln Arg Lys Arg Met Ile Thr

```
            1               5                  10                 15
Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
                35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ala Cys Leu Ala Phe His
                115                 120                 125

Tyr Ala Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Ser Gln
                275                 280                 285

Glu Asp Ala Pro Asp Glu Met Gly Lys Tyr Ile Lys Ser Phe Val Glu
                290                 295                 300

Arg Val Leu Lys Asn Glu Gln
305                 310

<210> SEQ ID NO 5
<211> LENGTH: 311
<212> TYPE: PRT
<213> ORGANISM: Renilla Luciferase

<400> SEQUENCE: 5

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
                35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
```

```
                65                  70                  75                  80
Met Gly Lys Ser Gly Lys Ser Gly Asn Gly Ser Tyr Arg Leu Leu Asp
                    85                  90                  95

His Tyr Lys Tyr Leu Thr Ala Trp Phe Glu Leu Leu Asn Leu Pro Lys
                    100                 105                 110

Lys Ile Ile Phe Val Gly His Asp Trp Gly Ala Cys Leu Ala Phe His
                    115                 120                 125

Tyr Ser Tyr Glu His Gln Asp Arg Ile Lys Ala Ile Val His Ala Glu
                    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                    165                 170                 175

Glu Asn Asn Phe Phe Val Glu Thr Met Leu Pro Ser Lys Ile Met Arg
                    180                 185                 190

Lys Leu Glu Pro Glu Glu Phe Ala Ala Tyr Leu Glu Pro Phe Lys Glu
                    195                 200                 205

Lys Gly Glu Val Arg Arg Pro Thr Leu Ser Trp Pro Arg Glu Ile Pro
                    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                    245                 250                 255

Ser Asp Pro Gly Phe Phe Ser Asn Ala Ile Val Glu Gly Ala Lys Lys
                    260                 265                 270

Phe Pro Asn Thr Glu Phe Val Lys Val Lys Gly Leu His Phe Ser Gln
                    275                 280                 285

Glu Asp Ala Pro Asp Glu Met Gly Lys Tyr Ile Lys Ser Phe Val Glu
                    290                 295                 300

Arg Val Leu Lys Asn Glu Gln
305                 310

<210> SEQ ID NO 6
<211> LENGTH: 311
<212> TYPE: PRT
<213> ORGANISM: Renilla Luciferase

<400> SEQUENCE: 6

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                    20                  25                  30

Phe Ile Asn Tyr Tyr Asp Ser Glu Lys His Ala Glu Asn Ala Val Ile
                    35                  40                  45

Phe Leu His Gly Asn Ala Ala Ser Ser Tyr Leu Trp Arg His Val Val
                    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                    85                  90                  95

His Tyr Lys Tyr Leu Thr Ala Trp Phe Glu Leu Leu Asn Leu Pro Lys
                    100                 105                 110

Lys Ile Ile Phe Val Gly His Asp Trp Gly Ala Cys Leu Ala Phe His
                    115                 120                 125

Tyr Ser Tyr Glu His Gln Asp Lys Ile Lys Ala Ile Val His Met Glu
```

```
                130                 135                 140
Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 7
<211> LENGTH: 311
<212> TYPE: PRT
<213> ORGANISM: Renilla Luciferase

<400> SEQUENCE: 7

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
            35                  40                  45

Phe Leu His Gly Asn Ala Ala Ser Ser Tyr Leu Trp Arg His Val Val
        50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
```

```
                195                 200                 205
Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Leu Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 8
<211> LENGTH: 311
<212> TYPE: PRT
<213> ORGANISM: Renilla Luciferase

<400> SEQUENCE: 8

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
            245                 250                 255

Ser Asp Pro Gly Phe Phe Ser Asn Ala Ile Val Glu Gly Ala Lys Lys
        260                 265                 270
```

```
                260                 265                 270
Phe Pro Asn Thr Glu Phe Val Lys Val Lys Gly Leu His Phe Leu Gln
            275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 9
<211> LENGTH: 311
<212> TYPE: PRT
<213> ORGANISM: Renilla Luciferase

<400> SEQUENCE: 9

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Ala Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

```
<210> SEQ ID NO 10
<211> LENGTH: 311
<212> TYPE: PRT
<213> ORGANISM: Renilla Luciferase

<400> SEQUENCE: 10

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Gly Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 11
<211> LENGTH: 311
<212> TYPE: PRT
<213> ORGANISM: Renilla Luciferase

<400> SEQUENCE: 11

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30
```

```
Phe Ile Asn Tyr Tyr Asp Ser Glu Lys His Ala Glu Asn Ala Val Ile
            35                  40                  45

Phe Leu His Gly Asn Ala Ala Ser Ser Tyr Leu Trp Arg His Val Val
 50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 12
<211> LENGTH: 933
<212> TYPE: DNA
<213> ORGANISM: Renilla Luciferase

<400> SEQUENCE: 12
atggcttcca aggtgtacga ccccgagcaa cgcaaacgca tgatcactgg gcctcagtgg     60
tgggctcgct gcaagcaaat gaacgtgctg gactccttca tcaactacta tgattccgag    120
aagcacgccg agaacgccgt gatttttctg catggtaacg ctacctccag ctacctgtgg    180
aggcacgtcg tgcctcacat cgagcccgtg gctagatgca tcatccctga tctgatcgga    240
atgggtaagt ccggcaagag cgggaatggc tcatatcgcc tcctggatca ctacaagtac    300
ctcaccgctt ggttcgagct gctgaacctt ccaaagaaaa tcatctttgt gggccacgac    360
tggggggctg ctctggcctt tcactacgcc tacgagcacc aagacaggat caaggccatc    420
gtccatatgg agagtgtcgt ggacgtgatc gagtcctggg acgagtggcc tgacatcgag    480
gaggatatcg ccctgatcaa gagcgaagag ggcgagaaaa tggtgcttga gaataacttc    540
```

```
ttcgtcgaga ccgtgctccc aagcaagatc atgcggaaac tggagcctga ggagttcgct      600
gcctacctgg agccattcaa ggagaagggc gaggttagac ggcctaccct ctcctggcct      660
cgcgagatcc ctctcgttaa gggaggcaag cccgacgtcg tccagattgt ccgcaactac      720
aacgcctacc ttcgggccag cgacgatctg cctaagctgt tcatcgagtc cgaccctggg      780
ttcttttcca acgctattgt cgagggagct aagaagttcc ctaacaccga gttcgtgaag      840
gtgaagggcc tccacttcct ccaggaggac gctccagatg aaatgggtaa gtacatcaag      900
agcttcgtgg agcgcgtgct gaagaacgag cag                                   933
```

```
<210> SEQ ID NO 13
<211> LENGTH: 311
<212> TYPE: PRT
<213> ORGANISM: Renilla Luciferase

<400> SEQUENCE: 13
```

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

-continued

Arg Val Leu Lys Asn Glu Gln
305                 310

<210> SEQ ID NO 14
<211> LENGTH: 29
<212> TYPE: DNA
<213> ORGANISM: Artificial Sequence
<220> FEATURE:
<223> OTHER INFORMATION: Chemically synthesized primer sequence

<400> SEQUENCE: 14
acgtcaattg ggaatggcag aaggaggag                                  29

<210> SEQ ID NO 15
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 15
aaggtcgacc cgcctcggct tgtc                                       24

<210> SEQ ID NO 16
<211> LENGTH: 49
<212> TYPE: DNA
<213> ORGANISM: Artificial Sequence
<220> FEATURE:
<223> OTHER INFORMATION: Chemically synthesized primer sequence

<400> SEQUENCE: 16
caacatcacc atgcagatta tggcagcagc acctcaccaa ggccagcac            49

<210> SEQ ID NO 17
<211> LENGTH: 49
<212> TYPE: DNA
<213> ORGANISM: Artificial Sequence
<220> FEATURE:
<223> OTHER INFORMATION: Chemically synthesized primer sequence

<400> SEQUENCE: 17
gtgctggcct tggtgaggtg ctgctgccat aatctgcatg gtgatgttg            49

<210> SEQ ID NO 18
<211> LENGTH: 311
<212> TYPE: PRT
<213> ORGANISM: Renilla Luciferase

<400> SEQUENCE: 18

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

-continued

```
Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp His Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 19
<211> LENGTH: 311
<212> TYPE: PRT
<213> ORGANISM: Renilla Luciferase

<400> SEQUENCE: 19

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Tyr Ala Leu Ile Lys Ser Glu Glu Gly Glu Lys Met Val Leu
                165                 170                 175
```

```
Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 20
<211> LENGTH: 311
<212> TYPE: PRT
<213> ORGANISM: Renilla Luciferase

<400> SEQUENCE: 20

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Tyr Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240
```

```
Asn Ala Tyr Leu Arg Ala Ser Asp Asp Leu Pro Lys Leu Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 21
<211> LENGTH: 311
<212> TYPE: PRT
<213> ORGANISM: Renilla Luciferase

<400> SEQUENCE: 21

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Cys Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300
```

```
Arg Val Leu Lys Asn Glu Gln
305                 310

<210> SEQ ID NO 22
<211> LENGTH: 311
<212> TYPE: PRT
<213> ORGANISM: Renilla Luciferase

<400> SEQUENCE: 22

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Trp Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 23
<211> LENGTH: 311
<212> TYPE: PRT
<213> ORGANISM: Renilla Luciferase

<400> SEQUENCE: 23

Met Ala Ser Lys Val Tyr Asp Pro Glu Gln Arg Lys Arg Met Ile Thr
```

```
                   1               5                  10                 15
Gly Pro Gln Trp Trp Ala Arg Cys Lys Gln Met Asn Val Leu Asp Ser
                20                  25                 30

Phe Ile Asn Tyr Tyr Asp Ser Glu Lys His Ala Glu Asn Ala Val Ile
                35                  40                 45

Phe Leu His Gly Asn Ala Thr Ser Ser Tyr Leu Trp Arg His Val Val
 50                 55                  60

Pro His Ile Glu Pro Val Ala Arg Cys Ile Ile Pro Asp Leu Ile Gly
 65                 70                  75                 80

Met Gly Lys Ser Gly Lys Ser Gly Asn Gly Ser Tyr Arg Leu Leu Asp
                85                  90                 95

His Tyr Lys Tyr Leu Thr Ala Trp Phe Glu Leu Leu Asn Leu Pro Lys
                100                 105                110

Lys Ile Ile Phe Val Gly His Asp Trp Gly Ala Ala Leu Ala Phe His
                115                 120                125

Tyr Ala Tyr Glu His Gln Asp Arg Ile Lys Ala Ile Val His Met Glu
                130                 135                140

Ser Val Val Asp Val Ile Glu Ser Trp Asp Glu Trp Pro Asp Ile Glu
145                 150                 155                160

Glu Asp Ile Ala Leu Ile Lys Ser Glu Glu Gly Glu Lys Met Val Leu
                165                 170                175

Glu Asn Asn Phe Phe Val Glu Thr Leu Pro Ser Lys Ile Met Arg
                180                 185                190

Lys Leu Glu Pro Glu Glu Phe Ala Ala Tyr Leu Glu Pro Phe Lys Glu
                195                 200                205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                240

Asn Ala Tyr Leu Arg Ala Ser Asp Asp Leu Pro Lys Leu Phe Ile Glu
                245                 250                255

Ser Asp Pro Gly Phe Trp Ser Asn Ala Ile Val Glu Gly Ala Lys Lys
                260                 265                270

Phe Pro Asn Thr Glu Phe Val Lys Val Lys Gly Leu His Phe Leu Gln
                275                 280                285

Glu Asp Ala Pro Asp Glu Met Gly Lys Tyr Ile Lys Ser Phe Val Glu
                290                 295                300

Arg Val Leu Lys Asn Glu Gln
305                 310

<210> SEQ ID NO 24
<211> LENGTH: 311
<212> TYPE: PRT
<213> ORGANISM: Renilla Luciferase

<400> SEQUENCE: 24

Met Ala Ser Lys Val Tyr Asp Pro Glu Gln Arg Lys Arg Met Ile Thr
1               5                   10                 15

Gly Pro Gln Trp Trp Ala Arg Cys Lys Gln Met Asn Val Leu Asp Ser
                20                  25                 30

Phe Ile Asn Tyr Tyr Asp Ser Glu Lys His Ala Glu Asn Ala Val Ile
                35                  40                 45

Phe Leu His Gly Asn Ala Thr Ser Ser Tyr Leu Trp Arg His Val Val
 50                 55                  60

Pro His Ile Glu Pro Val Ala Arg Cys Ile Ile Pro Asp Leu Ile Gly
```

```
                65                  70                  75                  80
Met Gly Lys Ser Gly Lys Ser Gly Asn Gly Ser Tyr Arg Leu Leu Asp
                    85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ser Ala Leu Ala Phe His
                115                 120                 125

Tyr Ala Tyr Glu His Gln Asp Arg Ile Lys Ala Ile Val His Met Glu
            130                 135                 140

Ser Val Val Asp Val Ile Glu Ser Trp Asp Glu Trp Pro Asp Ile Glu
145                 150                 155                 160

Glu Leu Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
            210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Leu Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Leu Gln
                275                 280                 285

Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 25
<211> LENGTH: 311
<212> TYPE: PRT
<213> ORGANISM: Renilla Luciferase

<400> SEQUENCE: 25

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
                35                  40                  45

Phe Leu His Gly Asn Ala Thr Ser Ser Tyr Leu Trp Arg His Val Val
            50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ser Ala Leu Ala Phe His
                115                 120                 125

Tyr Ala Tyr Glu His Gln Asp Arg Ile Lys Ala Ile Val His Met Glu
```

```
                130                 135                 140
Ser Val Val Asp Val Ile Glu Ser Trp Asp Glu Trp Pro Asp Ile Glu
145                 150                 155                 160

Glu Asn Leu Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Leu Gln
                275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 26
<211> LENGTH: 311
<212> TYPE: PRT
<213> ORGANISM: Renilla Luciferase

<400> SEQUENCE: 26

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
                35                  40                  45

Phe Leu His Gly Asn Ala Thr Ser Ser Tyr Leu Trp Arg His Val Val
                50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ser Ala Leu Ala Phe His
                115                 120                 125

Tyr Ala Tyr Glu His Gln Asp Arg Ile Lys Ala Ile Val His Met Glu
                130                 135                 140

Ser Val Val Asp Val Ile Glu Ser Trp Asp Glu Trp Pro Asp Ile Glu
145                 150                 155                 160

Glu Glu Leu Ala Leu Ile Lys Ser Glu Glu Gly Glu Lys Met Val Leu
                165                 170                 175

Glu Asn Asn Phe Phe Val Glu Thr Leu Leu Pro Ser Lys Ile Met Arg
                180                 185                 190

Lys Leu Glu Pro Glu Glu Phe Ala Ala Tyr Leu Glu Pro Phe Lys Glu
```

```
            195                 200                 205
Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Leu Gln
    275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 27
<211> LENGTH: 311
<212> TYPE: PRT
<213> ORGANISM: Renilla Luciferase

<400> SEQUENCE: 27

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ser Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Met Gly Trp Pro Asp Ile Glu
145                 150                 155                 160

Glu Glu Leu Ala Leu Ile Lys Ser Glu Glu Gly Glu Lys Met Val Leu
                165                 170                 175

Glu Asn Asn Phe Phe Val Glu Thr Leu Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
            245                 250                 255

Ser Asp Pro Gly Phe Phe Ser Asn Ala Ile Val Glu Gly Ala Lys Lys
```

```
                        260                 265                 270
Phe Pro Asn Thr Glu Phe Val Lys Val Lys Gly Leu His Phe Leu Gln
            275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 28
<211> LENGTH: 311
<212> TYPE: PRT
<213> ORGANISM: Renilla Luciferase

<400> SEQUENCE: 28

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ser Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Lys Asn Trp Pro Asp Ile Glu
145                 150                 155                 160

Glu Glu Leu Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Trp Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

-continued

```
<210> SEQ ID NO 29
<211> LENGTH: 311
<212> TYPE: PRT
<213> ORGANISM: Renilla Luciferase

<400> SEQUENCE: 29

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ser Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Ala Gly Trp Pro Asp Ile Glu
145                 150                 155                 160

Glu Glu Val Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Trp Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 30
<211> LENGTH: 311
<212> TYPE: PRT
<213> ORGANISM: Renilla Luciferase

<400> SEQUENCE: 30

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30
```

```
Phe Ile Asn Tyr Tyr Asp Ser Glu Lys His Ala Glu Asn Ala Val Ile
             35                   40                  45

Phe Leu His Gly Asn Ala Thr Ser Ser Tyr Leu Trp Arg His Val Val
 50                      55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
             100                 105                 110

Lys Ile Ile Phe Val Gly His Asp Trp Gly Ser Ala Leu Ala Phe His
             115                 120                 125

Tyr Ala Tyr Glu His Gln Asp Arg Ile Lys Ala Ile Val His Met Glu
 130                 135                 140

Ser Val Val Asp Val Ile Glu Ser Trp Val Gly Trp Pro Asp Ile Glu
145                 150                 155                 160

Glu Glu Val Ala Leu Ile Lys Ser Glu Glu Gly Glu Lys Met Val Leu
                 165                 170                 175

Glu Asn Asn Phe Phe Val Glu Thr Val Leu Pro Ser Lys Ile Met Arg
             180                 185                 190

Lys Leu Glu Pro Glu Glu Phe Ala Ala Tyr Leu Glu Pro Phe Lys Glu
             195                 200                 205

Lys Gly Glu Val Arg Arg Pro Thr Leu Ser Trp Pro Arg Glu Ile Pro
 210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                 245                 250                 255

Ser Asp Pro Gly Phe Trp Ser Asn Ala Ile Val Glu Gly Ala Lys Lys
             260                 265                 270

Phe Pro Asn Thr Glu Phe Val Lys Val Lys Gly Leu His Phe Leu Gln
             275                 280                 285

Glu Asp Ala Pro Asp Glu Met Gly Lys Tyr Ile Lys Ser Phe Val Glu
 290                 295                 300

Arg Val Leu Lys Asn Glu Gln
305                 310

<210> SEQ ID NO 31
<211> LENGTH: 311
<212> TYPE: PRT
<213> ORGANISM: Renilla Luciferase

<400> SEQUENCE: 31

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                 20                  25                  30

Phe Ile Asn Tyr Tyr Asp Ser Glu Lys His Ala Glu Asn Ala Val Ile
             35                   40                  45

Phe Leu His Gly Gln Ala Thr Ser Ser Tyr Leu Trp Arg His Val Val
 50                      55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95
```

```
His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 32
<211> LENGTH: 311
<212> TYPE: PRT
<213> ORGANISM: Renilla Luciferase

<400> SEQUENCE: 32

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Pro Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160
```

-continued

```
Glu Asp Ile Ala Leu Ile Lys Ser Glu Glu Gly Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
                275                 280                 285

Glu Asp Ala Pro Asp Glu Met Gly Lys Tyr Ile Lys Ser Phe Val Glu
            290                 295                 300

Arg Val Leu Lys Asn Glu Gln
305                 310

<210> SEQ ID NO 33
<211> LENGTH: 311
<212> TYPE: PRT
<213> ORGANISM: Renilla Luciferase

<400> SEQUENCE: 33

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
            35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asn Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
        210                 215                 220
```

```
Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Leu Gln
    275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 34
<211> LENGTH: 311
<212> TYPE: PRT
<213> ORGANISM: Renilla Luciferase

<400> SEQUENCE: 34

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Phe Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
            245                 250                 255

Ser Asp Pro Gly Phe Phe Ser Asn Ala Ile Val Glu Gly Ala Lys Lys
        260                 265                 270

Phe Pro Asn Thr Glu Phe Val Lys Val Lys Gly Leu His Phe Leu Gln
    275                 280                 285
```

```
Glu Asp Ala Pro Asp Glu Met Gly Lys Tyr Ile Lys Ser Phe Val Glu
    290                 295                 300
Arg Val Leu Lys Asn Glu Gln
305                 310

<210> SEQ ID NO 35
<211> LENGTH: 311
<212> TYPE: PRT
<213> ORGANISM: Renilla Luciferase

<400> SEQUENCE: 35

Met Ala Ser Lys Val Tyr Asp Pro Glu Gln Arg Lys Arg Met Ile Thr
 1               5                  10                  15
Gly Pro Gln Trp Trp Ala Arg Cys Lys Gln Met Asn Val Leu Asp Ser
             20                  25                  30
Phe Ile Asn Tyr Tyr Asp Ser Glu Lys His Ala Glu Asn Ala Val Ile
         35                  40                  45
Phe Leu His Gly Asn Ala Thr Ser Ser Tyr Leu Trp Arg His Val Val
     50                  55                  60
Pro His Ile Glu Pro Val Ala Arg Cys Ile Ile Pro Asp Leu Ile Gly
 65                  70                  75                  80
Met Gly Lys Ser Gly Lys Ser Gly Asn Gly Ser Tyr Arg Leu Leu Asp
                 85                  90                  95
His Tyr Lys Tyr Leu Thr Ala Trp Phe Glu Leu Leu Asn Leu Pro Lys
            100                 105                 110
Lys Ile Ile Phe Val Gly His Asp Trp Gly Ala Ala Leu Ala Phe His
        115                 120                 125
Tyr Ala Tyr Glu His Gln Asp Arg Ile Lys Ala Ile Val His Met Glu
    130                 135                 140
Ser Ile Val Asp Val Ile Glu Ser Trp Asp Glu Trp Pro Asp Ile Glu
145                 150                 155                 160
Glu Asp Ile Ala Leu Ile Lys Ser Glu Glu Gly Glu Lys Met Val Leu
                165                 170                 175
Glu Asn Asn Phe Phe Val Glu Thr Val Leu Pro Ser Lys Ile Met Arg
            180                 185                 190
Lys Leu Glu Pro Glu Glu Phe Ala Ala Tyr Leu Glu Pro Phe Lys Glu
        195                 200                 205
Lys Gly Glu Val Arg Arg Pro Thr Leu Ser Trp Pro Arg Glu Ile Pro
    210                 215                 220
Leu Val Lys Gly Gly Lys Pro Asp Val Val Gln Ile Val Arg Asn Tyr
225                 230                 235                 240
Asn Ala Tyr Leu Arg Ala Ser Asp Asp Leu Pro Lys Leu Phe Ile Glu
                245                 250                 255
Ser Asp Pro Gly Phe Phe Ser Asn Ala Ile Val Glu Gly Ala Lys Lys
            260                 265                 270
Phe Pro Asn Thr Glu Phe Val Lys Val Lys Gly Leu His Phe Leu Gln
        275                 280                 285
Glu Asp Ala Pro Asp Glu Met Gly Lys Tyr Ile Lys Ser Phe Val Glu
    290                 295                 300
Arg Val Leu Lys Asn Glu Gln
305                 310

<210> SEQ ID NO 36
<211> LENGTH: 311
<212> TYPE: PRT
<213> ORGANISM: Renilla Luciferase
```

<400> SEQUENCE: 36

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Met Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 37
<211> LENGTH: 311
<212> TYPE: PRT
<213> ORGANISM: Renilla Luciferase

<400> SEQUENCE: 37

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45
```

```
Phe Leu His Gly Asn Ala Thr Ser Ser Tyr Leu Trp Arg His Val Val
 50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Trp Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
290                 295                 300

Arg Val Leu Lys Asn Glu Gln
305                 310

<210> SEQ ID NO 38
<211> LENGTH: 311
<212> TYPE: PRT
<213> ORGANISM: Renilla Luciferase

<400> SEQUENCE: 38

Met Ala Ser Lys Val Tyr Asp Pro Glu Gln Arg Lys Arg Met Ile Thr
 1               5                  10                  15

Gly Pro Gln Trp Trp Ala Arg Cys Lys Gln Met Asn Val Leu Asp Ser
                 20                  25                  30

Phe Ile Asn Tyr Tyr Asp Ser Glu Lys His Ala Glu Asn Ala Val Ile
            35                  40                  45

Phe Leu His Gly Asn Ala Thr Ser Ser Tyr Leu Trp Arg His Val Val
 50                  55                  60

Pro His Ile Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Ala Trp Phe Glu Leu Leu Asn Leu Pro Lys
            100                 105                 110
```

-continued

```
Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Tyr Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```